US010518981B2

(12) United States Patent
Greyshock

(10) Patent No.: US 10,518,981 B2
(45) Date of Patent: Dec. 31, 2019

(54) APPARATUSES, SYSTEMS, AND METHODS FOR TRANSPORTING MEDICATIONS FROM A CENTRAL PHARMACY TO A PATIENT IN A HEALTHCARE FACILITY

(71) Applicant: AESYNT INCORPORATED, Cranberry, PA (US)

(72) Inventor: Shawn T. Greyshock, Tarentum, PA (US)

(73) Assignee: Aesynt Incorporated, Cranberry, PA (US)

(*) Notice: Subject to any disclaimer, the term of this patent is extended or adjusted under 35 U.S.C. 154(b) by 0 days.

(21) Appl. No.: 16/391,921

(22) Filed: Apr. 23, 2019

(65) Prior Publication Data

US 2019/0308819 A1 Oct. 10, 2019

Related U.S. Application Data

(63) Continuation of application No. 16/018,580, filed on Jun. 26, 2018, now Pat. No. 10,315,851, which is a
(Continued)

(51) Int. Cl.
*G06F 7/00* (2006.01)
*G06F 17/00* (2019.01)
(Continued)

(52) U.S. Cl.
CPC ............ *B65G 35/00* (2013.01); *B65G 1/137* (2013.01); *B65G 47/04* (2013.01); *G16H 20/10* (2018.01); *G16H 20/13* (2018.01)

(58) Field of Classification Search
None
See application file for complete search history.

(56) References Cited

U.S. PATENT DOCUMENTS 3,012,519 A 12/1961 Bingham
3,689,713 A 9/1972 Shkredka
(Continued)

FOREIGN PATENT DOCUMENTS

EP 1 398 277 A1 3/2004
EP 1 407 992 A1 4/2004
(Continued)

OTHER PUBLICATIONS

Final Office Action for U.S. Appl. No. 13/835,599 dated Mar. 17, 2015.
(Continued)

*Primary Examiner* — Yolanda R Cumbess
(74) *Attorney, Agent, or Firm* — Alston & Bird LLP

(57) ABSTRACT

Provided herein are various apparatuses, systems, and methods for improving the efficiency of medication distribution within a healthcare facility. In particular, embodiments may provide for dispensing medications needed and medications anticipated to be needed to an authorized medical person for administration to a patient in a healthcare facility. Methods may include receiving an indication of one or more unit dose medications anticipated to be needed by a patient; retrieving the one or more unit dose medications from a unit storage device; loading the one or more unit dose medications onto a transport device; transporting the one or more unit dose medications from the unit storage device to a location proximate the patient; and transferring the one or more unit dose medications from the transport device to a staging area at the location proximate the patient.

20 Claims, 57 Drawing Sheets

Related U.S. Application Data continuation of application No. 15/057,783, filed on Mar. 1, 2016, now Pat. No. 10,029,856, which is a continuation of application No. 13/836,107, filed on Mar. 15, 2013, now Pat. No. 9,511,945.

(60) Provisional application No. 61/713,228, filed on Oct. 12, 2012, provisional application No. 61/713,258, filed on Oct. 12, 2012, provisional application No. 61/713,268, filed on Oct. 12, 2012, provisional application No. 61/713,278, filed on Oct. 12, 2012, provisional application No. 61/713,298, filed on Oct. 12, 2012, provisional application No. 61/713,307, filed on Oct. 12, 2012, provisional application No. 61/713,321, filed on Oct. 12, 2012, provisional application No. 61/713,395, filed on Oct. 12, 2012, provisional application No. 61/713,360, filed on Oct. 12, 2012, provisional application No. 61/713,370, filed on Oct. 12, 2012, provisional application No. 61/713,409, filed on Oct. 12, 2012.

(51) Int. Cl.
  *B65G 35/00* (2006.01)
  *B65G 47/04* (2006.01)
  *G16H 20/10* (2018.01)
  *G16H 20/13* (2018.01)
  *B65G 1/137* (2006.01)

(56) References Cited

U.S. PATENT DOCUMENTS

| | | | |
|---|---|---|---|
| 3,801,751 | A | 4/1974 | Ross, Jr. |
| 3,831,130 | A | 8/1974 | Valtonen |
| 4,020,300 | A | 4/1977 | Nassif |
| 4,220,229 | A | 9/1980 | Wampfler |
| 4,403,733 | A | 9/1983 | Bach et al. |
| 4,550,231 | A | 10/1985 | Ross, Sr. |
| 4,717,042 | A | 1/1988 | McLaughlin |
| 4,785,969 | A | 11/1988 | McLaughlin |
| 4,847,764 | A | 7/1989 | Halvorson |
| 4,860,662 | A | 8/1989 | Matsumoto et al. |
| 5,014,875 | A | 5/1991 | McLaughlin et al. |
| 5,058,507 | A | 10/1991 | Muth |
| 5,069,141 | A | 12/1991 | Ohara et al. |
| 5,190,185 | A | 3/1993 | Blechl |
| 5,235,917 | A | 8/1993 | Luck et al. |
| 5,314,243 | A | 5/1994 | McDonald et al. |
| 5,346,297 | A | 9/1994 | Colson, Jr. et al. |
| 5,377,864 | A | 1/1995 | Blechl et al. |
| 5,405,048 | A | 4/1995 | Rogers et al. |
| 5,431,299 | A | 7/1995 | Brewer et al. |
| 5,460,294 | A | 10/1995 | Williams |
| 5,468,110 | A | 11/1995 | McDonald et al. |
| 5,480,062 | A | 1/1996 | Rogers et al. |
| 5,520,450 | A | 5/1996 | Colson, Jr. et al. |
| 5,555,814 | A | 9/1996 | Burkhalter et al. |
| 5,564,803 | A | 10/1996 | McDonald et al. |
| 5,593,267 | A | 1/1997 | McDonald et al. |
| 5,617,796 | A | 4/1997 | Trenner et al. |
| 5,661,978 | A | 9/1997 | Holmes et al. |
| D384,578 | S | 10/1997 | Wangu et al. |
| 5,713,485 | A | 2/1998 | Liff et al. |
| 5,716,114 | A | 2/1998 | Holmes et al. |
| 5,745,366 | A | 4/1998 | Higham et al. |
| 5,761,877 | A | 6/1998 | Quandt |
| 5,797,515 | A | 8/1998 | Liff et al. |
| 5,805,456 | A | 9/1998 | Higham et al. |
| 5,842,976 | A | 12/1998 | Williamson |
| 5,878,885 | A | 3/1999 | Wangu et al. |
| 5,880,443 | A | 3/1999 | McDonald et al. |
| 5,883,806 | A | 3/1999 | Meador et al. |
| 5,893,697 | A | 4/1999 | Zini et al. |
| 5,905,653 | A | 5/1999 | Higham et al. |
| 5,912,818 | A | 6/1999 | McGrady et al. |
| 5,927,540 | A | 7/1999 | Godlewski |
| 5,940,306 | A | 8/1999 | Gardner et al. |
| 5,971,593 | A | 10/1999 | McGrady |
| 6,003,006 | A | 12/1999 | Colella et al. |
| 6,011,999 | A | 1/2000 | Holmes |
| 6,021,392 | A | 2/2000 | Lester et al. |
| 6,036,427 | A | 3/2000 | Kita et al. |
| 6,039,467 | A | 3/2000 | Holmes |
| 6,065,819 | A | 5/2000 | Holmes et al. |
| 6,068,156 | A | 5/2000 | Liff et al. |
| 6,109,774 | A | 8/2000 | Holmes et al. |
| 6,112,502 | A | 9/2000 | Frederick et al. |
| 6,116,461 | A | 9/2000 | Broadfield et al. |
| 6,151,536 | A | 11/2000 | Arnold et al. |
| 6,155,382 | A | 12/2000 | Duijnstee |
| 6,170,230 | B1 | 1/2001 | Chudy et al. |
| 6,176,392 | B1 | 1/2001 | William et al. |
| 6,189,727 | B1 | 2/2001 | Shoenfeld |
| 6,223,934 | B1 | 5/2001 | Shoenfeld |
| 6,256,967 | B1 | 7/2001 | Hebron et al. |
| 6,283,322 | B1 | 9/2001 | Liff et al. |
| 6,289,656 | B1 | 9/2001 | Wangu et al. |
| 6,338,007 | B1 | 1/2002 | Broadfield et al. |
| 6,339,732 | B1 | 1/2002 | Phoon et al. |
| 6,361,263 | B1 | 3/2002 | Dewey et al. |
| 6,370,841 | B1 | 4/2002 | Chudy et al. |
| 6,449,927 | B2 | 9/2002 | Hebron et al. |
| 6,471,089 | B2 | 10/2002 | Liff et al. |
| 6,497,342 | B2 | 12/2002 | Zhang et al. |
| 6,499,270 | B2 | 12/2002 | Peroni et al. |
| 6,532,399 | B2 | 3/2003 | Mase |
| 6,564,121 | B1 | 5/2003 | Wallace et al. |
| 6,578,734 | B1 | 6/2003 | Coughlin et al. |
| 6,581,798 | B2 | 6/2003 | Liff et al. |
| 6,592,005 | B1 | 7/2003 | Coughlin et al. |
| 6,609,047 | B1 | 8/2003 | Lipps |
| 6,611,733 | B1 | 8/2003 | De La Huerga |
| 6,616,010 | B2 | 9/2003 | Yuyama et al. |
| 6,622,887 | B1 | 9/2003 | Roediger |
| 6,625,518 | B2 | 9/2003 | Depeursinge |
| 6,625,952 | B1 | 9/2003 | Chudy et al. |
| 6,640,159 | B2 | 10/2003 | Holmes et al. |
| 6,650,964 | B2 | 11/2003 | Spano, Jr. et al. |
| 6,659,693 | B1 | 12/2003 | Perkins et al. |
| 6,671,579 | B2 | 12/2003 | Spano, Jr. et al. |
| 6,679,382 | B1 | 1/2004 | Kancsar et al. |
| 6,681,149 | B2 | 1/2004 | William et al. |
| 6,692,211 | B2 | 2/2004 | Yuyama et al. |
| 6,697,704 | B2 | 2/2004 | Rosenblum |
| 6,702,150 | B2 | 3/2004 | Sumetzberger |
| 6,705,523 | B1 | 3/2004 | Stamm et al. |
| 6,711,460 | B1 | 3/2004 | Reese |
| 6,722,545 | B2 | 4/2004 | Yuyama et al. |
| 6,726,056 | B2 | 4/2004 | Yuyama et al. |
| 6,735,497 | B2 | 5/2004 | Wallace et al. |
| 6,736,286 | B2 | 5/2004 | Hashimoto et al. |
| 6,738,723 | B2 | 5/2004 | Hamilton |
| 6,739,476 | B2 | 5/2004 | Shigeyama et al. |
| 6,742,671 | B2 | 6/2004 | Hebron et al. |
| 6,755,931 | B2 | 6/2004 | Vollm et al. |
| 6,760,643 | B2 | 7/2004 | Lipps |
| 6,766,218 | B2 | 7/2004 | Rosenblum |
| 6,766,920 | B2 | 7/2004 | Yuyama et al. |
| 6,775,589 | B2 | 8/2004 | Williams |
| 6,775,591 | B1 | 8/2004 | Shoenfeld |
| 6,776,304 | B2 | 8/2004 | Liff et al. |
| 6,785,589 | B2 | 8/2004 | Eggenberger et al. |
| 6,789,996 | B2 | 9/2004 | Yuyama et al. |
| 6,790,198 | B1 | 9/2004 | White et al. |
| 6,793,077 | B2 | 9/2004 | Kancsar et al. |
| 6,814,219 | B2 | 11/2004 | Shimizu |
| 6,814,254 | B2 | 11/2004 | Liff et al. |
| 6,814,255 | B2 | 11/2004 | Liff et al. |
| 6,830,161 | B2 | 12/2004 | Yuyama et al. |
| 6,843,357 | B2 | 1/2005 | Bybee et al. |
| 6,847,861 | B2 | 1/2005 | Lunak et al. |
| 6,848,593 | B2 | 2/2005 | Papp |

(56) References Cited

U.S. PATENT DOCUMENTS

| | | |
|---|---|---|
| 6,874,684 B1 | 4/2005 | Denenberg et al. |
| 6,892,780 B2 | 5/2005 | Vollm et al. |
| 6,892,941 B2 | 5/2005 | Rosenblum |
| 6,895,304 B2 | 5/2005 | Spano, Jr. et al. |
| 6,905,046 B2 | 6/2005 | Coughlin et al. |
| 6,910,601 B2 | 6/2005 | Thomas et al. |
| 6,963,791 B1 | 11/2005 | Frederick et al. |
| 6,971,522 B2 | 12/2005 | Yuyama et al. |
| 6,971,541 B2 | 12/2005 | Williams et al. |
| 6,971,544 B2 | 12/2005 | Williams et al. |
| 6,974,049 B2 | 12/2005 | Williams et al. |
| 6,974,050 B2 | 12/2005 | Williams et al. |
| 6,975,922 B2 | 12/2005 | Duncan et al. |
| 6,981,609 B2 | 1/2006 | Yuyama et al. |
| 6,985,797 B2 | 1/2006 | Spano, Jr. et al. |
| 6,994,249 B2 | 2/2006 | Peterka et al. |
| 6,996,455 B2 | 2/2006 | Eggenberger et al. |
| 6,997,320 B1 | 2/2006 | Kancsar et al. |
| 7,006,893 B2 | 2/2006 | Hart et al. |
| 7,006,894 B2 | 2/2006 | de la Huerga |
| 7,010,389 B2 | 3/2006 | Lunak et al. |
| 7,014,063 B2 | 3/2006 | Shows et al. |
| 7,016,766 B2 | 3/2006 | William et al. |
| 7,017,623 B2 | 3/2006 | Tribble et al. |
| 7,040,070 B2 | 5/2006 | Yuyama et al. |
| 7,040,077 B2 | 5/2006 | Yasuoka et al. |
| 7,040,504 B2 | 5/2006 | Broadfield et al. |
| 7,040,505 B2 | 5/2006 | Hashimoto et al. |
| 7,048,142 B1 | 5/2006 | Michael et al. |
| 7,052,097 B2 | 5/2006 | Meek, Jr. et al. |
| 7,059,098 B2 | 6/2006 | Kim |
| 7,059,526 B1 | 6/2006 | Sullivan et al. |
| 7,066,291 B2 | 6/2006 | Martin et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,725 B2 | 9/2006 | Thorne |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,117,902 B2 | 10/2006 | Osborne |
| 7,118,006 B2 | 10/2006 | Williams et al. |
| 7,121,397 B2 | 10/2006 | Yuyama et al. |
| 7,122,005 B2 | 10/2006 | Shusterman |
| 7,123,989 B2 | 10/2006 | Pinney et al. |
| 7,129,490 B2 | 10/2006 | Olson et al. |
| 7,133,639 B2 | 11/2006 | Yuyama et al. |
| 7,139,639 B2 | 11/2006 | Broussard et al. |
| 7,140,542 B2 | 11/2006 | Andreasson et al. |
| 7,140,810 B1 | 11/2006 | Christian et al. |
| 7,146,247 B2 | 12/2006 | Kirsch et al. |
| 7,150,724 B2 | 12/2006 | Morris et al. |
| 7,151,982 B2 | 12/2006 | Liff et al. |
| 7,155,306 B2 | 12/2006 | Haitin et al. |
| 7,171,277 B2 | 1/2007 | Engleson et al. |
| 7,177,721 B2 | 2/2007 | Kirsch et al. |
| 7,182,105 B1 | 2/2007 | Feehan et al. |
| 7,182,256 B2 | 2/2007 | Andreasson et al. |
| 7,203,571 B2 | 4/2007 | Kirsch et al. |
| 7,210,598 B2 | 5/2007 | Gerold et al. |
| 7,218,231 B2 | 5/2007 | Higham |
| 7,220,082 B1 | 5/2007 | Christian et al. |
| 7,225,597 B1 | 6/2007 | Knoth |
| 7,228,198 B2 | 6/2007 | Vollm et al. |
| 7,234,002 B2 | 7/2007 | Hoganson et al. |
| 7,240,699 B2 | 7/2007 | Osborne et al. |
| 7,249,688 B2 | 7/2007 | Hunter et al. |
| 7,258,249 B1 | 8/2007 | Frederick et al. |
| 7,262,698 B1 | 8/2007 | Frederick et al. |
| 7,263,410 B1 | 8/2007 | Frederick et al. |
| 7,269,476 B2 | 9/2007 | Ratnakar |
| 7,269,480 B2 | 9/2007 | Hashimoto et al. |
| 7,275,353 B2 | 10/2007 | Williams et al. |
| 7,286,900 B1 | 10/2007 | Frederick et al. |
| 7,289,879 B2 | 10/2007 | William et al. |
| 7,293,672 B2 | 11/2007 | Mori et al. |
| 7,305,287 B2 | 12/2007 | Park |
| 7,311,222 B2 | 12/2007 | Shigeyama et al. |
| 7,314,339 B1 | 1/2008 | Christian et al. |
| 7,316,328 B2 | 1/2008 | Yuyama et al. |
| 7,326,005 B1 | 2/2008 | Castro et al. |
| 7,328,084 B1 | 2/2008 | Hoganson et al. |
| 7,343,943 B2 | 3/2008 | Khan et al. |
| 7,344,047 B2 | 3/2008 | Gilmore |
| 7,344,049 B2 | 3/2008 | Daniels et al. |
| 7,347,341 B2 | 3/2008 | Burggraf |
| 7,348,884 B2 | 3/2008 | Higham |
| 7,350,667 B2 | 4/2008 | Yuyama |
| 7,360,668 B2 | 4/2008 | Yuyama et al. |
| 7,363,106 B1 | 4/2008 | Hoganson et al. |
| 7,383,674 B2 | 6/2008 | Van Eenoo |
| 7,395,946 B2 | 7/2008 | Yuyama et al. |
| 7,412,302 B2 | 8/2008 | Cobb et al. |
| 7,412,809 B2 | 8/2008 | Yuyama et al. |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,427,002 B2 | 9/2008 | Liff et al. |
| 7,428,805 B2 | 9/2008 | Kim |
| 7,428,806 B2 | 9/2008 | Kim |
| 7,429,127 B2 | 9/2008 | Walker et al. |
| 7,431,115 B2 | 10/2008 | Thorne |
| 7,434,704 B2 | 10/2008 | Yuyama et al. |
| 7,440,817 B2 | 10/2008 | Fu |
| 7,444,203 B2 | 10/2008 | Rosenblum |
| 7,457,685 B2 | 11/2008 | D'Silva |
| 7,463,947 B1 | 12/2008 | Frederick et al. |
| 7,467,503 B2 | 12/2008 | Davolio et al. |
| 7,469,820 B2 | 12/2008 | Rosenblum |
| 7,471,993 B2 | 12/2008 | Rosenblum |
| 7,474,945 B2 | 1/2009 | Matsunaga |
| 7,500,337 B2 | 3/2009 | Yuyama et al. |
| 7,502,666 B2 | 3/2009 | Siegel et al. |
| 7,506,780 B2 | 3/2009 | Hutchinson et al. |
| 7,515,988 B1 | 4/2009 | Frederick et al. |
| 7,518,516 B2 | 4/2009 | Azevedo et al. |
| 7,530,211 B2 | 5/2009 | McErlean et al. |
| 7,532,948 B2 | 5/2009 | Vollm et al. |
| 7,536,938 B2 | 5/2009 | Kim |
| 7,540,222 B2 | 6/2009 | Kim |
| 7,549,266 B2 | 6/2009 | Yuyama et al. |
| 7,554,449 B2 | 6/2009 | Higham |
| 7,555,875 B2 | 7/2009 | Kim |
| 7,562,791 B2 | 7/2009 | Yuyama et al. |
| 7,565,782 B2 | 7/2009 | Williams et al. |
| 7,565,784 B2 | 7/2009 | Williams et al. |
| 7,568,627 B2 | 8/2009 | Lunak et al. |
| 7,571,024 B2 | 8/2009 | Duncan et al. |
| 7,578,383 B2 | 8/2009 | Itoh |
| 7,588,167 B2 | 9/2009 | Hunter et al. |
| 7,596,426 B2 | 9/2009 | McGrady et al. |
| 7,596,427 B1 | 9/2009 | Frederick et al. |
| 7,596,925 B2 | 10/2009 | Yuyama et al. |
| 7,603,197 B2 | 10/2009 | Yuyama et al. |
| 7,606,723 B2 | 10/2009 | Mayaud |
| 7,610,115 B2 | 10/2009 | Rob et al. |
| 7,624,894 B2 | 12/2009 | Gerold et al. |
| 7,630,788 B1 | 12/2009 | Reese |
| 7,630,789 B1 | 12/2009 | Broadfield et al. |
| 7,630,790 B2 | 12/2009 | Handfield et al. |
| 7,630,791 B2 | 12/2009 | Nguyen et al. |
| 7,637,079 B2 | 12/2009 | Klingel et al. |
| 7,639,136 B1 | 12/2009 | Wass et al. |
| 7,650,298 B2 | 1/2010 | Godlewski |
| 7,650,732 B2 | 1/2010 | Pearson et al. |
| 7,651,310 B2 | 1/2010 | Gambarelli et al. |
| 7,654,261 B1 | 2/2010 | Rockhold |
| 7,668,998 B2 | 2/2010 | Perisich et al. |
| 7,673,771 B2 | 3/2010 | Bedore et al. |
| 7,673,772 B2 | 3/2010 | Bedore et al. |
| 7,675,421 B2 | 3/2010 | Higham |

(56) References Cited

U.S. PATENT DOCUMENTS

| | | |
|---|---|---|
| 7,676,299 B2 | 3/2010 | Clarke et al. |
| 7,676,382 B2 | 3/2010 | Silverbrook et al. |
| 7,681,606 B2 | 3/2010 | Khan et al. |
| 7,685,004 B2 | 3/2010 | Moncrief et al. |
| 7,686,184 B2 | 3/2010 | Yuyama et al. |
| 7,689,316 B1 | 3/2010 | Frederick et al. |
| 7,689,317 B2 | 3/2010 | McGrady et al. |
| 7,689,318 B2 | 3/2010 | Draper |
| 7,694,846 B2 | 4/2010 | Yuyama et al. |
| 7,698,019 B2 | 4/2010 | Moncrief et al. |
| 7,703,637 B2 | 4/2010 | Michelli |
| 7,706,915 B2 | 4/2010 | Mohapatra et al. |
| 7,711,449 B2 | 5/2010 | Abdulhay et al. |
| 7,719,420 B2 | 5/2010 | Christie et al. |
| 7,721,508 B2 | 5/2010 | Yuyama et al. |
| 7,721,512 B2 | 5/2010 | Siegel et al. |
| 7,726,095 B2 | 6/2010 | Yuyama et al. |
| 7,726,100 B2 | 6/2010 | Bigoni |
| 7,731,473 B2 | 6/2010 | Yuyama et al. |
| 7,735,683 B2 | 6/2010 | Handfield et al. |
| 7,735,732 B2 | 6/2010 | Linton et al. |
| 7,737,858 B2 | 6/2010 | Matityaho |
| 7,742,840 B2 | 6/2010 | Watabe et al. |
| 7,743,943 B2 | 6/2010 | Williams et al. |
| 7,747,345 B2 | 6/2010 | Ohmura et al. |
| 7,748,628 B2 | 7/2010 | Greyshock |
| 7,751,930 B2 | 7/2010 | Valerino, Sr. |
| 7,753,229 B2 | 7/2010 | Hutchinson et al. |
| 7,766,242 B2 | 8/2010 | Lunak et al. |
| 7,768,378 B2 | 8/2010 | Hill et al. |
| 7,770,357 B2 | 8/2010 | Yuyama et al. |
| 7,774,097 B2 | 8/2010 | Rosenblum |
| 7,775,056 B2 | 8/2010 | Lowenstein |
| 7,775,756 B2 | 8/2010 | Koike et al. |
| 7,783,378 B2 | 8/2010 | Pinney et al. |
| 7,783,383 B2 | 8/2010 | Eliuk et al. |
| 7,787,986 B2 | 8/2010 | Pinney et al. |
| 7,789,267 B2 | 9/2010 | Hutchinson et al. |
| 7,793,836 B2 | 9/2010 | Radatti et al. |
| 7,805,217 B2 | 9/2010 | Chudy et al. |
| 7,806,488 B2 | 10/2010 | Hannan et al. |
| 7,806,644 B2 | 10/2010 | Yuyama et al. |
| 7,813,939 B2 | 10/2010 | Clements et al. |
| 7,822,505 B2 | 10/2010 | Yuyama et al. |
| 7,822,508 B2 | 10/2010 | Sugiyama et al. |
| 7,823,748 B2 | 11/2010 | Yuyama et al. |
| 7,827,764 B2 | 11/2010 | Yuyama et al. |
| 7,828,149 B2 | 11/2010 | Kalvelage et al. |
| 7,831,334 B2 | 11/2010 | Vollm et al. |
| 7,831,336 B2 | 11/2010 | Gumpert |
| 7,835,819 B2 | 11/2010 | Duncan et al. |
| 7,837,107 B1 | 11/2010 | Leu et al. |
| 7,840,307 B2 | 11/2010 | Mauger et al. |
| 7,844,362 B2 | 11/2010 | Handfield et al. |
| 7,844,470 B2 | 11/2010 | Portnoy et al. |
| 7,845,144 B2 | 12/2010 | Yuyama |
| 7,845,285 B2 | 12/2010 | Hast |
| 7,847,970 B1 | 12/2010 | McGrady |
| 7,853,355 B1 | 12/2010 | Willemse et al. |
| 7,857,163 B2 | 12/2010 | Shigeyama et al. |
| 7,860,603 B2 | 12/2010 | Handfield et al. |
| 7,861,491 B2 | 1/2011 | Yuyama et al. |
| 7,861,492 B2 | 1/2011 | Yuyama et al. |
| 7,861,495 B2 | 1/2011 | Yuyama et al. |
| 7,864,041 B2 | 1/2011 | Godlewski |
| 7,865,263 B2 | 1/2011 | Spano, Jr. et al. |
| 7,866,506 B2 | 1/2011 | Daniels et al. |
| 7,871,234 B2 | 1/2011 | Yuyama et al. |
| 7,873,435 B2 | 1/2011 | Yuyama et al. |
| 7,882,680 B2 | 2/2011 | Siegel et al. |
| 7,886,508 B2 | 2/2011 | Yuyama et al. |
| 7,894,656 B2 | 2/2011 | Kim |
| 7,894,939 B2 | 2/2011 | Zini et al. |
| 7,905,372 B2 | 3/2011 | Williams et al. |
| 7,912,578 B1 | 3/2011 | Frankel |
| 7,912,582 B1 | 3/2011 | Holtje et al. |
| 7,917,246 B2 | 3/2011 | Handfield et al. |
| 7,918,068 B2 | 4/2011 | Kumano |
| 7,930,060 B2 | 4/2011 | Yuyama et al. |
| 7,930,064 B2 | 4/2011 | Popovich, Jr. et al. |
| 7,930,066 B2 | 4/2011 | Eliuk et al. |
| 7,933,683 B2 | 4/2011 | Asaoka et al. |
| 7,933,684 B2 | 4/2011 | Sugino et al. |
| 7,934,356 B2 | 5/2011 | Yuyama et al. |
| 7,939,561 B2 | 5/2011 | Schellenger et al. |
| 7,945,455 B2 | 5/2011 | Zimmermann |
| 7,950,202 B2 | 5/2011 | Kodama et al. |
| 7,950,206 B2 | 5/2011 | Knoth |
| 7,950,879 B2 | 5/2011 | Hoganson et al. |
| 7,953,515 B2 | 5/2011 | Hoganson et al. |
| 7,957,929 B2 | 6/2011 | Yuyama et al. |
| 7,958,701 B2 | 6/2011 | Knoth |
| 7,963,089 B2 | 6/2011 | Nelson et al. |
| 7,991,507 B2 | 8/2011 | Liff et al. |
| 7,994,897 B2 | 8/2011 | Azevedo et al. |
| 7,996,105 B2 | 8/2011 | Handfield et al. |
| 7,996,109 B2 | 8/2011 | Zini et al. |
| 8,000,836 B2 | 8/2011 | Pinney et al. |
| 8,005,688 B2 | 8/2011 | Coffman et al. |
| 8,006,903 B2 | 8/2011 | Braun et al. |
| 8,009,040 B2 | 8/2011 | Kennedy |
| 8,009,913 B2 | 8/2011 | Greyshock |
| 8,010,230 B2 | 8/2011 | Zini et al. |
| RE42,730 E | 9/2011 | Lasher et al. |
| 8,011,395 B2 | 9/2011 | Yuyama |
| 8,016,095 B2 | 9/2011 | Daniels et al. |
| 8,020,356 B2 | 9/2011 | Yuyama et al. |
| 8,020,725 B2 | 9/2011 | Yuyama et al. |
| 8,025,228 B2 | 9/2011 | Dearing et al. |
| 8,027,748 B2 | 9/2011 | Handfield et al. |
| 8,027,749 B2 | 9/2011 | Vahlberg et al. |
| RE42,766 E | 10/2011 | Lasher et al. |
| 8,028,822 B2 | 10/2011 | Braunstein |
| 8,028,835 B2 | 10/2011 | Yasuda et al. |
| 8,029,212 B2 | 10/2011 | Valerino, Sr. |
| 8,033,424 B2 | 10/2011 | Rosenblum |
| 8,036,773 B2 | 10/2011 | Braun et al. |
| 8,036,911 B2 | 10/2011 | Bellon et al. |
| 8,036,914 B1 | 10/2011 | Pinsonneault |
| 8,038,016 B2 | 10/2011 | Yuyama et al. |
| 8,041,102 B2 | 10/2011 | Yuyama et al. |
| 8,041,455 B2 | 10/2011 | Thorne |
| 8,042,738 B2 | 10/2011 | Cloix |
| RE42,937 E | 11/2011 | Lasher et al. |
| 8,047,352 B2 | 11/2011 | Yuyama |
| 8,050,941 B2 | 11/2011 | Hardaway |
| 8,054,086 B2 | 11/2011 | Rivenbark, Jr. |
| 8,060,248 B1 | 11/2011 | Boyer et al. |
| 8,065,035 B2 | 11/2011 | Ross et al. |
| 8,068,931 B2 | 11/2011 | Tran et al. |
| 8,069,993 B2 | 12/2011 | Yuyama et al. |
| 8,073,563 B2 | 12/2011 | Vahlberg et al. |
| 8,078,317 B2 | 12/2011 | Allinson et al. |
| 8,082,957 B2 | 12/2011 | Yuyama et al. |
| 8,090,472 B2 | 1/2012 | Schifman et al. |
| 8,090,473 B2 | 1/2012 | Higham |
| 8,094,028 B2 | 1/2012 | Braun et al. |
| 8,099,339 B1 | 1/2012 | Pinsonneault et al. |
| 8,099,928 B2 | 1/2012 | Yuyama |
| 8,103,379 B2 | 1/2012 | Biba et al. |
| 8,108,068 B1 | 1/2012 | Boucher et al. |
| 8,112,175 B2 | 2/2012 | Handfield et al. |
| 8,113,424 B2 | 2/2012 | Philippe |
| 8,113,425 B2 | 2/2012 | Dearing et al. |
| 8,113,849 B2 | 2/2012 | Park, IV |
| 8,116,906 B2 | 2/2012 | Valerino, Sr. |
| 8,117,809 B2 | 2/2012 | McErlean et al. |
| 8,126,590 B2 | 2/2012 | Vahlberg et al. |
| 8,131,397 B2 | 3/2012 | Vahlberg et al. |
| 8,136,332 B2 | 3/2012 | Rice et al. |
| 8,140,186 B2 | 3/2012 | Vahlberg et al. |
| 8,141,330 B2 | 3/2012 | Henkel |
| 8,145,353 B1 | 3/2012 | Cotner |
| 8,146,702 B2 | 4/2012 | Schendel et al. |

(56) References Cited

U.S. PATENT DOCUMENTS

| | | |
|---|---|---|
| 8,151,622 B2 | 4/2012 | Uebel et al. |
| 8,151,835 B2 | 4/2012 | Khan et al. |
| 8,155,786 B2 | 4/2012 | Vahlberg et al. |
| 8,157,125 B2 | 4/2012 | Schiff |
| 8,165,718 B2 | 4/2012 | Ota et al. |
| 8,165,929 B2 | 4/2012 | Chudy et al. |
| 8,167,008 B2 | 5/2012 | Taniguchi et al. |
| 8,170,714 B2 | 5/2012 | Spano, Jr. et al. |
| 8,170,927 B2 | 5/2012 | Godlewski |
| 8,180,485 B2 | 5/2012 | Reckelhoff |
| 8,185,236 B2 | 5/2012 | Kim |
| 8,195,329 B2 | 6/2012 | Pinney et al. |
| 8,196,774 B1 | 6/2012 | Clarke et al. |
| 8,204,621 B2 | 6/2012 | Imai et al. |
| 8,204,624 B2 | 6/2012 | Zini et al. |
| 8,204,761 B2 | 6/2012 | Monerief et al. |
| 8,209,193 B2 | 6/2012 | Moncrief et al. |
| 8,209,942 B2 | 7/2012 | Kodama et al. |
| 8,209,943 B2 | 7/2012 | Yuyama et al. |
| 8,217,655 B2 | 7/2012 | De Vries et al. |
| 8,219,243 B2 | 7/2012 | Haas |
| 8,219,413 B2 | 7/2012 | Martinez et al. |
| 8,224,482 B2 | 7/2012 | Schedel et al. |
| 8,224,664 B1 | 7/2012 | Louie et al. |
| 8,225,582 B2 | 7/2012 | Siegel et al. |
| 8,231,749 B2 | 7/2012 | Dent et al. |
| 8,234,008 B2 | 7/2012 | Weber |
| 8,239,062 B2 | 8/2012 | Vahlberg et al. |
| 8,245,483 B2 | 8/2012 | Yuyama et al. |
| 8,251,629 B2 | 8/2012 | Schifman et al. |
| 8,256,187 B2 | 9/2012 | Yuyama et al. |
| 8,258,961 B2 | 9/2012 | Phillips et al. |
| 8,260,632 B2 | 9/2012 | Moncrief et al. |
| 8,267,622 B1 | 9/2012 | MacLean-Blevins et al. |
| 8,269,613 B2 | 9/2012 | Lazar |
| 8,271,624 B2 | 9/2012 | Owen |
| 8,272,194 B2 | 9/2012 | Nelson |
| 8,274,363 B2 | 9/2012 | Goza |
| 8,280,549 B2 | 10/2012 | Liff et al. |
| 8,280,550 B2 | 10/2012 | Levy et al. |
| 8,281,553 B2 | 10/2012 | Kim |
| 8,284,059 B2 | 10/2012 | Ross |
| 8,292,173 B2 | 10/2012 | Yturralde et al. |
| 8,295,977 B2 | 10/2012 | Yuyama et al. |
| 8,308,414 B2 | 11/2012 | Schifman et al. |
| 8,317,432 B2 | 11/2012 | Castro et al. |
| 8,319,613 B2 | 11/2012 | Lazar |
| 8,321,050 B2 | 11/2012 | Rivenbark, Jr. et al. |
| 8,322,601 B1 | 12/2012 | Benore et al. |
| 8,334,751 B2 | 12/2012 | Azevedo et al. |
| 8,335,588 B2 | 12/2012 | Rahilly et al. |
| 8,339,261 B1 | 12/2012 | Wolski |
| 8,341,041 B2 | 12/2012 | Hull |
| 8,342,331 B2 | 1/2013 | Ziemba et al. |
| 8,355,929 B2 | 1/2013 | Kienle et al. |
| 8,360,271 B2 | 1/2013 | Omura et al. |
| 8,365,507 B2 | 2/2013 | Klingel |
| 8,365,950 B2 | 2/2013 | Yuyama et al. |
| 8,374,965 B2 | 2/2013 | Friend et al. |
| 8,380,535 B2 | 2/2013 | Deneberg et al. |
| 8,386,070 B2 | 2/2013 | Eliuk et al. |
| 8,386,275 B2 | 2/2013 | Chambers |
| 8,387,343 B2 | 3/2013 | Yasunaga et al. |
| 8,393,495 B2 | 3/2013 | Kim |
| 8,403,010 B2 | 3/2013 | Taniguchi et al. |
| RE44,127 E | 4/2013 | Moncrief et al. |
| 8,412,375 B2 | 4/2013 | Schifman et al. |
| 8,417,379 B2 | 4/2013 | Chudy et al. |
| 2002/0042725 A1 | 4/2002 | Mayaud |
| 2003/0009154 A1 | 1/2003 | Whitman |
| 2003/0103839 A1 | 6/2003 | Osborne et al. |
| 2004/0059463 A1 | 3/2004 | Coughlin |
| 2004/0089577 A1 | 5/2004 | Kancsar et al. |
| 2004/0104142 A1 | 6/2004 | Dobler et al. |
| 2004/0107022 A1 | 6/2004 | Gomez |
| 2004/0154955 A1 | 8/2004 | Friar et al. |
| 2004/0158349 A1 | 8/2004 | Bonney et al. |
| 2004/0172169 A1 | 9/2004 | Wright et al. |
| 2004/0182044 A1 | 9/2004 | Kim |
| 2004/0189158 A1 | 9/2004 | Zahari |
| 2004/0210488 A1 | 10/2004 | Doherty |
| 2004/0230502 A1 | 11/2004 | Fiacco et al. |
| 2005/0004700 A1 | 1/2005 | DiMaggio |
| 2005/0021175 A1 | 1/2005 | Bain |
| 2005/0049746 A1 | 3/2005 | Rosenblum |
| 2005/0080651 A1 | 4/2005 | Morrison et al. |
| 2005/0119604 A1 | 6/2005 | Bonney et al. |
| 2005/0131733 A1 | 6/2005 | Lubow |
| 2005/0162979 A1 | 7/2005 | Ostergaard et al. |
| 2005/0183981 A1 | 8/2005 | Gelardi |
| 2005/0240305 A1 | 10/2005 | Bogash et al. |
| 2005/0249819 A1 | 11/2005 | Hinnen et al. |
| 2005/0261940 A1 | 11/2005 | Gay et al. |
| 2005/0269236 A1 | 12/2005 | Rohrmus et al. |
| 2005/0283259 A1 | 12/2005 | Wolpow |
| 2006/0010009 A1 | 1/2006 | Fangman |
| 2006/0040076 A1 | 2/2006 | Franzyshen et al. |
| 2006/0042988 A1 | 3/2006 | Hjalmarsson |
| 2006/0049078 A1 | 3/2006 | Sams et al. |
| 2006/0064212 A1 | 3/2006 | Thorne |
| 2006/0079994 A1 | 4/2006 | Chu et al. |
| 2006/0089856 A1 | 4/2006 | Kadhiresan |
| 2006/0089858 A1 | 4/2006 | Ling |
| 2006/0096656 A1 | 5/2006 | Stueckle |
| 2006/0125356 A1 | 6/2006 | Meek et al. |
| 2006/0149587 A1 | 7/2006 | Hill et al. |
| 2006/0180600 A1 | 8/2006 | Talyor |
| 2006/0184271 A1 | 8/2006 | Loveless |
| 2006/0190297 A1 | 8/2006 | Glass et al. |
| 2006/0215495 A1 | 9/2006 | Soled et al. |
| 2006/0226957 A1 | 10/2006 | Miller et al. |
| 2006/0228203 A1 | 10/2006 | Baumle et al. |
| 2006/0253346 A1 | 11/2006 | Gomez |
| 2007/0012712 A1 | 1/2007 | Syiau |
| 2007/0023512 A1 | 2/2007 | Miller et al. |
| 2007/0051072 A1 | 3/2007 | Lai |
| 2007/0102109 A1 | 5/2007 | Katritzky et al. |
| 2007/0145130 A1 | 6/2007 | Danilewitz |
| 2007/0156452 A1 | 7/2007 | Batch |
| 2007/0185615 A1* | 8/2007 | Bossi ................. G06F 19/3462 700/244 |
| 2007/0185617 A1 | 8/2007 | Kim |
| 2007/0218322 A1 | 9/2007 | Wullschleger |
| 2007/0219667 A1 | 9/2007 | Jung et al. |
| 2007/0233567 A1 | 10/2007 | Daly |
| 2007/0262147 A1* | 11/2007 | Braun ..................... G06K 7/14 235/454 |
| 2007/0290030 A1 | 12/2007 | Fox et al. |
| 2007/0293983 A1 | 12/2007 | Butler |
| 2007/0296598 A1 | 12/2007 | Kim |
| 2008/0054007 A1 | 3/2008 | Mador |
| 2008/0056556 A1 | 3/2008 | Eller et al. |
| 2008/0061071 A1 | 3/2008 | Omura et al. |
| 2008/0065264 A1 | 3/2008 | Omura et al. |
| 2008/0065418 A1 | 3/2008 | Byrom et al. |
| 2008/0071648 A1 | 3/2008 | Kim |
| 2008/0190801 A1 | 4/2008 | Kwok |
| 2008/0103821 A1 | 5/2008 | Cerbone et al. |
| 2008/0110130 A1 | 5/2008 | Kim |
| 2008/0110134 A1 | 5/2008 | Nitulescu et al. |
| 2008/0110791 A1 | 5/2008 | Specker |
| 2008/0120207 A1 | 5/2008 | Strickland |
| 2008/0147518 A1 | 6/2008 | Haider et al. |
| 2008/0155718 A1 | 6/2008 | Kim |
| 2008/0179387 A1 | 7/2008 | Cantlay et al. |
| 2008/0191013 A1 | 8/2008 | Liberatore |
| 2008/0201171 A1 | 8/2008 | Brushwood |
| 2008/0251411 A1 | 10/2008 | Walker et al. |
| 2008/0264962 A1 | 10/2008 | Schifman et al. |
| 2008/0264967 A1 | 10/2008 | Schifman et al. |
| 2008/0270178 A1 | 10/2008 | McRae et al. |
| 2008/0306740 A1 | 12/2008 | Schuck et al. |
| 2008/0316045 A1 | 12/2008 | Sriharto et al. |
| 2009/0012818 A1 | 1/2009 | Rodgers |

(56) References Cited

U.S. PATENT DOCUMENTS

| | | |
|---|---|---|
| 2009/0012820 A1 | 1/2009 | Bishop et al. |
| 2009/0013899 A1 | 1/2009 | Wolf et al. |
| 2009/0014458 A1 | 1/2009 | Heffron |
| 2009/0021345 A1 | 1/2009 | Sriharto et al. |
| 2009/0024248 A1 | 1/2009 | Hodson |
| 2009/0037020 A1 | 2/2009 | Brown |
| 2009/0038982 A1 | 2/2009 | Doucet et al. |
| 2009/0043421 A1 | 2/2009 | Parrish et al. |
| 2009/0071863 A1 | 3/2009 | Arnold et al. |
| 2009/0082879 A1 | 3/2009 | Dooley et al. |
| 2009/0105876 A1 | 4/2009 | Simpson et al. |
| 2009/0107873 A1 | 4/2009 | Cotton et al. |
| 2009/0108011 A1 | 4/2009 | Heffron |
| 2009/0108016 A1 | 4/2009 | Brown et al. |
| 2009/0125324 A1 | 5/2009 | Keravich et al. |
| 2009/0134181 A1 | 5/2009 | Wachman et al. |
| 2009/0138122 A1* | 5/2009 | Wagner ............... A61G 12/001 700/226 |
| 2009/0167500 A1 | 7/2009 | Braun et al. |
| 2009/0169138 A1 | 7/2009 | Bieganski |
| 2009/0182582 A1 | 7/2009 | Hammon |
| 2009/0184128 A1 | 7/2009 | Kim |
| 2009/0188935 A1 | 7/2009 | Coughlin et al. |
| 2009/0194434 A1 | 8/2009 | Ellis et al. |
| 2009/0198208 A1 | 8/2009 | Stavsky et al. |
| 2009/0223990 A1 | 9/2009 | Bailey et al. |
| 2009/0223994 A1 | 9/2009 | Getz |
| 2009/0240528 A1 | 9/2009 | Bluth |
| 2009/0248196 A1 | 10/2009 | Davolio et al. |
| 2009/0254214 A1 | 10/2009 | Kudera et al. |
| 2009/0259486 A1 | 10/2009 | Burg et al. |
| 2009/0272081 A1 | 11/2009 | Panson et al. |
| 2009/0281657 A1 | 11/2009 | Gak et al. |
| 2009/0287350 A1 | 11/2009 | Johnson et al. |
| 2009/0287992 A1 | 11/2009 | Bresolin et al. |
| 2009/0315287 A1 | 12/2009 | Rossini |
| 2009/0326713 A1 | 12/2009 | Moriya |
| 2009/0326975 A1 | 12/2009 | Hardaway et al. |
| 2010/0010666 A1 | 1/2010 | Adams |
| 2010/0017296 A1 | 1/2010 | Spignesi, Jr. et al. |
| 2010/0036678 A1* | 2/2010 | Bray ................... G06F 19/3456 705/3 |
| 2010/0057250 A1 | 3/2010 | Lim et al. |
| 2010/0072104 A1 | 3/2010 | Kohl |
| 2010/0076595 A1 | 3/2010 | Nguyen |
| 2010/0094451 A1 | 4/2010 | Hoganson et al. |
| 2010/0096293 A1 | 4/2010 | Liebermann |
| 2010/0100391 A1 | 4/2010 | Daya |
| 2010/0114367 A1 | 5/2010 | Barrett et al. |
| 2010/0114605 A1 | 5/2010 | Aull et al. |
| 2010/0147868 A1 | 6/2010 | Yuyama et al. |
| 2010/0153129 A1 | 6/2010 | Luciano, Jr. et al. |
| 2010/0154928 A1 | 6/2010 | Taniguchi et al. |
| 2010/0168904 A1 | 7/2010 | Henderson et al. |
| 2010/0172724 A1 | 7/2010 | Hawkes et al. |
| 2010/0175352 A1 | 7/2010 | Soloman |
| 2010/0176146 A1 | 7/2010 | Ben-Dor |
| 2010/0183409 A1 | 7/2010 | Checketts et al. |
| 2010/0185458 A1 | 7/2010 | Newcomb et al. |
| 2010/0187243 A1 | 7/2010 | Layer et al. |
| 2010/0198401 A1 | 8/2010 | Waugh et al. |
| 2010/0198620 A1 | 8/2010 | Mullenger et al. |
| 2010/0228392 A1 | 9/2010 | Braun |
| 2010/0228566 A1 | 9/2010 | Taylor et al. |
| 2010/0239169 A1 | 9/2010 | Braun et al. |
| 2010/0247251 A1 | 9/2010 | Cornelius |
| 2010/0256800 A1 | 10/2010 | Heffron |
| 2010/0256808 A1 | 10/2010 | Hui |
| 2010/0268380 A1 | 10/2010 | Waugh et al. |
| 2010/0286816 A1 | 11/2010 | Dillon |
| 2010/0314282 A1 | 12/2010 | Bowers |
| 2010/0318218 A1 | 12/2010 | Muncy, Jr. et al. |
| 2010/0324936 A1 | 12/2010 | Vishnubhatla et al. |
| 2011/0008527 A1 | 1/2011 | Teggatz et al. |
| 2011/0010033 A1 | 1/2011 | Asahara et al. |
| 2011/0010196 A1 | 1/2011 | Nee et al. |
| 2011/0017764 A1 | 1/2011 | Liguori et al. |
| 2011/0029327 A1 | 2/2011 | Dunlop |
| 2011/0030034 A1 | 2/2011 | Ross |
| 2011/0035047 A1 | 2/2011 | Wagner |
| 2011/0037565 A1 | 2/2011 | Skirble et al. |
| 2011/0074576 A1 | 3/2011 | Ross |
| 2011/0077771 A1 | 3/2011 | Greyshock et al. |
| 2011/0112682 A1 | 5/2011 | Matsukawa et al. |
| 2011/0115620 A1 | 5/2011 | Myers |
| 2011/0132163 A1 | 6/2011 | Deutsch et al. |
| 2011/0146835 A1 | 6/2011 | Terzini |
| 2011/0160948 A1 | 6/2011 | Bailey et al. |
| 2011/0168733 A1 | 7/2011 | Yuyama et al. |
| 2011/0173926 A1 | 7/2011 | Yuyama et al. |
| 2011/0178634 A1 | 7/2011 | Yuyama et al. |
| 2011/0184751 A1 | 7/2011 | Holmes |
| 2011/0196563 A1 | 8/2011 | Yturralde et al. |
| 2011/0202171 A1 | 8/2011 | Rosenbaum |
| 2011/0204088 A1 | 8/2011 | Luchinger |
| 2011/0215022 A1 | 9/2011 | Sack et al. |
| 2011/0231012 A1 | 9/2011 | Sprague et al. |
| 2011/0232435 A1 | 9/2011 | Jaynes |
| 2011/0232447 A1 | 9/2011 | Jaynes |
| 2011/0234419 A1 | 9/2011 | Churbock et al. |
| 2011/0245963 A1 | 10/2011 | Leng |
| 2011/0245969 A1 | 10/2011 | Monto et al. |
| 2011/0246221 A1 | 10/2011 | Camp et al. |
| 2011/0251850 A1 | 10/2011 | Stephens |
| 2011/0252750 A1 | 10/2011 | Koike et al. |
| 2011/0257991 A1 | 10/2011 | Shukla |
| 2011/0266929 A1 | 11/2011 | Michael |
| 2011/0272428 A1 | 11/2011 | Ziemba et al. |
| 2011/0277420 A1 | 11/2011 | Peters et al. |
| 2011/0282489 A1 | 11/2011 | Buisman et al. |
| 2011/0286808 A1 | 11/2011 | Castro |
| 2011/0288883 A1 | 11/2011 | Knoth |
| 2011/0303692 A1 | 12/2011 | Kim |
| 2011/0305545 A1 | 12/2011 | Davis et al. |
| 2012/0001529 A1 | 1/2012 | Rahilly et al. |
| 2012/0004764 A1 | 1/2012 | Rahilly et al. |
| 2012/0004770 A1 | 1/2012 | Ooyen et al. |
| 2012/0012606 A1 | 1/2012 | Longley et al. |
| 2012/0029692 A1 | 2/2012 | Owen |
| 2012/0031043 A1 | 2/2012 | Yuyama et al. |
| 2012/0041778 A1 | 2/2012 | Kraft |
| 2012/0042609 A1 | 2/2012 | Inoue et al. |
| 2012/0044054 A1 | 2/2012 | Hussain et al. |
| 2012/0047049 A1 | 2/2012 | Cadiz |
| 2012/0051848 A1 | 3/2012 | Barrios |
| 2012/0051849 A1 | 3/2012 | Barrios |
| 2012/0055579 A1 | 3/2012 | Nufer et al. |
| 2012/0056000 A1 | 3/2012 | Shores |
| 2012/0075061 A1 | 3/2012 | Barnes |
| 2012/0089540 A1 | 4/2012 | Manivilovski et al. |
| 2012/0121132 A1 | 5/2012 | Asahara et al. |
| 2012/0130534 A1 | 5/2012 | Wurm |
| 2012/0152795 A1 | 6/2012 | Leon Alonso et al. |
| 2012/0154120 A1 | 6/2012 | Alloro et al. |
| 2012/0158235 A1 | 6/2012 | Jaynes |
| 2012/0168331 A1 | 7/2012 | Tagger |
| 2012/0173391 A1 | 7/2012 | Korhnak et al. |
| 2012/0175380 A1 | 7/2012 | Nishimura et al. |
| 2012/0176245 A1 | 7/2012 | Paydar et al. |
| 2012/0201434 A1 | 8/2012 | Natali et al. |
| 2012/0205441 A1 | 8/2012 | Utech et al. |
| 2012/0209619 A1 | 8/2012 | Knotts et al. |
| 2012/0216485 A1 | 8/2012 | Amano et al. |
| 2012/0241043 A1 | 9/2012 | Perazzo et al. |
| 2012/0248005 A1 | 10/2012 | Bergey |
| 2012/0248134 A1 | 10/2012 | Santmyer et al. |
| 2012/0248947 A1 | 10/2012 | Kijowski et al. |
| 2012/0253509 A1 | 10/2012 | Garda et al. |
| 2012/0253510 A1 | 10/2012 | Thomas et al. |
| 2012/0259655 A1 | 10/2012 | Madreperla |
| 2012/0271454 A1 | 10/2012 | Gotou et al. |
| 2012/0283871 A1 | 11/2012 | Chai et al. |
| 2012/0304596 A1 | 12/2012 | Koike et al. |
| 2012/0323362 A1 | 12/2012 | Paydar et al. |

(56) References Cited

U.S. PATENT DOCUMENTS

| | | |
|---|---|---|
| 2012/0330460 A1 | 12/2012 | Henderson et al. |
| 2012/0330672 A1 | 12/2012 | Henderson et al. |
| 2013/0006415 A1 | 1/2013 | Paydar et al. |
| 2013/0006652 A1 | 1/2013 | Vahlherg et al. |
| 2013/0018356 A1 | 1/2013 | Prince et al. |
| 2013/0018503 A1 | 1/2013 | Carson et al. |
| 2013/0020345 A1 | 1/2013 | Kim |
| 2013/0026174 A1 | 1/2013 | Yuyama et al. |
| 2013/0027206 A1 | 1/2013 | Kosted |
| 2013/0032247 A1 | 2/2013 | Imai et al. |
| 2013/0049967 A1 | 2/2013 | Lee |
| 2013/0054014 A1* | 2/2013 | Kainoh ............... G07F 17/0092 700/235 |
| 2013/0066465 A1 | 3/2013 | Har-Noy |
| 2013/0070090 A1 | 3/2013 | Bufalini et al. |
| 2013/0079924 A1 | 3/2013 | Garda et al. |
| 2013/0079927 A1 | 3/2013 | Rahilly et al. |
| 2013/0081362 A1 | 4/2013 | Yuyama |
| 2013/0092700 A1 | 4/2013 | Braunstein |
| 2013/0153594 A1 | 6/2013 | Yuyama et al. |
| 2013/0168405 A1 | 7/2013 | Yuyama et al. |
| 2013/0212987 A1 | 8/2013 | Shigeyama et al. |
| 2013/0233934 A1 | 9/2013 | Schmidt et al. |
| 2013/0256097 A1 | 10/2013 | Koike et al. |
| 2014/0102860 A1 | 4/2014 | Greyshock et al. |
| 2014/0261058 A1 | 9/2014 | Henderson et al. |

FOREIGN PATENT DOCUMENTS

| | | |
|---|---|---|
| EP | 1 435 334 A1 | 7/2004 |
| EP | 1 443 447 A2 | 8/2004 |
| EP | 1 449 143 A1 | 8/2004 |
| EP | 1 461 282 A1 | 9/2004 |
| EP | 1 484 914 A1 | 12/2004 |
| EP | 1 496 481 A2 | 1/2005 |
| EP | 1 531 410 A1 | 5/2005 |
| EP | 1 548 624 A1 | 6/2005 |
| EP | 1 560 756 A1 | 8/2005 |
| EP | 1 562 840 A2 | 8/2005 |
| EP | 1 586 046 A2 | 10/2005 |
| EP | 1 598 291 A2 | 11/2005 |
| EP | 1 620 593 A1 | 12/2005 |
| EP | 1 610 749 A1 | 1/2006 |
| EP | 1 620 319 A1 | 2/2006 |
| EP | 1 620 346 A2 | 2/2006 |
| EP | 1 674 408 A1 | 6/2006 |
| EP | 1 747 998 A1 | 1/2007 |
| EP | 1 748 917 A1 | 2/2007 |
| EP | 1 762 969 A2 | 3/2007 |
| EP | 1 775 224 A1 | 4/2007 |
| EP | 1 794 063 A1 | 6/2007 |
| EP | 1 850 826 A1 | 7/2007 |
| EP | 1 864 907 A2 | 12/2007 |
| EP | 1 908 701 A2 | 4/2008 |
| EP | 1 941 886 A1 | 7/2008 |
| EP | 1 945 532 A1 | 7/2008 |
| EP | 1 965 325 A1 | 9/2008 |
| EP | 1 974 303 A2 | 10/2008 |
| EP | 1 979 244 A2 | 10/2008 |
| EP | 2 000 424 A2 | 12/2008 |
| EP | 2 009 793 A1 | 12/2008 |
| EP | 2 023 303 A1 | 2/2009 |
| EP | 2 037 990 A2 | 3/2009 |
| EP | 2 070 504 A1 | 6/2009 |
| EP | 2 105 895 A1 | 9/2009 |
| EP | 2 168 556 A1 | 3/2010 |
| EP | 2 174 251 A2 | 4/2010 |
| EP | 2 177 446 A1 | 4/2010 |
| EP | 2 184 590 A1 | 5/2010 |
| EP | 2 204 326 A1 | 7/2010 |
| EP | 2 272 767 A1 | 1/2011 |
| EP | 2 301 850 A2 | 3/2011 |
| EP | 2 305 566 A1 | 4/2011 |
| EP | 2 336 032 A1 | 6/2011 |
| EP | 2 345 605 A1 | 7/2011 |
| EP | 2 353 573 A1 | 8/2011 |
| EP | 2 394 938 A1 | 12/2011 |
| EP | 2 404 589 A1 | 1/2012 |
| EP | 1 420 980 A1 | 2/2012 |
| EP | 2 441 682 A1 | 4/2012 |
| EP | 2 455 763 A1 | 5/2012 |
| EP | 2 481 682 A1 | 8/2012 |
| EP | 2 497 715 A1 | 9/2012 |
| EP | 2 516 300 A1 | 10/2012 |
| EP | 2 565 036 A1 | 3/2013 |
| EP | 2 565 124 A1 | 3/2013 |
| EP | 2 628 475 A1 | 8/2013 |
| WO | WO 01/67345 A1 | 9/2001 |
| WO | WO 03/012470 A2 | 2/2003 |
| WO | WO 2004/033306 A1 | 4/2004 |
| WO | WO 2004/036516 A1 | 4/2004 |
| WO | WO 2004/053620 A2 | 6/2004 |
| WO | WO 2004/085939 A1 | 10/2004 |
| WO | WO 2004/088463 A2 | 10/2004 |
| WO | WO 2004/112685 A1 | 12/2004 |
| WO | WO 2005/078621 A1 | 8/2005 |
| WO | WO 2005/090167 A2 | 9/2005 |
| WO | WO 2006/032814 A1 | 3/2006 |
| WO | WO 2006/106749 A1 | 10/2006 |
| WO | WO 2007/040091 A1 | 4/2007 |
| WO | WO 2007/060588 A1 | 5/2007 |
| WO | WO 2007/072494 A1 | 6/2007 |
| WO | WO 2007/119303 A1 | 10/2007 |
| WO | WO 2008/040520 A1 | 4/2008 |
| WO | WO 2008/078575 A1 | 7/2008 |
| WO | WO 2008/085673 A1 | 7/2008 |
| WO | WO 2009/005044 A1 | 1/2009 |
| WO | WO 2010/032388 A1 | 3/2010 |
| WO | WO 2010/052913 A1 | 5/2010 |
| WO | WO 2010/104060 A1 | 9/2010 |
| WO | WO 2010/106944 A1 | 9/2010 |
| WO | WO 2010/110303 A1 | 9/2010 |
| WO | WO 2010/134058 A1 | 11/2010 |
| WO | WO 2011/006857 A1 | 1/2011 |
| WO | WO 2011/018998 A1 | 2/2011 |
| WO | WO 2011/027694 A1 | 3/2011 |
| WO | WO 2011/049167 A1 | 4/2011 |
| WO | WO 2011/049168 A1 | 4/2011 |
| WO | WO 2011/054053 A | 5/2011 |
| WO | WO 2011/078762 A1 | 6/2011 |
| WO | WO 2011/079352 A1 | 7/2011 |
| WO | WO 2011/102491 A1 | 8/2011 |
| WO | WO 2012/111498 A1 | 8/2011 |
| WO | WO 2011/115263 A1 | 9/2011 |
| WO | WO 2011/140617 A1 | 11/2011 |
| WO | WO 2011/155427 A1 | 12/2011 |
| WO | WO 2012/002342 A1 | 1/2012 |
| WO | WO 2012/002343 A1 | 1/2012 |
| WO | WO 2012/008393 A1 | 1/2012 |
| WO | WO 2012/013723 A1 | 2/2012 |
| WO | WO 2012/049446 A1 | 4/2012 |
| WO | WO 2012/049447 A1 | 4/2012 |
| WO | WO 2012/050120 A1 | 4/2012 |
| WO | WO 2012/062435 A1 | 5/2012 |
| WO | WO 2012/070643 A1 | 5/2012 |
| WO | WO 2012/076798 A1 | 6/2012 |
| WO | WO 2012/077591 A1 | 6/2012 |
| WO | WO 2012/087492 A2 | 6/2012 |
| WO | WO 2012/098247 A1 | 7/2012 |
| WO | WO 2012/098248 A2 | 7/2012 |
| WO | WO 2012/121565 A2 | 9/2012 |
| WO | WO 2012/136989 A1 | 10/2012 |
| WO | WO 2012/147907 A1 | 11/2012 |
| WO | WO 2012/148976 A1 | 11/2012 |
| WO | WO 2013/002067 A1 | 1/2013 |
| WO | WO 2013/013108 A2 | 1/2013 |
| WO | WO 2013/015227 A1 | 1/2013 |
| WO | WO 2013/028892 A2 | 2/2013 |
| WO | WO 2013/034504 A1 | 3/2013 |
| WO | WO 2013/040075 A2 | 3/2013 |
| WO | WO 2013/044069 A1 | 3/2013 |

(56) References Cited

OTHER PUBLICATIONS

International Search Report and Written Opinion for Application No. PCT/US2013/064597 dated Sep. 19, 2014.
Notice of Allowance for U.S. Appl. No. 13/835,431 dated Jun. 1, 2015.
Notice of Allowance for U.S. Appl. No. 13/836,107 dated Dec. 4, 2015.
Notice of Allowance for U.S. Appl. No. 15/057,783 dated Mar. 27, 2018.
Office Action for U.S. Appl. No. 13/835,431 dated Nov. 26, 2014.
Office Action for U.S. Appl. No. 13/835,599 dated Nov. 26, 2014.
Office Action for U.S. Appl. No. 13/835,779 dated Nov. 18, 2014.
Office Action for U.S. Appl. No. 13/836,107 dated Jan. 30, 2015.
Office Action for U.S. Appl. No. 13/836,107 dated Jun. 9, 2015.
Office Action for U.S. Appl. No. 13/836,290 dated Mar. 26, 2015.
Office Action for U.S. Appl. No. 13/836,554 dated Oct. 22, 2015.
Office Action for U.S. Appl. No. 15/057,783 dated Sep. 25, 2017.
Office Action for U.S. Appl. No. 16/018,580 dated Oct. 1, 2018.
Notice of Allowance for U.S. Appl. No. 16/018,580 dated Jan. 24, 2019.

* cited by examiner

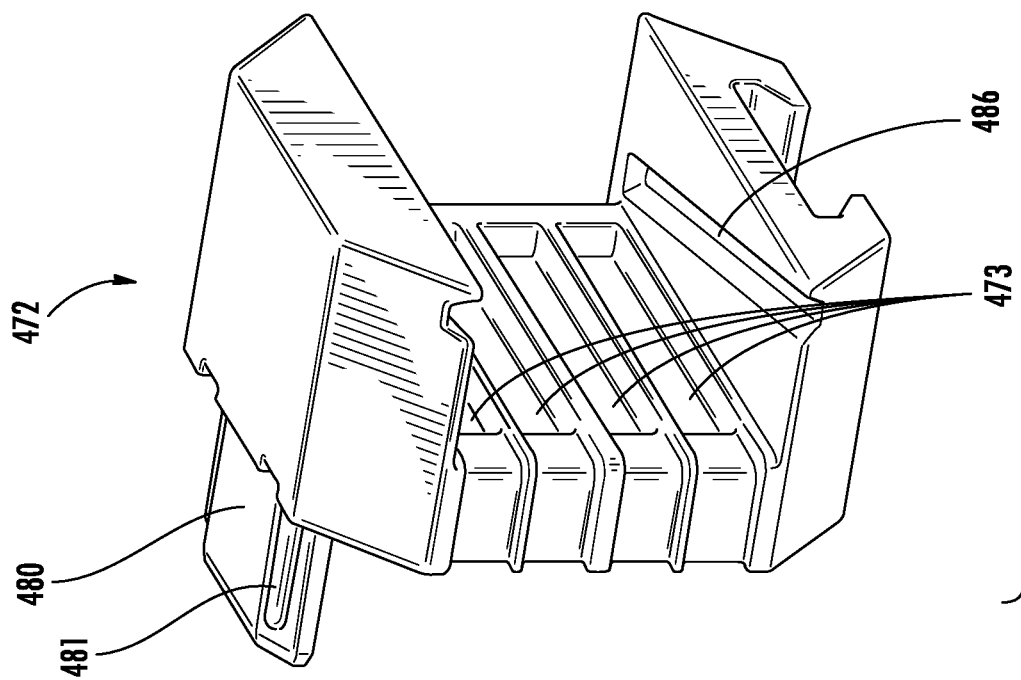
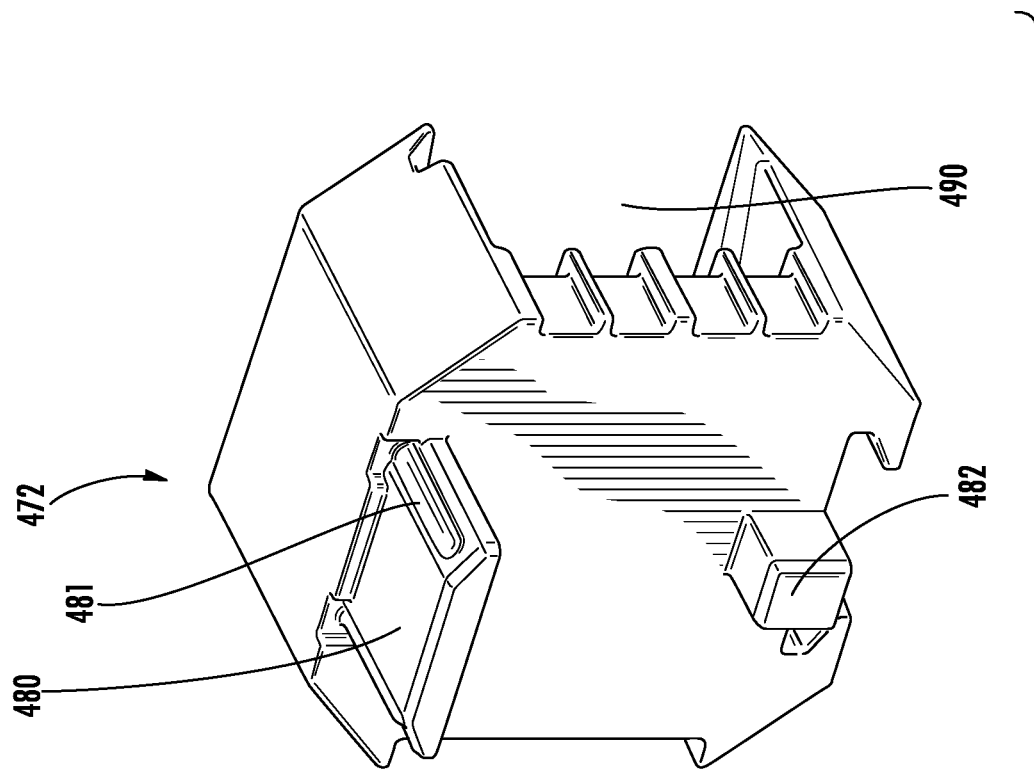
FIG. 33

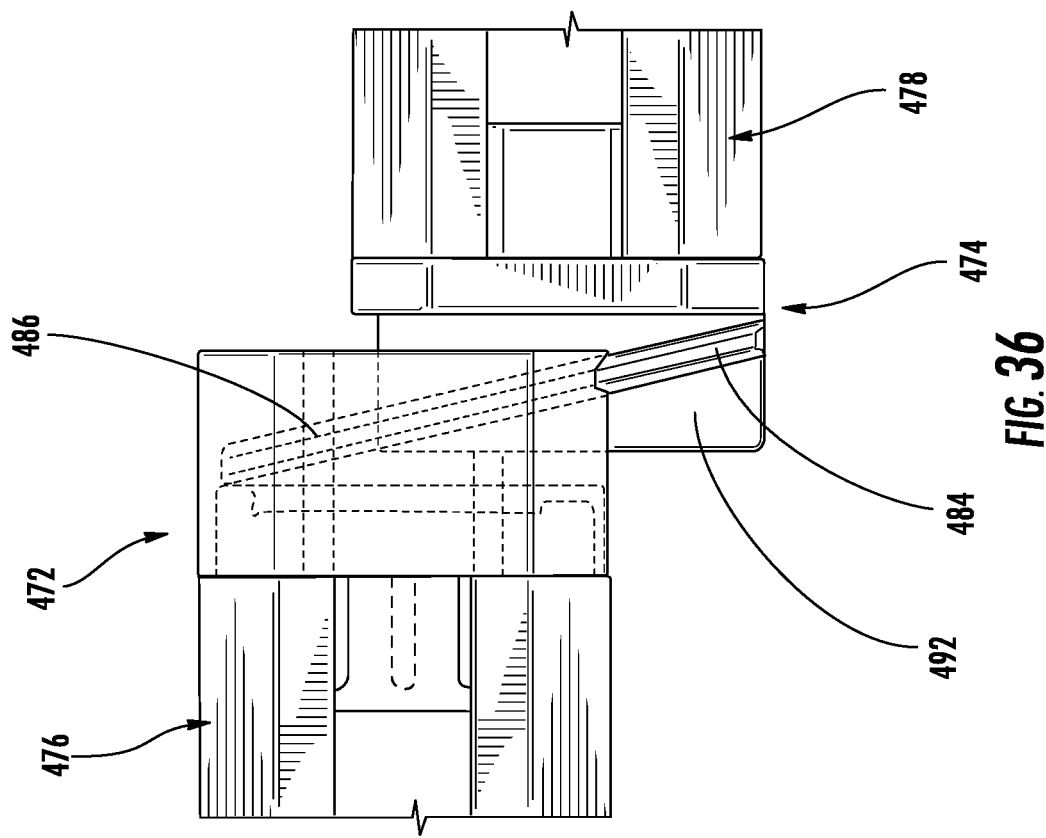
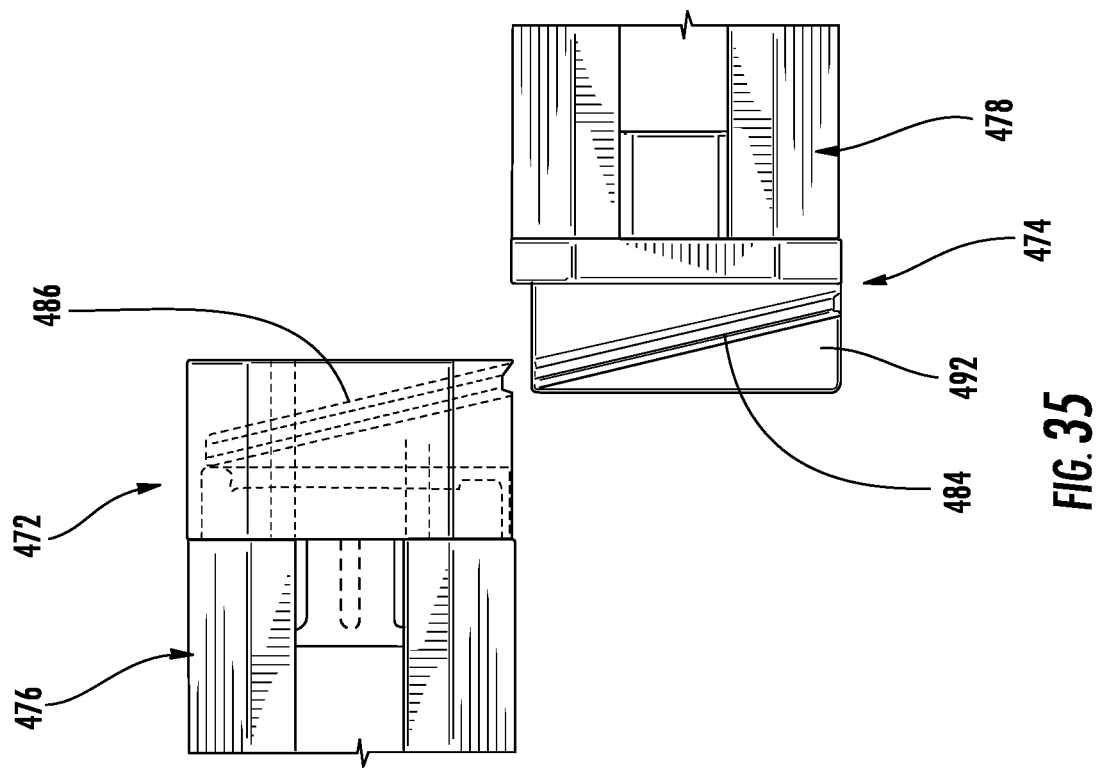

APPARATUSES, SYSTEMS, AND METHODS FOR TRANSPORTING MEDICATIONS FROM A CENTRAL PHARMACY TO A PATIENT IN A HEALTHCARE FACILITY

CROSS-REFERENCE TO RELATED APPLICATIONS

This application is a Continuation of and claims priority to U.S. patent application Ser. No. 16/018,580, filed on Jun. 26, 2018, which is a Continuation of and claims priority to U.S. patent application Ser. No. 15/057,783, filed on Mar. 1, 2016, which is a Continuation of and claims priority to U.S. patent application Ser. No. 13/836,107, filed on Mar. 15, 2013, which is a Non-Provisional application claiming priority to U.S. Provisional Patent Application Serial Nos. 61/713,228, 61/713,258, 61/713,268, 61/713,278, 61/713,298, 61/713,307, 61/713,321, 61/713,395, 61/713,360, 61/713,370, and 61/713,409, each filed on Oct. 12, 2012, and each of the aforementioned applications are herein incorporated by reference in their entirety.

TECHNOLOGICAL FIELD

Embodiments of the present invention relate generally to medication dispensing from the central pharmacy or medication storage area in a healthcare facility to a patient. Embodiments may include full or partial automation of the process and may include mechanisms for improving the efficiency and accuracy of medication dispensing.

BACKGROUND

Medication dispensing in healthcare facilities can be a complex and time consuming process. With medication orders changing, and with the significant potential ramifications of dispensing the incorrect medication to a patient, the process of delivering medication from the central pharmacy to the patient can be a high-risk process in a healthcare setting.

Healthcare facilities generally dispense medications from a central pharmacy to patients with a number of verification steps performed along the way to ensure that the medication is of the correct type and dose and that the appropriate patient receives the medication. The verification steps may add complexity and time to the process, thereby reducing the efficiency. Therefore it may be desirable to implement apparatuses, systems, and methods which may automate some or all of the process and which may increase the efficiency with which medications are delivered to a patient.

SUMMARY

Embodiments of the present invention may provide various apparatuses, systems, and methods for improving the efficiency of medication distribution within a healthcare facility. In particular, embodiments may provide for dispensing medications needed and medications anticipated to be needed to an authorized medical person for administration to a patient in a healthcare facility. Medications that are anticipated to be needed may be predicted based on a number of factors. The medications may be gathered, transported, stored, staged, and dispensed using one or more of the components described herein. Combinations of the components may be implemented for a system to automate or partially automate the dispensing of medications from a central pharmacy of a healthcare facility to a patient.

An example embodiment of the present invention may a method including receiving an indication of one or more unit dose medications anticipated to be needed by a patient; retrieving the one or more unit dose medications from a unit storage device; loading the one or more unit dose medications onto a transport device; transporting the one or more unit dose medications from the unit storage device to a location proximate the patient; and transferring the one or more unit dose medications from the transport device to a staging area at the location proximate the patient. Receiving an indication of one or more unit dose medications anticipated to be needed by the patient may include predicting the one or more unit dose medications anticipated to be needed by a patient over a specified period of time based on at least one of a conventional medication regimen for a particular ailment, a physician specific medication regimen for a particular ailment, a historical record of unit dose medications, or an algorithm. The algorithm may be based upon one or more of patient gender, patient age, patient symptoms, or patient vital statistics including one or more of temperature, pulse, blood-oxygen content, cholesterol level, or blood sugar.

According to methods of example embodiments, receiving an indication of one or more unit dose medications anticipated to be needed by a patient may include receiving a request for the one or more unit dose medications anticipated to be needed by the patient. Methods may also include estimating the time of arrival of the one or more unit dose medications at the location proximate the patient, and providing the estimated time of arrival. Retrieving the one or more unit dose medications from the unit storage device may include directing an X-Y robot to a location within the unit storage device for reach of the one or more unit dose medications, and retrieving each of the one or more unit dose medications from their respective locations within the unit storage device. Transporting the one or more unit dose medications from the unit storage device to the location proximate the patient may include advancing the one or more unit dose medications along a track with a car carrying the one or more unit dose medications.

Methods of example embodiments may optionally include dispensing the one or more unit dose medications from the staging area to authorized medical personnel in response to receiving a request from the authorized medical personnel. Receiving a request from authorized medical personnel may include identifying the authorized medical personnel by at least one of a biometric scan, receipt of an identification number, or receipt of identifying credentials. Methods may include retrieving at least one of the one or more unit dose medications from the staging area in response to a recall of the at least one of the one or more unit dose medications.

Example embodiments of the present invention may provide for a system for transporting medication within a healthcare environment. The system may include: a unit storage device configured to store a plurality of unit dose medications; a retrieving device configured to retrieve one or more of the plurality of unit dose medications from the unit storage device; a transport device configured to transport the retrieved one or more of the plurality of unit dose medications to a location proximate the patient; and a loading device configured to load the retrieved one or more plurality of unit dose medications onto the transport device. Each of the plurality of unit dose medications may be stored within the unit storage device in a bin, wherein each bin may include a uniform profile. Each of the plurality of unit dose medications may be stored within the unit storage device in an overpack, wherein each overpack includes unique identifying indicia disposed thereon.

Systems according to example embodiments may optionally include a scanner attached to the retrieving device, where the scanner is configured to scan the identifying indicia of each overpack prior to retrieval. Each bin containing a unit dose medication may be disposed in a compartment, where the compartments are arranged along a substantially vertical plane, where each compartment is directly accessible by the retrieving device. The retrieving device may include an X-Y robot configured to move across the substantially vertical plane and retrieve the one or more of the plurality of unit dose medications. The transport device may include a car, where the car includes a payload area and one or more bogies. The car may be configured to be driven along a track by an electric motor disposed within the transport device. The loading device may be configured to advance the one or more of the plurality of unit dose medications from the retrieving device to the payload area of the transport device. Systems may optionally include an unloading device, where the unloading device is configured to unload one or more of the plurality of unit dose medications from the transport device. The unloading device may be configured to unload one or more of the plurality of unit dose medications to at least one of a proximate storage location for retrieval by authorized medical personnel, or a staging area to await dispensing.

DESCRIPTION OF THE DRAWINGS

Reference now will be made to the accompanying drawings, which are not necessarily drawn to scale, and wherein:

FIG. 33 illustrates an example embodiment of a female end cap used to join to join track sections together according to an example embodiment of the present invention;

FIGS. 35 and 36 illustrate a method of engagement of a male end cap and a female end cap in order to join track sections together according to example embodiments;

DETAILED DESCRIPTION

Figure 1:
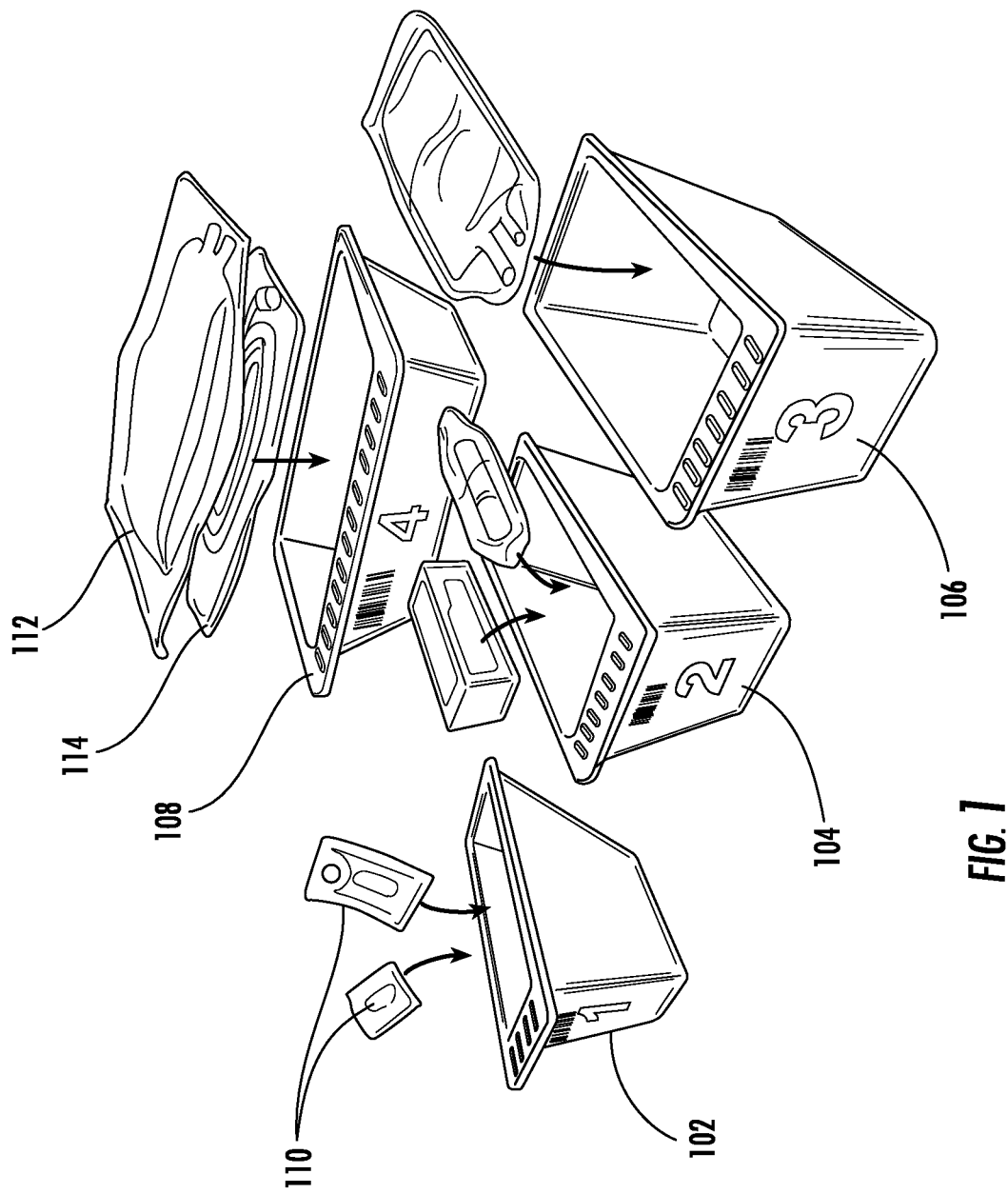
FIG. 1 illustrates an example embodiment of overpacks as described herein using multiple sized bins of a common profile.

Embodiments of the present invention may provide various apparatuses, systems, and methods for improving the efficiency of medication distribution within a healthcare facility. Some embodiments and components of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements.

Further, example embodiments of the present invention may provide a method, apparatus, and computer program product which may facilitate predicting the medications needed by a patient over a period of time. While automation of the dispensing of medications within a healthcare facility may improve efficiency of medication distribution, incorporating a mechanism to predict the medication needs for patients may allow automation to anticipate patient needs and to have medications readily available for administration to a patient when the patient requires the medications. Some medications for a patient may be previously prescribed such that they are known medications that will be needed for a patient. Other medications that may later be prescribed may not be known in advance of when they may be required. As such, a method of anticipating the medications which may be needed may help to ensure that medications are on hand when prescribed by a physician.

Embodiments of the invention configured to predict medications which may be needed by a patient may predict the medication based on a number of criteria. For example, the medications which may be needed by a patient may be predicted based on a knowledge of the patient's ailment, plurality of ailments, or combination of ailments, and the predicted medication may be based upon a conventional medication regimen for that ailment, plurality of ailments, or combination of ailments. Further, the medication regimen for the ailment, plurality of ailments, or combination of ailments may be physician specific, such that the medication regimen for ailments may be varied based upon the physician treating the patient. As a basic example, a patient with heartburn may be treated by one physician with a histamine antagonist medication while another physician may prefer proton pump inhibitor medication. The medication predicted for a particular patient may be dependent upon the preferences and/or historical information about the physician treating them.

Another criterion that may be used to predict medications which may be needed by a patient over a particular period of time may include a historical record of medication administered to the patient. For example, if a patient has a chronic condition and is on a maintenance medication, embodiments of the invention may predict that the patient will require their maintenance medication over the particular period of time. Further, a patient may have a historical record of medications taken for a particular ailment, such as in a prior visit to the healthcare facility. In such an embodiment, the record of the prior visit, the prior ailment, the prior medication administered, and the efficacy of the medication may each be considered.

While the aforementioned criteria are primarily historical correlations used for prediction of medication anticipated to be needed, additionally or alternatively, embodiments of the invention may implement an algorithm to predict the medication which may be needed by a patient over a predefined period of time. For example, if a patient has a combination of symptoms and/or particular abnormal vital statistics (e.g., pulse, temperature, cholesterol, blood sugar, etc.), an algorithm may take each of these variables into consideration to determine a predicted medication or medication regimen that the patient will need over a particular period of time.

Medications may also require specific supplies to accompany the medication such that supplies may be predicted in the same manner as medications. For example, if a medication is administered intravenously, a syringe may be a required supply to accompany the medication. As such, when the medication is anticipated to be needed, a syringe is also anticipated to be needed. Alternatively, the supply could be predicted when a medication is ordered.

While the prediction of medication which may be needed by patients over a particular period of time may increase efficiency of medication distribution, having the predicted medication ready for dispensing at or near the patient's location may further increase the efficiency of medication dispensing and administration. Such prediction and staging of medication may increase the efficiency of an authorized medical person, such as a nurse. For example, staging a medication proximate a patient and dispensing a medication to an authorized medical person proximate the patient may reduce the time needed for the authorized medical person to walk to retrieve medications and wait for their delivery. By reducing the time spent retrieving medications, additional time is afforded to an authorized medical person for administration of the medication or for care of a patient. This additional time may allow for higher quality patient care and less time spent in non-value added tasks of tracking down needed medications and supplies for a patient. Additionally, automating all or part of the distribution of medication in a healthcare facility may increase medication accuracy by providing automated verification of the medication type and dose at various stages of the distribution process.

Example embodiments of the present invention may provide various apparatuses, systems, and methods which may automate or partially automate some or all of the process of medication fulfillment and delivery from a central pharmacy to a patient. Embodiments may be implemented in full or in part to increase the efficiencies of the complex process of dispensing medications to a patient. As such, components described herein can be used individually or in combination with one another to achieve an automated or partially automated system for dispensing medications and supplies.

While embodiments of the present invention may be described with respect to healthcare facilities, such as hospitals and long-term care facilities, for example, embodiments of the inventions described herein may be implemented in a variety of types of facilities, not limited to those explicitly described herein.

Healthcare facilities may include a central pharmacy in which medications are stored and dispensed to areas throughout the healthcare facility. Some healthcare facilities may rely on a supplier, distribution center, or remote central pharmacy which stores medications and supplies at a remote location and delivers the medications and supplies on an as needed basis. In such an embodiment, the medications from the supplier, distribution center, or remote central pharmacy may be received by a healthcare facility at a receiving area. While embodiments of the present invention may be described as transporting and dispensing medication from a central pharmacy, embodiments in which central pharmacies are located remotely or embodiments using distribution centers may implement embodiments of the inventions from the area in which medications and supplies are received from the central pharmacy or distribution center. The indication of medications anticipated to be needed may be provided to the central pharmacy or distribution center with sufficient lead time such that the healthcare facility may receive the medications in advance of when they are anticipated to be needed.

In some example embodiments of the present invention, medications may be received from a remote central pharmacy in overpacks (described further below) or packaged into overpacks in a local central pharmacy. Overpacks may be means for packaging medication into a package that is more conducive to automated handling. The overpacks facilitate uniform handling to ease distribution and tracking within a healthcare facility. The medications in overpacks may be grouped together according to their destination, and the grouped overpacks may be transported to their destinations. The destination for the medication may include a unit storage device which may serve as local storage for medication to avoid having authorized medical personnel walk between their healthcare facility unit and the central pharmacy to retrieve medications. While storing medication locally in a healthcare facility unit may allow authorized medical personnel to retrieve medication locally for dispensing to patients on the unit, additional automation to deliver the medication closer to the patient may be implemented to further increase the efficiency of medication distribution in the healthcare facility.

Medications located in the unit storage may be individually selected and transported by an automated system to a location proximate to a patient, such as a patient server or a nurse server. A nurse server, according to example embodiments as will be described further below, may be a location situated close to a number of patients for which a nurse is responsible. The nurse server may receive medications only for those patients and may have controlled access restricted to authorized medical personnel. Similarly, the patient server of example embodiments may be disposed at a location proximate to a patient and be configured to receive medications only for that patient. The patient server may also have access restricted to authorized medical personnel.

Transport from the unit storage to the nurse server or patient server may be accomplished in a number of ways as outlined further below. Medications, which may be contained in overpacks, as described further below, may be selected from the unit storage by a retrieval device, and subsequently loaded onto a transportation device configured to transport the medications to a location proximate to the patient for whom they are intended. The transport device may include a train, a shuttle, a pneumatic tube system, etc.

Upon arrival of the medication at the nurse server or patient server, the medication may be unloaded from the transport device, or alternatively the transport device may remain with the medication at the nurse server or patient server. The medication may then be considered staged for retrieval by authorized medical personnel. The staging of medication may be, for example, in an overhead storage area disposed proximate a ceiling above the nurse server or patient server, awaiting a request for dispensing. The authorized medical person, which may be a nurse, technician, physician, etc., may be alerted that the medication for a patient is staged at the nurse server or patient server. When the authorized medical person is ready to administer the medication to the patient, they may access the nurse server or patient server, and they may be required to provide authentication, such as an identification card, an identification PIN, a biometric scan (e.g., retina, finger print, hand geometry, palm vein, facial recognition, or voice analysis). In response to authentication of the authorized medical person, the medication may be dispensed from the staging area to the nurse server or patient server for retrieval by the authorized medical person. Upon retrieval, the medication may be administered to the patient.

While the above description provides a general summary of some of the elements and operations of example embodiments of the present invention, certain elements and operations will be described further below.

Products to be Dispensed

Medications dispensed from a central pharmacy may be of a variety of form factors from individual pills or capsules to intravenous bags of a liter or more capacity. Other form factors may include syringes, carpujects, vials, etc. Supplies, such as intravenous medication tubing, empty syringes, etc. may be dispensed from a separate medical supply distribution center within a healthcare facility, or in some cases, the central pharmacy and medical supply distribution operations may be combined. Both the supplies and the medications may come in a variety of sizes and shapes and may not easily and efficiently be transported in uniform containers throughout a healthcare facility. For example, a carpuject, ampoule, or a vial may be relatively fragile while a unit dose of a medication, such as a tablet, may be relatively durable. While the tablet may be stored and dispensed in a very small package without substantial protection from transport, the vials, carpujects, and ampoule may require larger, more durable packaging. Similarly, intravenous medication bags may be durable for transport, but may be easily punctured such that care must be taken in storing, handling, and distributing such products.

While certain medications are configured to be dispensed in vials where a syringe is a required supply to accompany the vial, other medications may require a patient to consume food or a beverage other than water. In such cases, the food or beverage to accompany the medication may be treated as a supply, and such supplies may also be dispensed as other supplies may be dispensed as described herein.

In order to provide a more uniform form factor for medications and supplies to be handled and dispensed throughout a healthcare facility, overpacks or packaging that encases or holds the medications or supplies may be used which provide a common size, profile, shape, or grasping feature. Provided herein are various embodiments of uniform or quasi-uniform overpacks or secondary packaging for use with a variety of medications and supplies with varying shapes, sizes, and handling requirements (e.g., fragile, temperature sensitive, etc.). The overpacks described herein may provide an aspect of uniformity to generally non-uniform form factors. The uniformity may be in the profile of the overpack, such as when the overpack includes a plurality of various sized bins with uniform profiles, or the uniformity may be in a locating/holding hole of a plurality of various sized bags configured to hold the various form factors.

FIG. 1 illustrates an example embodiment of an overpack according to example embodiment of the present invention using bins of varying sizes with a common profile. Each of the illustrated bins 102, 104, 106, and 108 are of a different size while maintaining a common profile. The smallest bin 102 may be configured to hold small items such as unit doses of oral medication 110 (e.g., pills, capsules, tablets, etc.) while the largest bin 108 may be configured to hold large items such as a one liter intravenous bag 112 and/or intravenous tubing 114, each of which may be too large to fit into any of the smaller bins 102, 104, or 106. The bins between the largest and the smallest (bins 104, 106) may be appropriately sized to hold medications and/or supplies such as vials, syringes, 100 mL intravenous bags, or the like. The uniform profiles of the bins may allow the bins to be processed along a conveyor line configured to accommodate such a profile. Further, the uniform profile bins may be stored on common shelves with only the width of the shelf occupied varying between bins of different sizes. While some embodiments of bins of varying size may include a variable length, other embodiments may include a common length and a variable depth. For example, each bin may occupy the same width of a shelf, but the bin may extend further back on the shelf to create added capacity.

In some example embodiments, the overpacks may be sealed or closed to keep the contents of the overpack protected and/or secure. For example, the various sized bins of FIG. 1 may include lids which may be secured to the bins by a hook-and-loop fastener system, a snap-on lid, or a heat or ultrasonically welded plastic film seal. The type of closure used for the overpack may be dependent upon the use of the overpack. For example, an overpack for manual distribution (e.g., via a nurse cart) within a healthcare facility may not require a closure, or may use a simple snap-on closure. An overpack for automated distribution within a healthcare facility, or an overpack for distribution through an over-the-road delivery service may require a more secure closure that is less likely to be inadvertently opened, such as a heat-sealed film closure.

The closure may also depend upon the type of contents contained within the overpack. For example, if the overpack contains environmentally sensitive contents that should not be exposed to humidity or moisture may benefit from a heat-sealed film closure. Closures that are impervious to air and moisture may also be used for overpacks used with oxygen sensitive contents where an inert gas fills the overpack.

Figure 2:
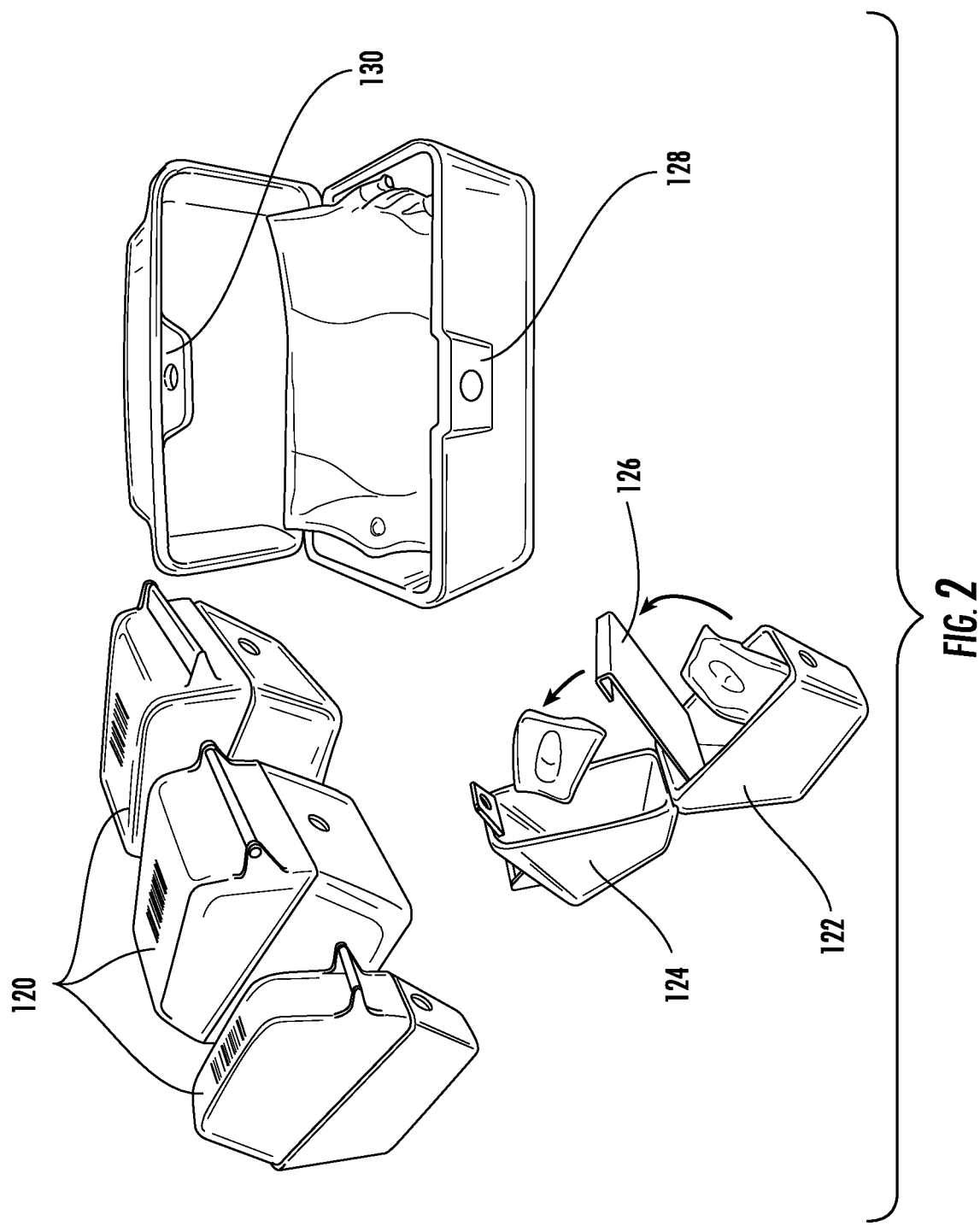
FIG. 2 illustrates another example embodiment of overpacks including lidded containers of multiple sizes, each having a common profile.

A closure for an overpack may also be selected based upon whether the contents are government regulated, as in the case of controlled substances, or if the contents are a high-value candidate for theft. In such embodiments, a lockable closure may be used to seal the overpack. FIG. 2 illustrates an example embodiment of an overpack with a hinged closure. As illustrated, the overpacks 120 of FIG. 2 may include a common profile, but have varying widths to accommodate medications and supplies of various sizes. The overpack base 122 and hinged lid 124 may open in a clamshell fashion to allow access to the interior cavity containing the medication or supply. As shown, the overpack may include a divider 126 which may allow two articles to be carried within one overpack without the two interfering with one another. The separation afforded by the divider may help to reduce confusion or mistakes when multiple medications are contained in an overpack for a particular patient. Also illustrated in the overpacks of FIG. 2 are a closure mechanism including a tab 130 received within latch 128. The closure mechanism may be a locking mechanism requiring a key, code, or biometric identifier. For example, authorized medical personnel may have access to a key, such as a magnetic key kept on their person or at a nurse station, which may unlock the latch 128. Optionally, the latch may be a push-button release configured only to maintain the lid 124 in a closed position during transport. While closures and locks may be used to secure controlled substances, security of controlled substances may additionally rely upon security by obscurity, in which narcotics and other controlled substances are not distinguished from non-controlled substances, such that locating controlled substances among the plurality of medication overpacks may be difficult.

Figure 3:
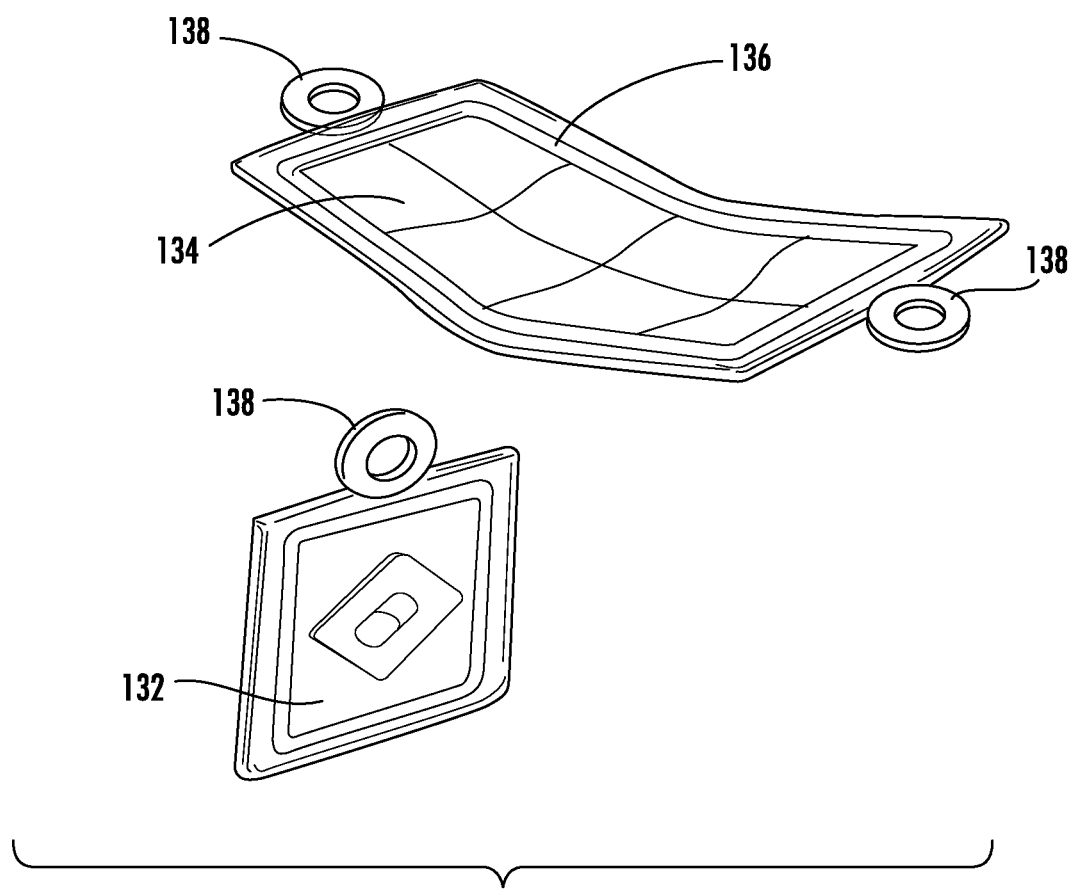
FIG. 3 illustrates another example embodiment of an overpack including a flexible film pouch with a grasping loop.

FIG. 3 illustrates another example embodiment of an overpack. The illustrated embodiment of FIG. 3 is a reusable folding pouch style overpack which may be available in various sizes to accommodate multiple sizes of medications and supplies. The pouch 132 may be made of a pliable material 134 which may be elastic to better hold the contents without shifting. The material may also be substantially transparent to allow easy verification of the contents of the pouch. The material 134 may have an adhesive strip 136 around the perimeter such that when the sheet of material 134 is folded, a pouch 132 is formed. The adhesive strip 136 may be a hook-and-loop type fastener or a releasable adhesive material to allow the pouch to be easily opened and reclosed for re-use. Optionally, the pouch style overpack may be designed for a single-use and may include a non-releasable adhesive requiring the pouch 132 to be torn open.

Such a single-use type pouch may be beneficial for embodiments requiring evidence of tampering. The pouch 132 may also include a loop 138 or hook which may be used to hang or grasp the pouch in transport and dispensing. As outlined above, some overpacks may include a common sized and/or shaped grasping feature, such as the loop 138 to aid automation or efficient handling as opposed to, or in combination with, a common size or profile.

Figure 4:
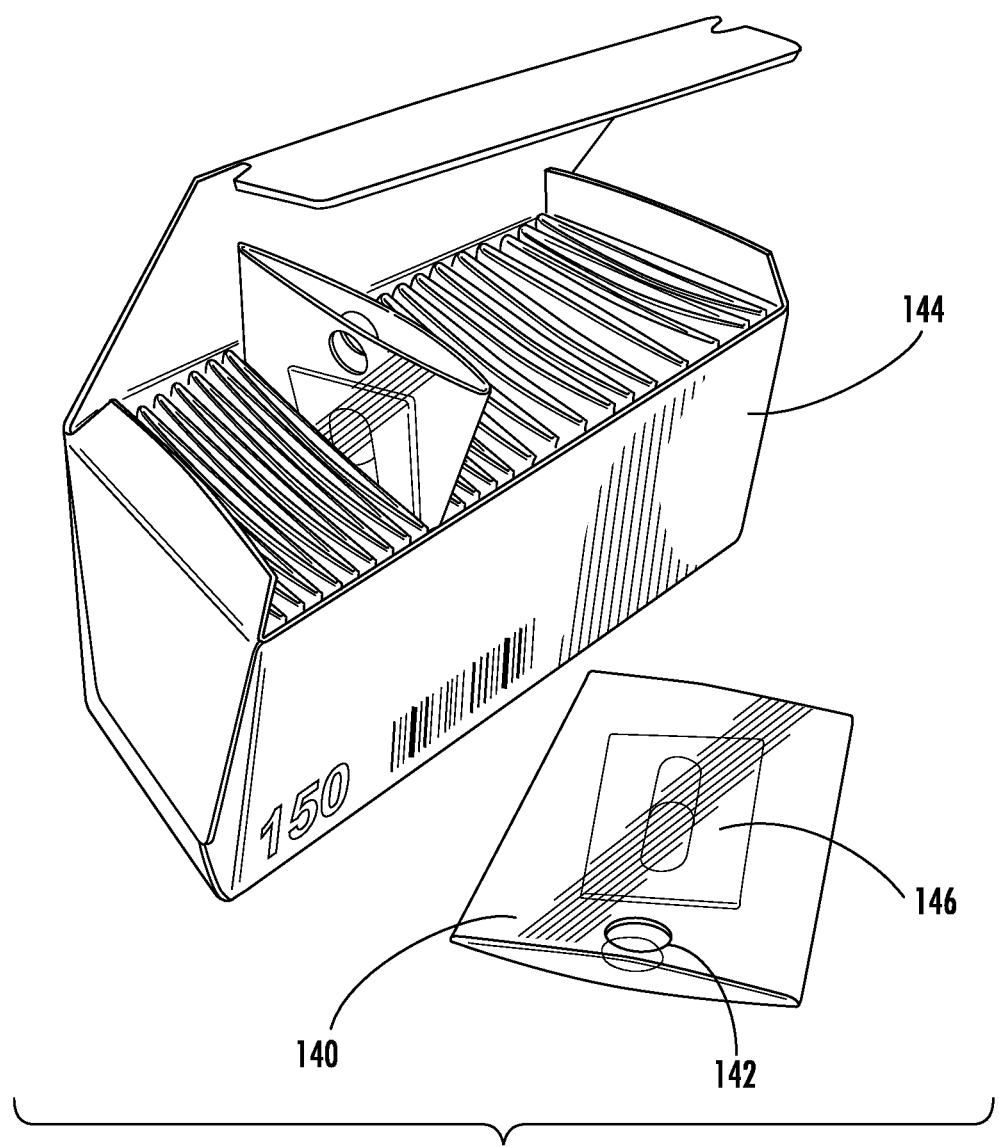
FIG. 4 illustrates an example embodiment of bags used as an overpack.

Overpacks according to the present invention may be embodied in other forms, such as envelopes or bags. FIG. 4 illustrates an example embodiment of an overpack in the form of a bag 140 including a hole 142. The bag type of overpack may be of any necessary size to accommodate the medication or supplies carried therein, and the hole 142 may be used for holding, storing, and grasping the bag 140. The bag or envelope style overpack may be conducive to use in instances where the medication or supply is received from a supplier as the cost of the overpack and material used therein is relatively minimal. Further, pharmacy automation tools, such as an automated dispensing system, may be configured to package and dispense medications and supplies in such overpacks, such that manual packaging of the medications or supplies into overpacks may not be required, thereby increasing efficiency and reducing cost. Some medications may be available from a supplier in bulk quantities in such overpacks, such as the illustrated box 144 of unit dose blisters 146 supplied in bag style overpacks 140.

Figure 5:
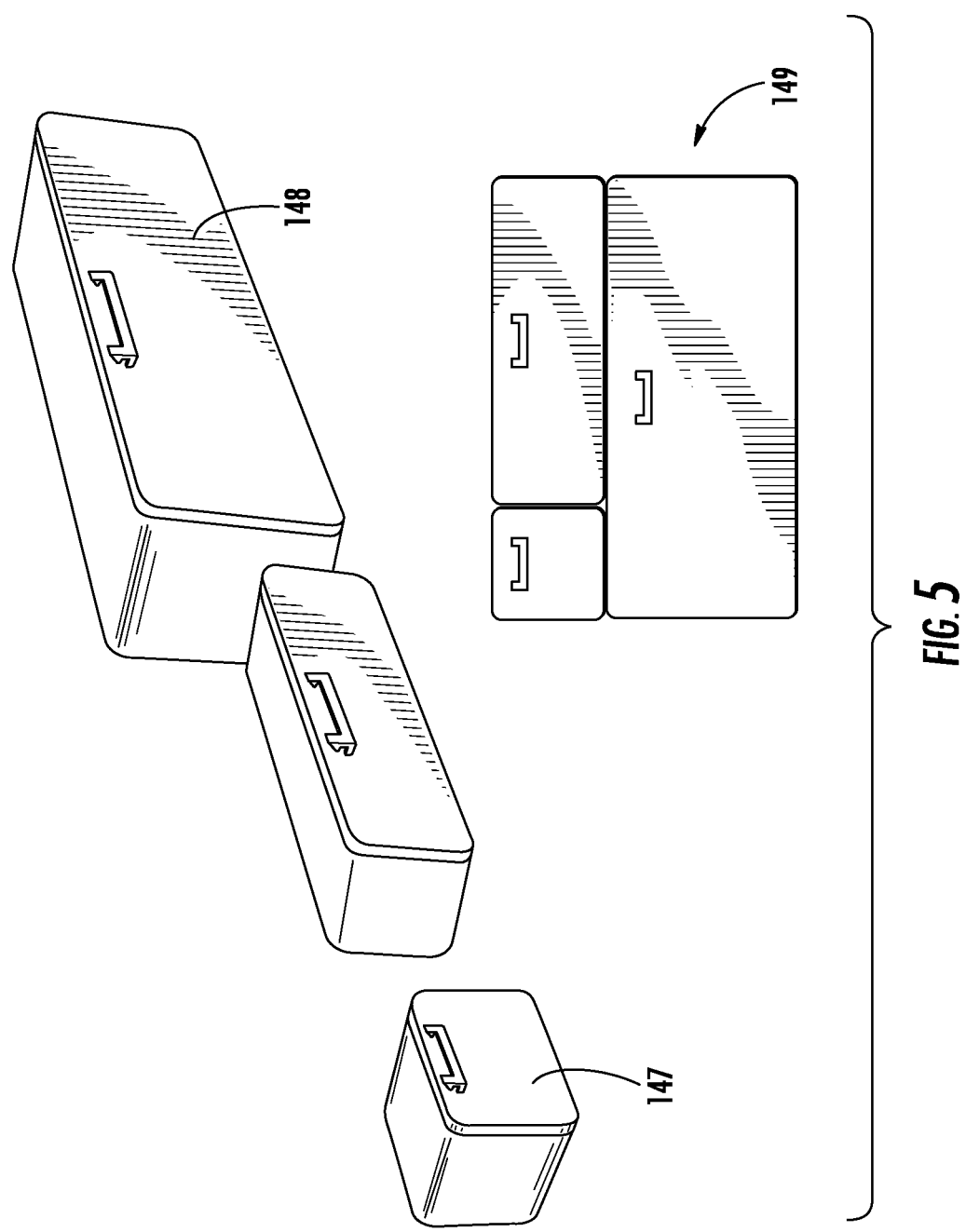
FIG. 5 illustrates multiple sized boxes as overpacks.

FIG. 5 illustrates another example embodiment of overpacks according to embodiments of the present invention. The illustrated embodiment includes various sizes of boxes, ranging from a small box 147 to a large box 148. The small size and the large size may be dictated by the sizes of medications and supplies to be handled within a healthcare facility. In the illustrated embodiment, the boxes 147, 148 include hinged doors on a front side of the box. The doors may be hinged proximate the bottom of the front, opening outward. The boxes may include a common depth such that the boxes may be arranged in a stacked configuration 149 while each of the doors to each of the boxes remain accessible.

Figure 6:
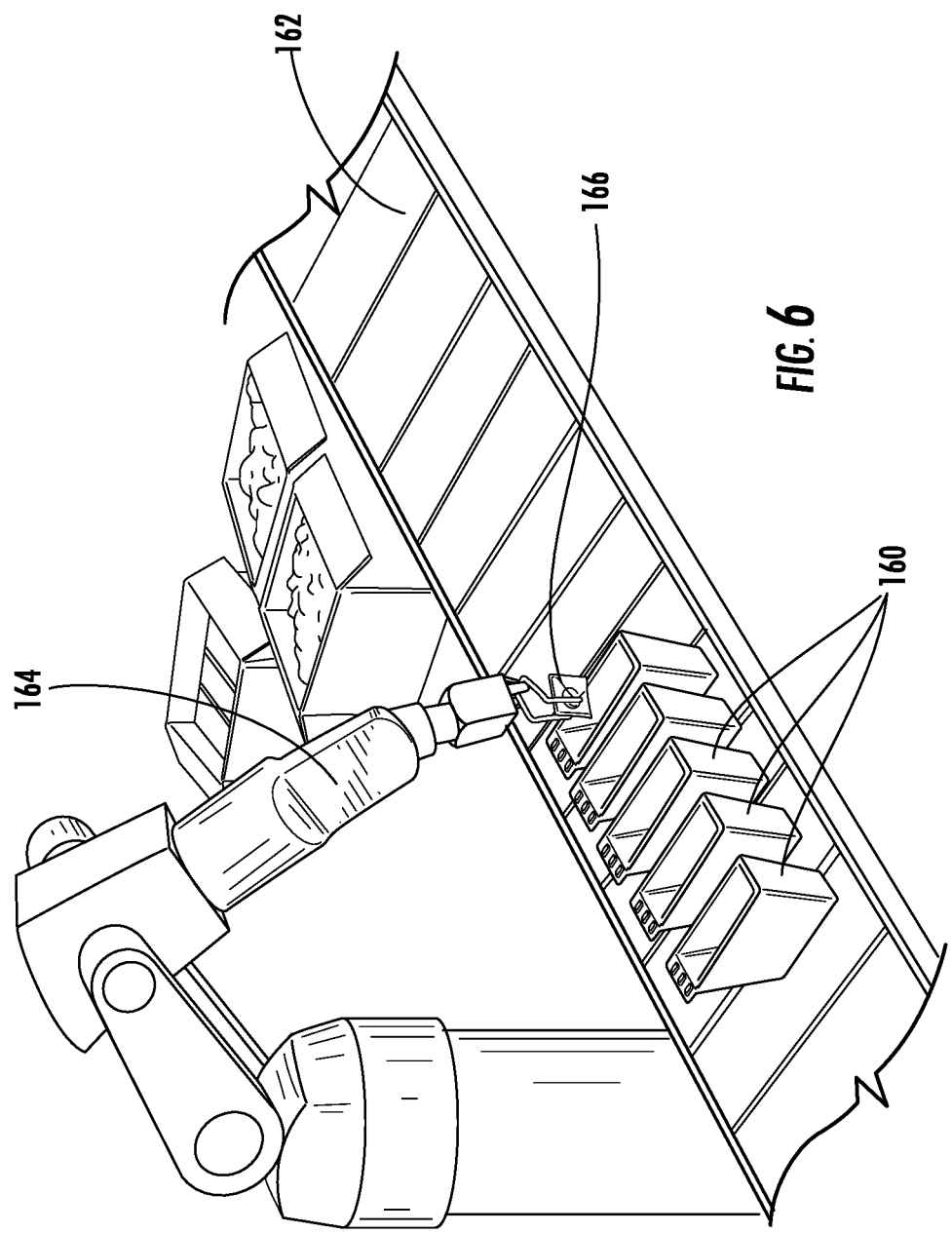
FIG. 6 illustrates automated loading of overpacks according to an example embodiment of the present invention.

Overpacks according to embodiments of the present invention may also facilitate automation of medication order fulfillment. For example, as illustrated in FIG. 6, empty bins 160 of various sizes but of a common profile may be configured to be transported along a conveyor 162 and be filled by a robot 164 or other form of automation. The robot 164 may place a medication or supply 166 into the bin 160 for dispensing to a patient. Embodiments of the present invention may also be used with existing automated pharmacy dispensing systems, such as Robot-Rx™ from McKesson® which may distribute medications from an inventory to an overpack for transport to a location proximate a patient.

Overpacks may be configured to contain only a single medication (i.e., a unit dose), a medication and a related supply (e.g., a vial of medication and a syringe), or the overpacks may be configured to contain multiple medications destined for the same patient. For example, if a patient requires five medications in the morning, three in the middle of the day, and four medications in the evening, an overpack may be filled with the five morning medications, a second overpack may be filled with the three middle-of-the-day medications, and another overpack may be filled with the four evening medications. In such an embodiment, individual tracking and control over unit dose medications may be lost; however efficiencies may be gained by using only a single overpack for each time of day that medication is required for the patient.

According to some embodiments of the present invention, overpacks may also include identifying indicia disposed thereon for identifying the contents of the overpacks. In one embodiment, the overpacks may include an overpack identification number which is correlated with a medication or supply that is placed into the overpack. The correlation between the overpack identification number and the contents may be performed by an automated system that loads the overpacks. Such a correlation would allow an overpack to be scanned to determine the overpack identification number, and then referenced in a database to determine the contents of the overpack without requiring a person to review the contents of the overpack. The database may be maintained by a server in the healthcare facility configured to track and monitor medication dispensing within the healthcare facility.

Figure 7:
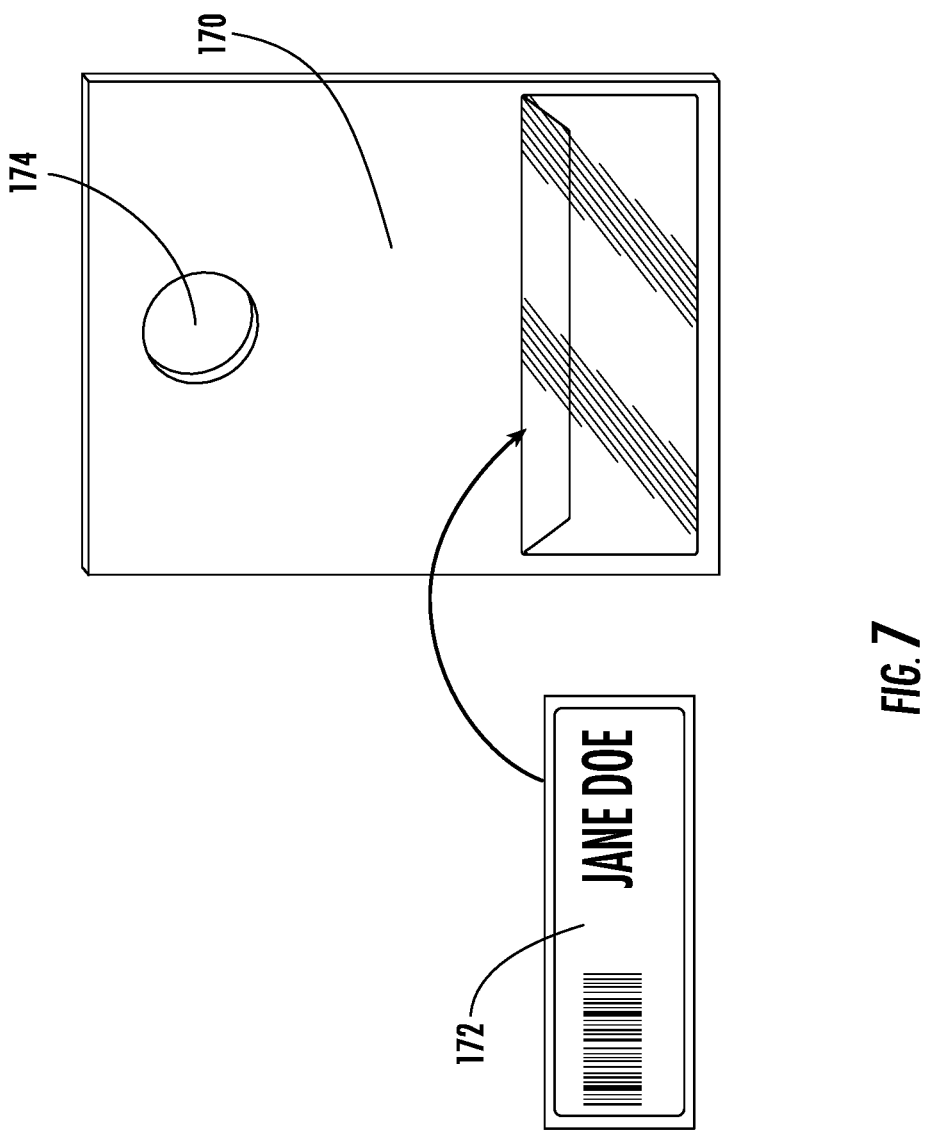
FIG. 7 illustrates another example embodiment of an overpack including a card-stock backing.

According to another embodiment, the overpack may include a label that is written to for denoting the contents of the overpack. FIG. 7 illustrates an example embodiment of a patient identification label 172 that is printed and paced into an overpack 170. The illustrated overpack may be a blister pack, bag, or envelope configured to receive a medication unit dose. The overpack 170 may further be configured with a hole 174 for uniform storage and retrieval. While illustrated as a patient identification label 172, the label attached to an overpack may identify the contents of the overpack without regard for a specific patient. In the illustrated embodiment, the patient identification label may include a barcode or other indicia identifying the patient and the patient identification label 172 may be inserted into a pocket or otherwise affixed to the overpack 170. The identification may also be printed directly onto the overpack material rather than onto a separate label.

Figure 8:
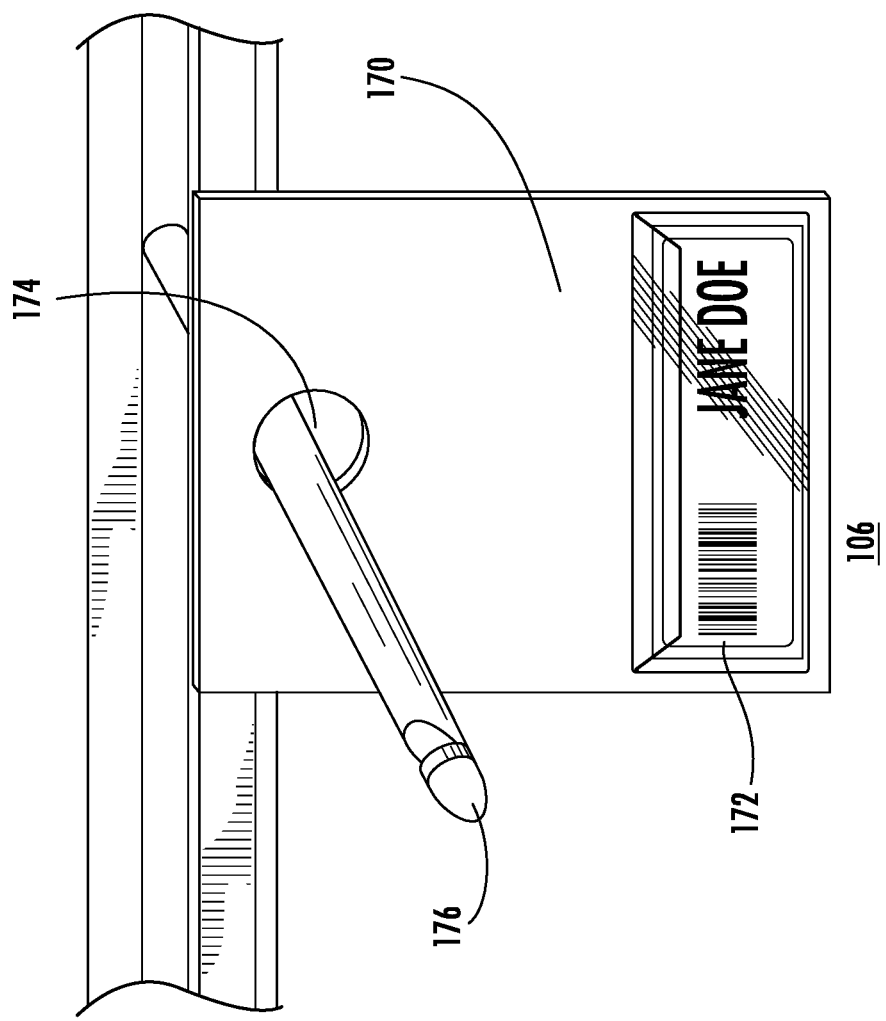
FIG. 8 illustrates the storage of overpacks according to an example embodiment of the present invention.

FIG. 8 illustrates an example embodiment of the overpack 170 as carried on a rod 176. The overpack 170 may be carried on the rod 176 for automated distribution, transport, or storage. While the illustrated patient identification label 172 includes a barcode and name, embodiments may include a patient or overpack contents label that includes a radio frequency identification (RFID) label configured to be read by an RFID reader exclusive of or in addition to other identifying indicia, which may include barcodes, text, or other human or machine readable information. In some embodiments, the label 172 may include an image of the medication that is supposed to be contained within the overpack 170 to allow authorized medical personnel to visually confirm the contents of the overpack are correct. While identifying indicia may be printed to a label, embodiments of the present invention may include overpacks using electronic ink labels. Electronic ink labels may be "printed" by programming such that when a medication or supply is loaded into an overpack the electronic ink label is programmed to display identifying indicia about the medication or supply contained within the overpack. Electronic ink labels may function in the same manner as conventionally printed labels (e.g. by thermal printing, ink jet printing, laser printing, etc.) such that they may be read by a user or by a reading device.

Additionally or alternatively, medications, such as blister packs may include identifying information printed to the blister pack. Overpacks may be configured such that the identifying indicia of the medication packaging is readable through the overpack. For example, a blister pack with identifying information thereon may be placed into a bag through which the blister pack may remain readable.

Input Organization

Medications or supplies, whether packaged in overpacks as outlined above, or in their native containers (such as blister packs for pills or intravenous bags), may be stored and transported within the healthcare facility. Storage of the medication and supplies may be within the central pharmacy or at a unit storage device. While the central pharmacy may supply medications and supplies to an entire healthcare facility, a unit storage device may be located remotely from the central pharmacy and may be configured to store medications and supplies only for patients serviced in a particular unit of the healthcare facility as will be described in further detail below. As such, there may be multiple unit storage devices within a healthcare facility.

Transporting or moving medications and supplies within a healthcare facility is inefficient when the medications are moved individually or without regard for other medications that are bound for the same or a similar destination. As such, logistics may be implemented to optimize transport and to efficiently move groups of medications to common locations, such as unit storage devices, within a healthcare facility. Software may be used to group together a plurality of medications or supplies in overpacks to be sent to the same location. The software may be implemented on a user terminal, as described further below, or across a network of a healthcare facility. The software may determine which overpacks are to be grouped, and route them to their appropriate destination. As described herein "routing" of medication and supplies within a healthcare facility includes generating a route or a planned route for the medication and supplies. Routing is generally provided by software, while the physical transport of the medication and supplies is performed by hardware, or in some cases, people. For example, a route may be established for an individual unit dose in an overpack; however, that overpack may be transported together with other overpacks that have the same, or a portion of the same route.

Embodiments of the present invention may provide means for organizing medication and/or medication overpacks for efficient transportation from the central pharmacy. In order to efficiently move medications and supplies or products within a healthcare facility, the medications and supplies may be organized into groups of medications and supplies that are bound for the same general location, such as the same unit storage device. Further, individual accessibility to, or identification of each of the medications or supplies that are within a group may be desirable. Once the medications and supplies arrive at their common destination, they may need to be placed into a unit storage device or otherwise distributed as appropriate. Therefore, organization of the medications and supplies for transport to the unit storage devices may increase efficiency of retrieval and local storage of the medication and supplies.

Provided herein are methods and apparatuses to organize and transport medication and supplies from a central pharmacy or from a remote pharmacy and/or from a central supply storage location to local storage, such as at a unit storage device. The manner in which the medications and supplies may be organized for transport may facilitate automation and enhance the efficiency of their distribution.

Commonly used medications, such as aspirin, may be provided in cartridges or magazines where individual unit doses of medication are available to be dispensed from the magazines. The magazines or cartridges may be configured to be received by a local storage device (e.g., a unit storage device) for distribution on an as-needed basis. Magazines and cartridges allow for a high volume of storage in a relatively compact form factor. The shape of the medication package or overpack may also allow for efficient one-at-a-time distribution of the medication from the magazine or cartridge. Dispensing may be performed from the bottom of a magazine or from the top using a variety of mechanisms to singulate a unit dose or unit dose package of medication from the plurality of unit dose packages of medication within the magazine. Cartridges may also contain rolls of unit dose medication with individual packages and perforations therebetween.

Figure 9:
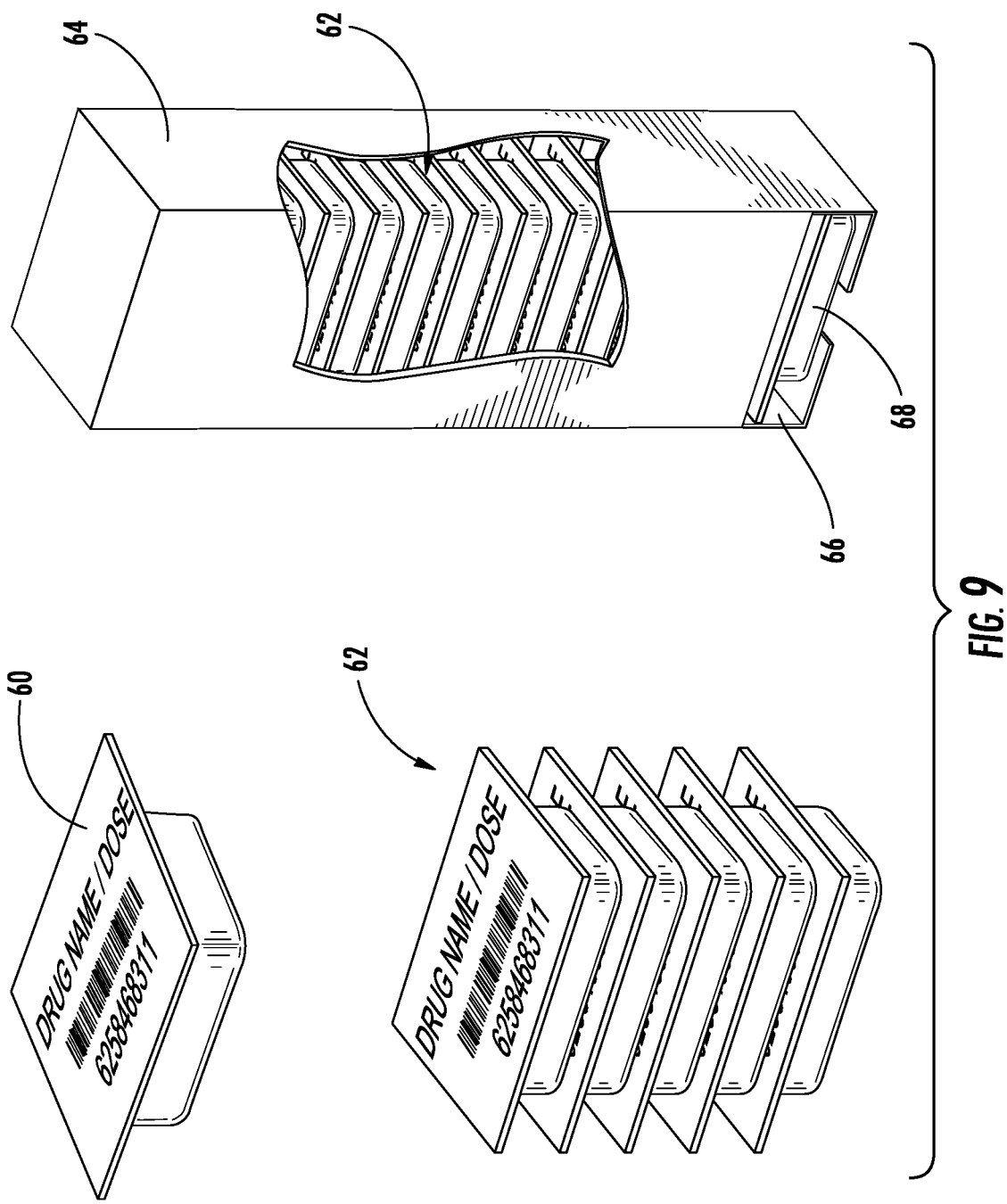
FIG. 9 illustrates a magazine containing a plurality of stacked unit dose medications according to an example embodiment of the present invention.

An example embodiment of a magazine is illustrated in FIG. 9. The illustrated embodiment depicts a medication package 60 which may include a unit dose of medication. The illustrated medication package 60 may be conducive to automated handling and may not require an individual overpack; however, in some embodiments, such as overpacks including various sizes of bins, the medication package 60 may be dispensed to a an overpack bin for automated transport. The medication package 60 may include a medication name, dose, lot number, expiration date, or any similar identifying indicia. The indicia may be in the form of text, barcode, or an RFID tag. A plurality of medication packages 62 may be stacked and inserted into a magazine 64. The cutaway of the magazine 64 illustrates the plurality of medication packages 62 disposed inside. The magazine 64 may be filled at a central pharmacy, or the magazine may arrive at the central pharmacy previously loaded with unit dose medications ready for dispensing. A medication package 68 at the bottom of the stack of medication packages 64 may be arranged proximate an opening 66 in the magazine 64, ready to be pushed or drawn out of the magazine 64.

Systems according to example embodiments of the present invention may include a device configured to remove a medication package 68 from a magazine 64 automatically in response to an indication for a need for the medication; however, magazines of example embodiments may also be implemented in manual-fill operations where a user may pull a medication from the magazine. Example embodiments of automated systems for dispensing medication packages from magazines are detailed further below.

Figure 10:
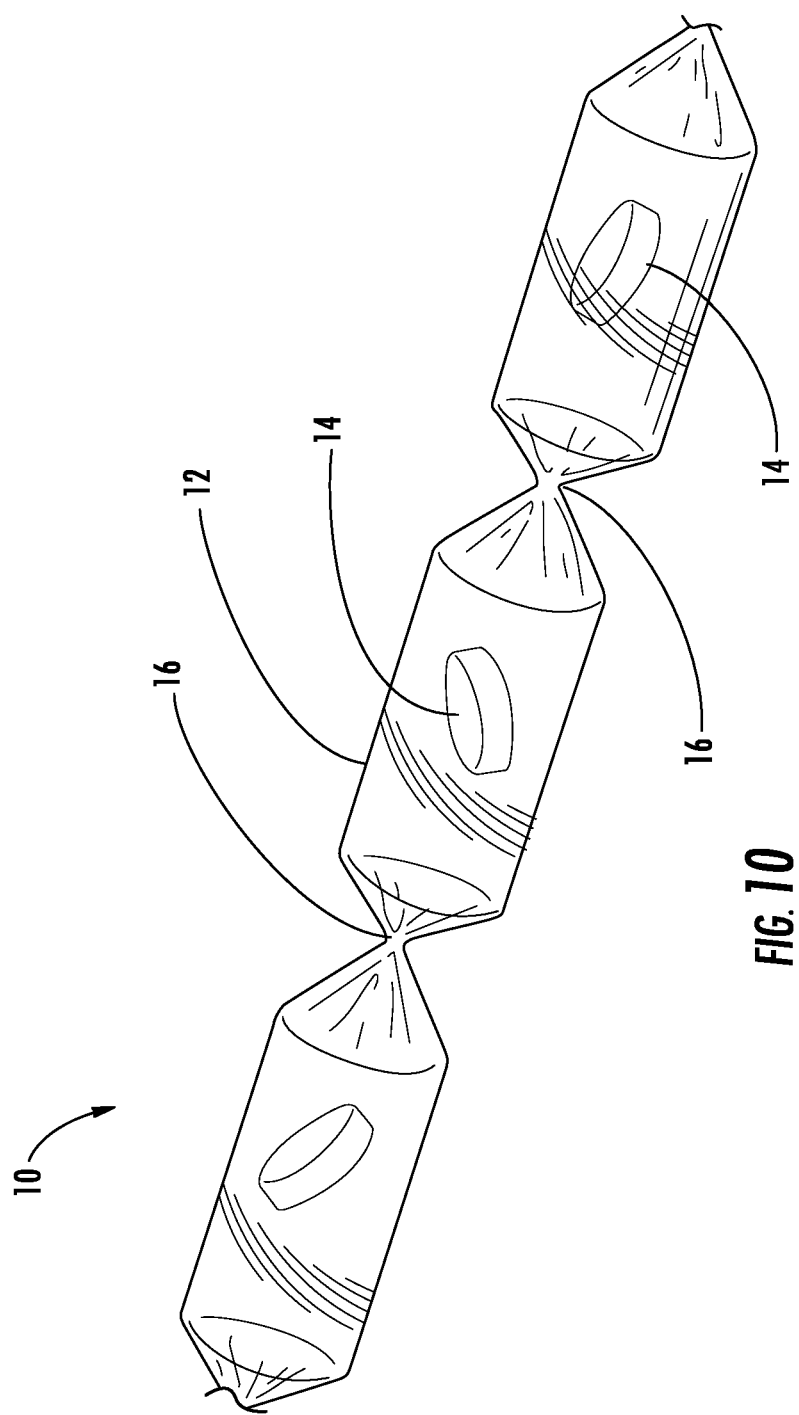
FIG. 10 illustrates a plurality of interconnected unit dose medication packages.

Another example embodiment of an apparatus for packaging commonly used or as-needed medications may include a "sausage-link" type package as illustrated in FIG. 10. The sausage-link overpack 10 may include a tube of material, such as plastic, which may receive a unit dose of medication 14 and be crimped 16 on either side of the unit dose. The tube may be structured, such that it holds its shape as in the case of a material such as low-density polyethylene (LDPE), or it may be a flexible film, such as polyvinylidene chloride (PVDC). The crimping may be performed, for example, by heat or ultrasonic welding of the tube material between the unit doses of medication 14. The crimps 14 may further include perforations or other structurally weakening features to allow for easy separation of a unit dose links. A plurality of linked unit dose links may be stored in a spool or accordion style magazine such that a link may be pulled out, separated, and the next link containing a unit dose medication 14 is ready for use. The sausage-link type package may include indicia written thereon, and/or the sausage-link type package may include a blister pack therein which may have identifying indicia written thereon. The indicia of the blister pack may be readable through the sausage-link type packaging such that additional indicia may not be necessary.

Packaging of medications that may be stored in bulk in unit storage devices may also include a two-dimensional array of unit dose packages adhered to a backing. For example, a backing with a releasable adhesive may receive thereon a plurality of unit dose medications, such as blister packs of pills. When a unit dose is needed, a nurse or other authorized medical person may remove one or more of the unit doses from the two-dimensional array as needed.

Figure 11:
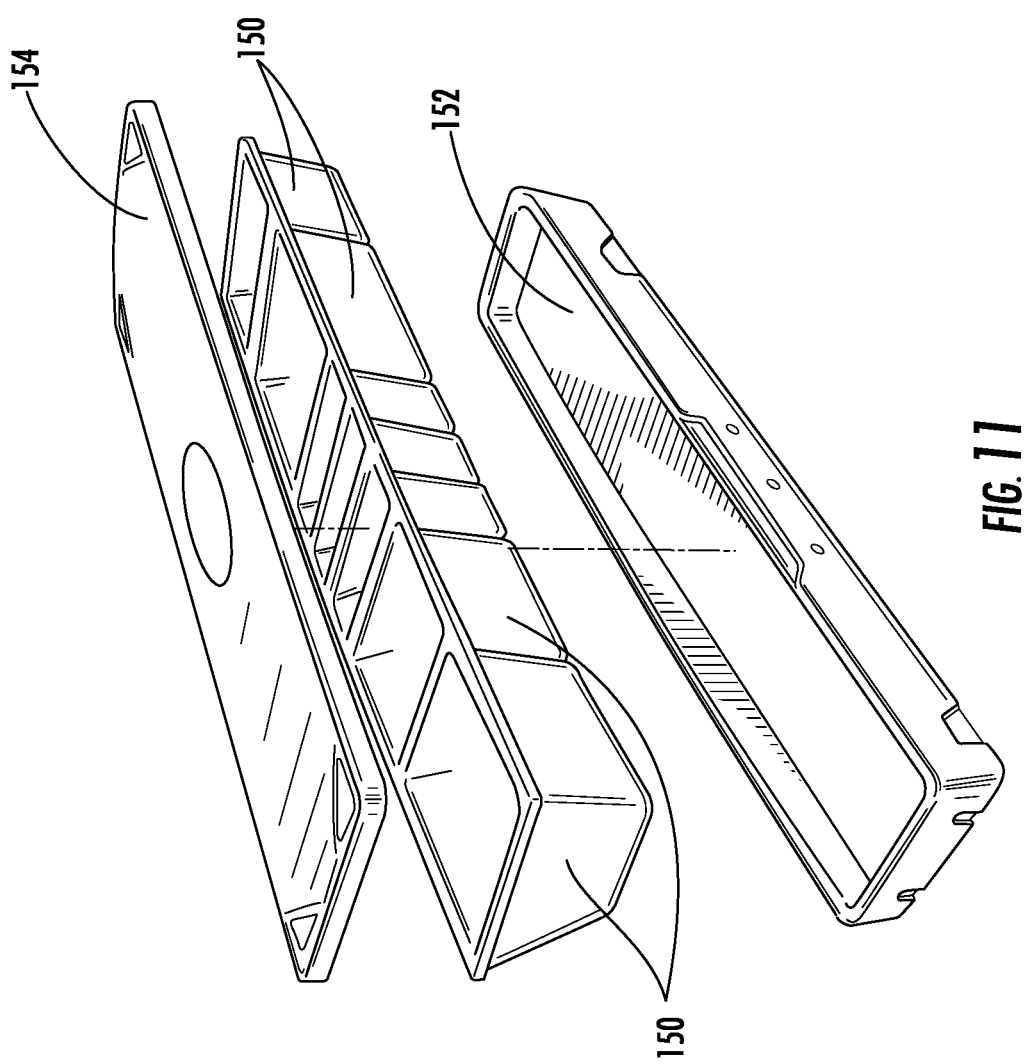
FIG. 11 illustrates a system loading device including a plurality of bins of multiple sizes and a common profile according to an example embodiment of the present invention.

While some medications and supplies may be stored locally on healthcare facility units for use as-needed, such as aspirin, bandages, alcohol swabs, etc., other medications and supplies may be distributed to healthcare facility units only in response to a perceived or actual patient need, as described above with regard to predicting medications which may be needed by a patient. In order to distribute medications within the facility based upon an indication that the medication may be needed, medications and supplies may be grouped with other medications and supplies bound for the same healthcare facility unit to be transported to the healthcare facility unit. An example embodiment of such a grouping may include trays configured to hold a plurality of bins as described above with regard to the bins 102, 104, 106, and 108 of FIG. 1. FIG. 11 illustrates an example embodiment of a plurality of bins 150 of various sizes, but with a common profile, that may be loaded onto a tray 152. The plurality of bins 150 may also be covered, as a unit, with a single lid 154. The lid 154 may be exclusive of, or in addition to individual closures on the individual bins 150 themselves. The lid 154 covering all of the bins 150 may provide security to the bins 150 to maintain them in position on the tray 152 during transport, and the lid 154 may discourage or prevent removal of an individual bin from the tray when the tray is between the central pharmacy and the local storage.

The tray 152 of example embodiments may be sized and shaped to accommodate a plurality of overpacks and to hold them securely to prevent shifting of the overpack during transport. As shown in FIG. 11, the tray 152 is configured to receive a plurality of bins 150 with varying sizes. In order to maximize the use of the tray 152 and to help prevent shifting of the bins 150 within the tray, the bins may fully occupy the tray. Since there are bins 150 of varying sizes, some combinations of bin sizes will fully occupy the tray 152, while others will fall short of occupying the full tray. A software program may be configured to direct the bins that go on each tray to maximize the use of each tray. For example, a software program may recognize 50 bins that are to be transported to a particular healthcare facility unit. The software may analyze the size of each bin and compile groups of bins that fully utilize trays to maximize the tray use and increase the efficiency of the transportation. The software may be configured to provide information to a person who is manually loading bins 150 onto the tray 152, or alternatively, in an automated loading system, the software may direct the placement of specific bins on specific trays by an automated loading mechanism which loads the bins into the trays. Once loaded, the trays are ready to be transported to their destinations. The tray 152 may have features at regular intervals, such as slots, detents, or dividers to prevent bins 150 from moving or shifting while on the tray.

The software described herein may be part of a suite of software or a software with a plurality of functions including: predicting the anticipated medications which may be needed by patients; loading medications and supplies into overpacks; grouping overpacks for transport to local storage; establishing a route for overpacks to their appropriate destination; directing transport of the overpacks to proximate storage; and dispensing medications and supplies. The software may perform some or all of these functions while tracking each medication throughout the healthcare facility. The software may further be combined with other software used for administering medications and tracking overall inventory counts.

Figure 12:
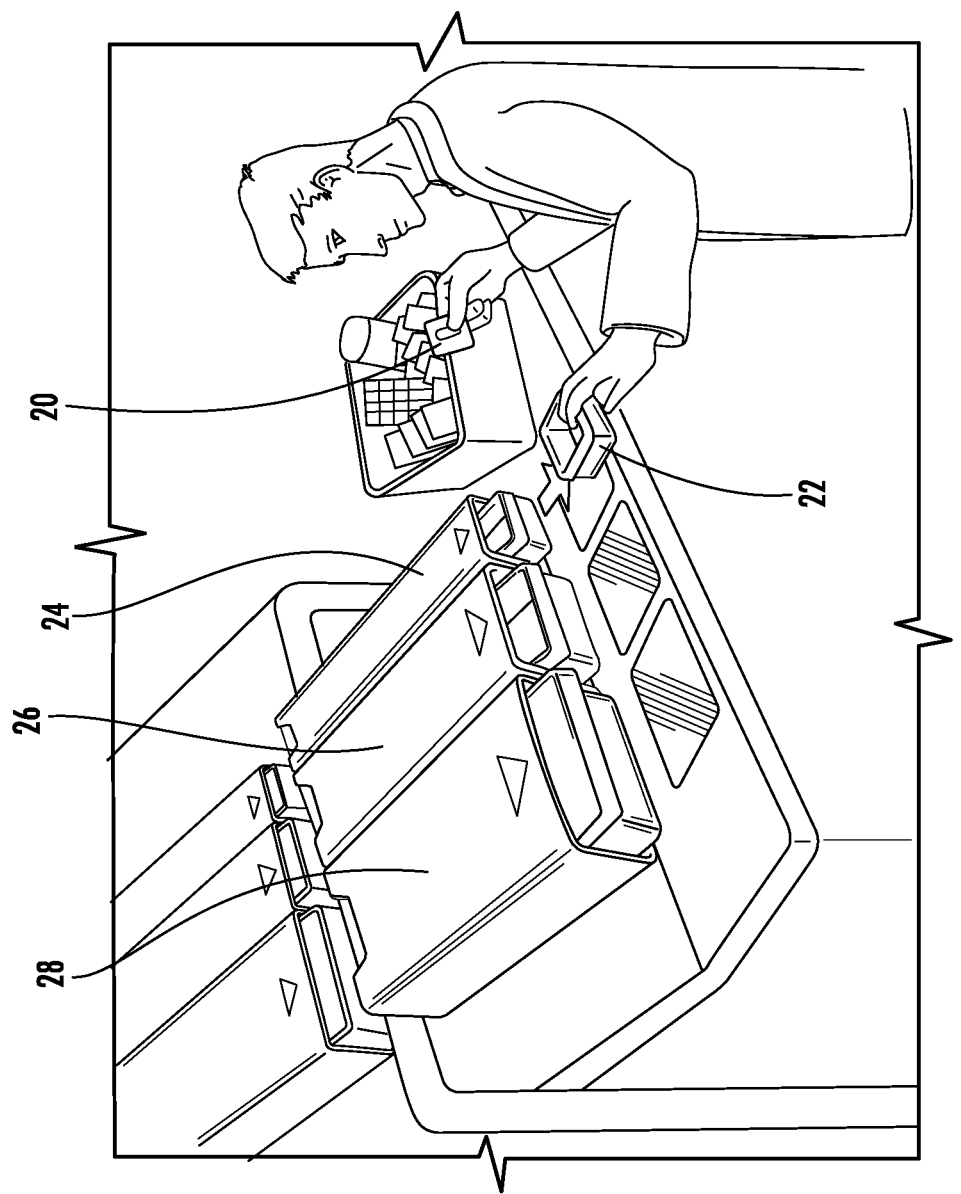
FIG. 12 illustrates an example embodiment of a system configured to load overpacks and group loaded overpacks onto a tray or cassette.

FIG. 12 illustrates an example embodiment of a system configured to load overpacks and group the loaded overpacks onto a tray or cassette. In the illustrated embodiment, a medication unit dose 20, such as a blister pack, may be scanned using a reader to identify the medication by barcode, RFID tag, or other identifying indicia of the unit dose medication. The scanning may be performed automatically or manually by a user. Upon scanning, the software that recognizes the identity of the medication unit dose 20 may identify the appropriate bin size. For example, a unit dose blister may require only a small bin, while a 100 mL IV bag may require a large bin. The software may present the appropriate size bin to the user, direct the user to the appropriate bin, or simply indicate to the user the bin size appropriate for the medication unit dose via a user interface. In the illustrated embodiment, an empty bin 22 of the appropriate size is pulled from a cassette 24 containing bins of the appropriate size. Other cassettes 26, 28 may contain bins of other sizes. The user may then place the unit dose medication 20 into the selected bin 22. Each bin may include unique identifying indicia thereon, such as a serial number, which may be scanned to correlate the medication placed therein with the overpack serial number. Subsequent scanning of the overpack may reference a database to determine the medication that is associated with that particular overpack. Additionally or alternatively, a label may be printed or electronically written to for the overpack such that the overpack may have a label identifying the contents of the overpack.

Figure 13:
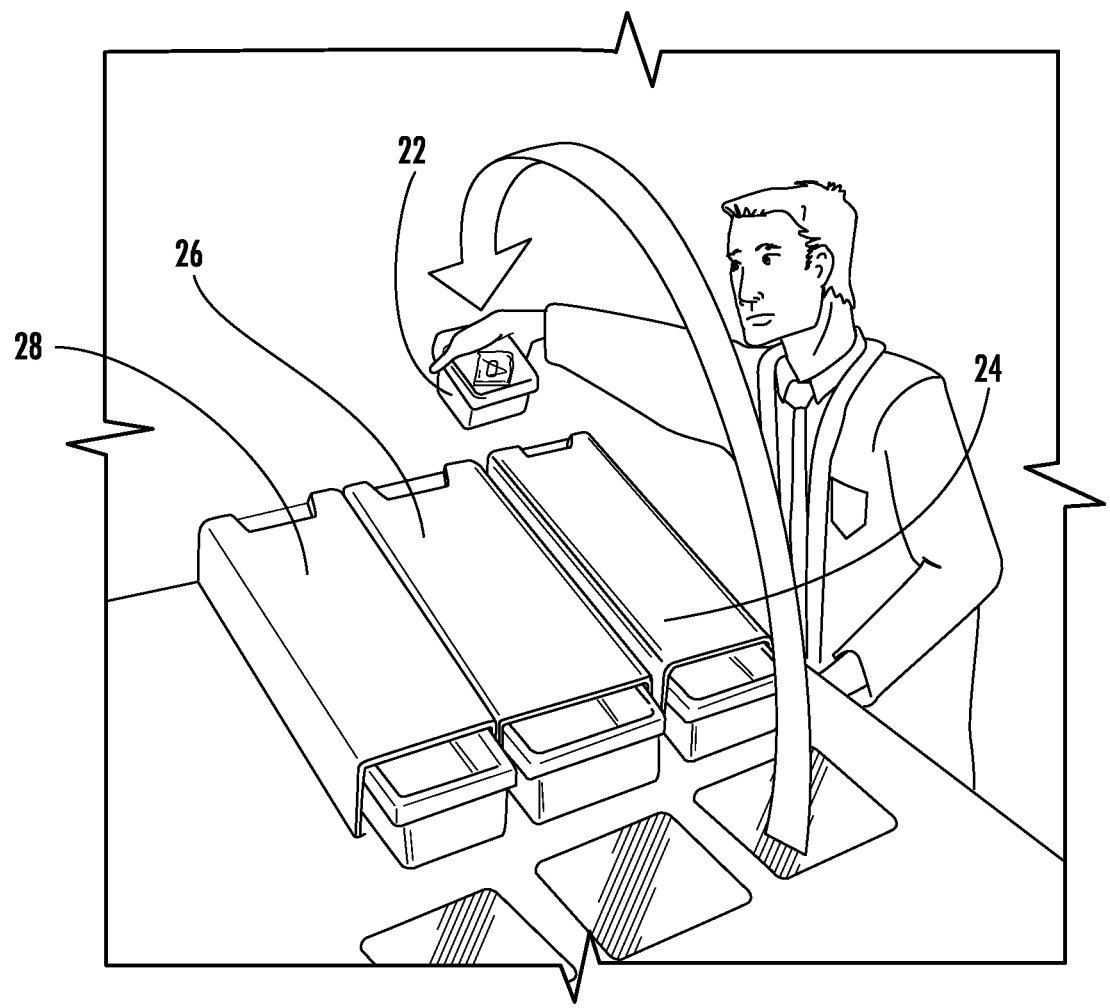
FIG. 13 depicts loading a magazine with a loaded overpack according to an example embodiment of the present invention.

As shown in FIG. 13, after the unit dose medication 20 is placed into the bin 22, the bin 22 is loaded into the back of the cassette 24 from which it was dispensed. The user may continue to scan medication unit doses and load them into bins until any of the cassettes 24, 26, 28 are full (i.e, no more empty bins). The full cassette may then be loaded to a transport device, such as a transport cart as described further below, for transport to a unit storage device.

Figure 14:
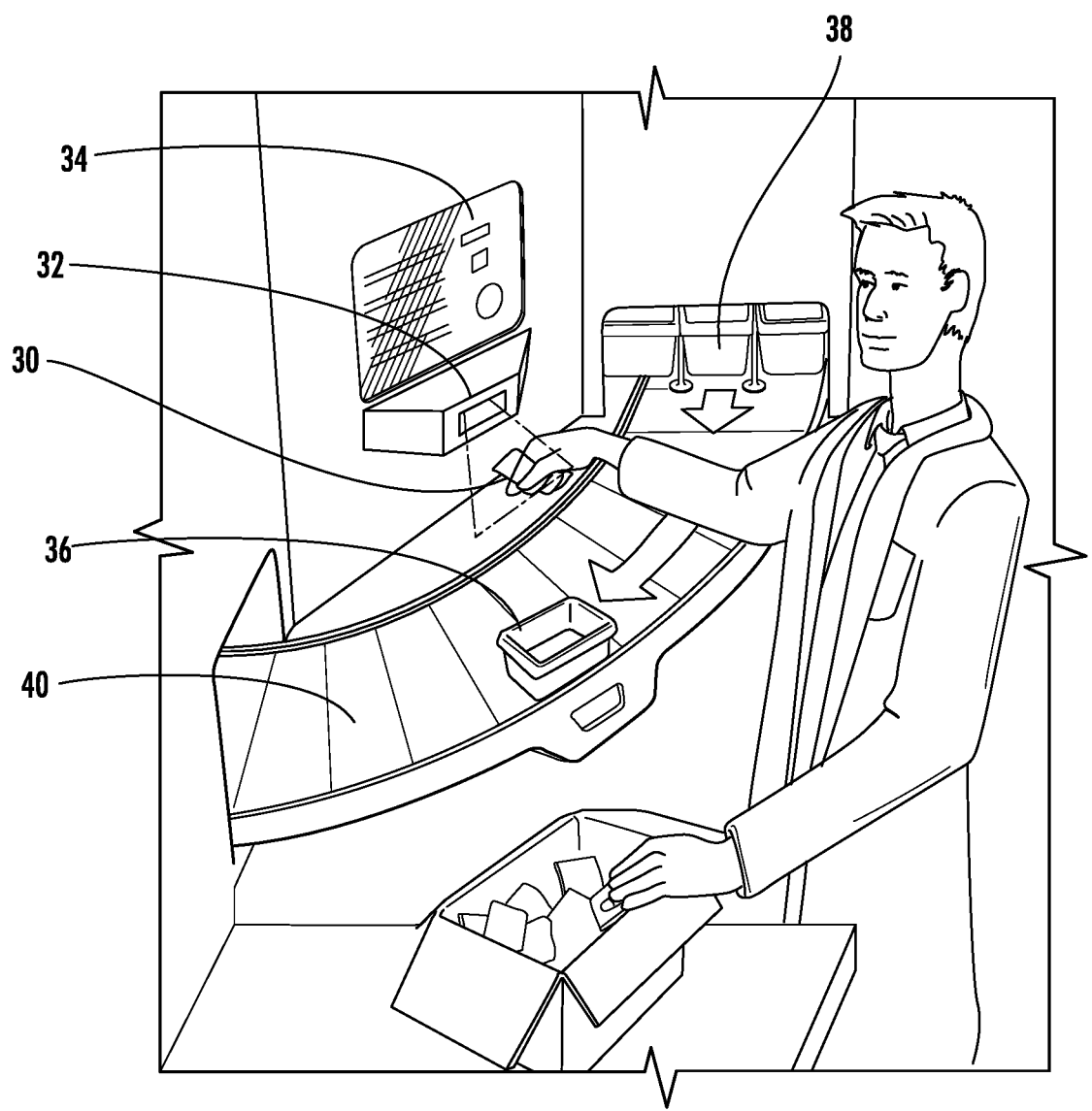
FIG. 14 illustrates another example embodiment of a system for selecting and loading overpacks.

FIG. 14 illustrates another example embodiment of a system for loading overpacks. In the illustrated embodiment, a unit dose medication 30 is scanned by a reader 32 configured to read one or more of a barcode, an RFID tag, or other identifying indicia. The identified unit dose medication may be displayed on user interface 34 allowing a user to confirm the identity of the medication. The user interface 34 may display information regarding the unit dose medication including an image thereof such that a user can confirm that the unit dose medication matches the displayed image. An appropriately sized bin may be automatically selected based on the unit dose medication identified and the appropriate bin 36 may be sent along conveyor 40 from a plurality of bins of varying sizes 38. Identifying indicia on the bin may be scanned upon being transferred from the plurality of bins such that the identity of the bin (e.g., a serial number) may be correlated to the unit dose medication that is loaded into the bin. In such a manner, the unit dose bin may be associated in a database with the medication contained therein, such that identification of the bin anywhere within the healthcare facility may also identify the contents, including such information as medication type, dose, expiration date, etc. The unit dose medication may then be loaded into the bin 36 as the bin is advanced to a device to load the bin onto a transport device (e.g., a cart, pneumatic tube, elevator, etc.).

Another example embodiment of loading unit dose medications into bins may be similar to that illustrated in FIG. 14; however the system may allow loading of multiple bins with the same type/dose of medication at the same time to increase efficiency. For example, if a user has seven unit doses of a particular medication, the first unit dose may be scanned by reader 32, and a quantity of unit doses may be entered on the user interface 34. Subsequently, the corresponding number of appropriately sized bins 36 may be transferred from the plurality of bins 38 to the conveyor 40. The user may then load all of the bins substantially simultaneously to increase efficiency by reducing the time required.

Figure 15:
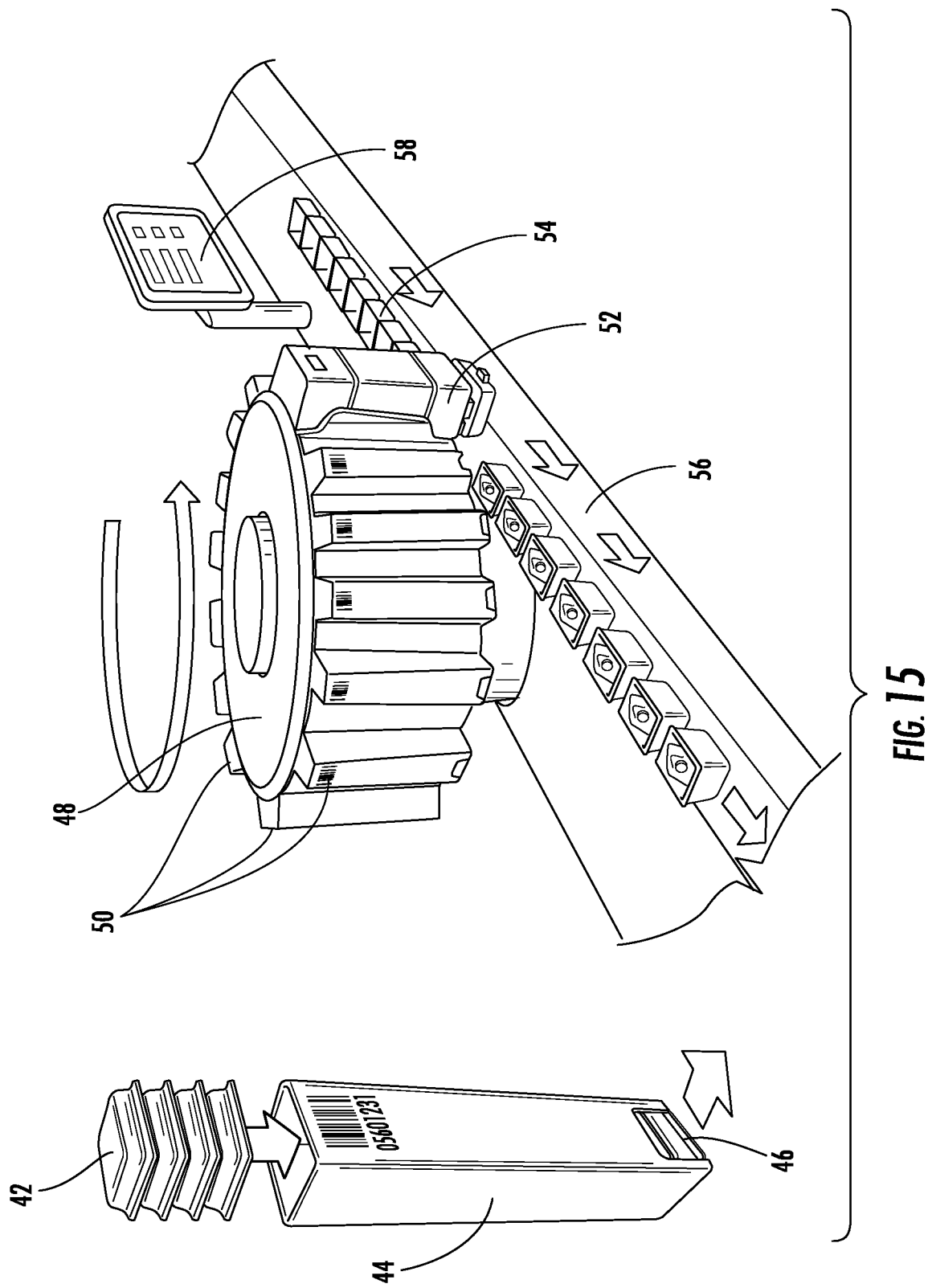
FIG. 15 illustrates a system for loading overpacks using a carousel containing a plurality of unit dose magazines according to an example embodiment of the present invention.

FIG. 15 illustrates an example embodiment of filling bins with unit dose medications automatically. A magazine 44 may be loaded with a plurality of unit dose medications 42. The magazine 44, and/or the medications stored there in 42 may include identifying indicia to identify the medication unit doses. Each magazine may include an orifice 46 through which the unit dose medications 42 are dispensed. A carousel 48 may include a plurality of magazines 50 disposed about the carousel 48. An automated dispenser 52 may be configured to dispense unit dose medications 42 from the plurality of magazines 50. As the carousel 48 rotates, different magazines 50, containing different unit dose medications (or optionally, additional supplies of a frequently used unit dose medications) may be rotated into alignment with the dispenser 52 for dispensing to unit dose bins 54 advancing along conveyor 56. The bins 54 may be identified by a reader configured to read identifying indicia from the bins and a database configured to correlate the dispensed unit dose medication with the appropriate bin. A user interface 58 may be provided to allow user monitoring, auditing, and intervention when necessary. In the example embodiment of FIG. 15, bins 54 may be loaded substantially automatically with little to no user input required.

Figure 16:
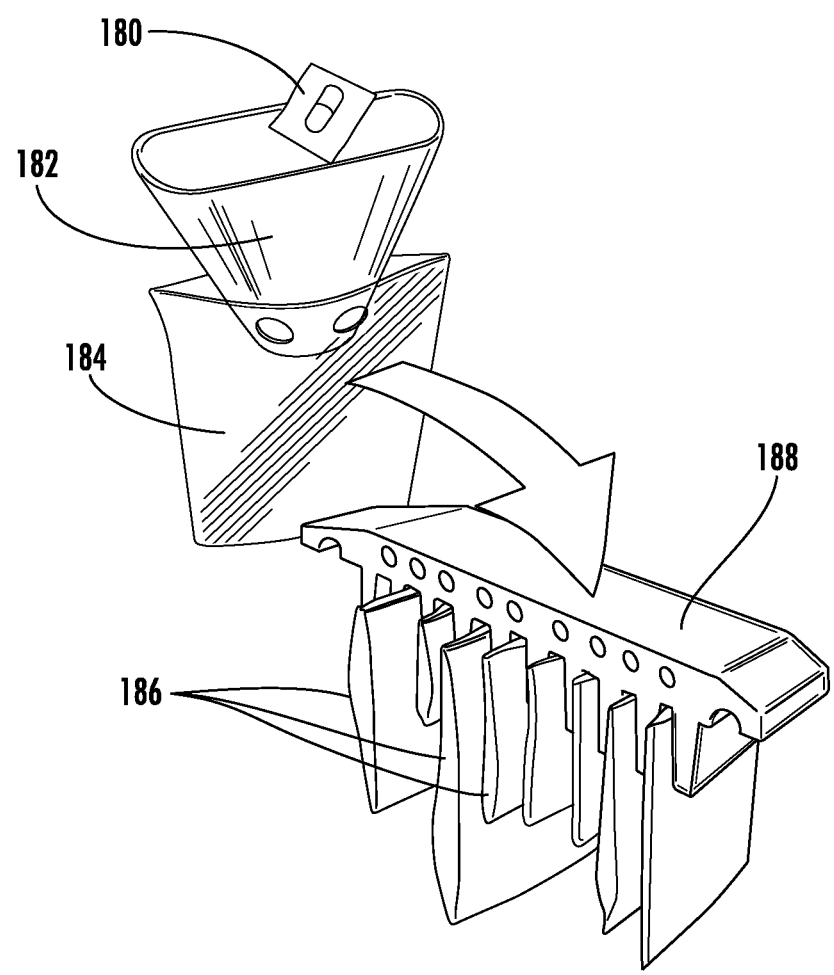
FIG. 16 illustrates an example embodiment of an apparatus to organize and transport medication and supplies according to the present invention.
Figure 17:
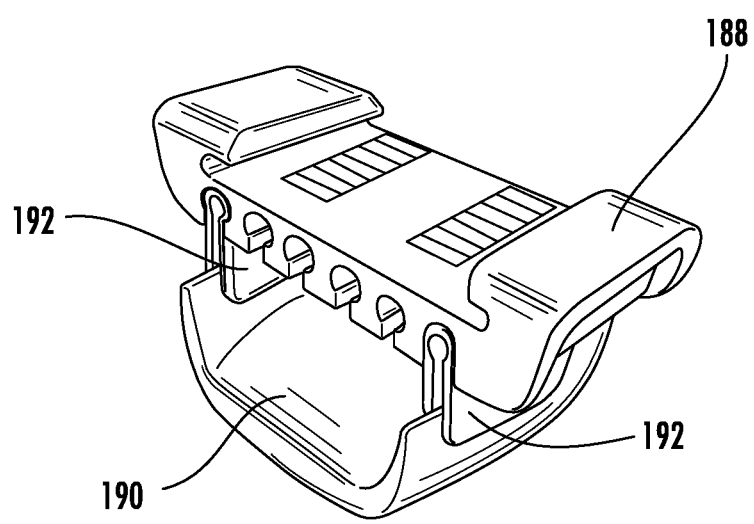
FIG. 17 illustrates the example embodiment of FIG. 16 adapted to carry and transport larger items.

FIG. 16 illustrates an example embodiment of an apparatus to organize and transport medication and supplies from a central pharmacy or from a remote pharmacy to local storage. The embodiment of FIG. 16 illustrates a unit dose of medication 180, which may be loaded into an overpack, in this case, a bag 184 using a bag filling device 182. The bag 184 may then be loaded into a clip of a carrier 188. The illustrated carrier includes a plurality of clips (not shown) which each hold a bag 186 type overpack. Rather than a tray as illustrated in FIG. 11, FIG. 16 uses a carrier in which the bags are suspended. As will be appreciated, the carrier can accommodate items of various sizes by receiving various sized bags within the clips. Alternatively, as illustrated in FIG. 17, items that are very large may be suspended by more than one clip. The carrier 188 of FIG. 17 is illustrated carrying a large item in a bag 190 with both ends of the bag suspended within clips 192.

Another example embodiment of organization of the overpacks in preparation for transport to a unit storage device may include bag-type overpacks that are disposed on a rod. FIG. 8 illustrates an example embodiment of an overpack 170 that is carried by rod 176. The rod 176 may be independently movable while holding a plurality of overpacks 170. For example, rod 176 may be received within a peg-board style apparatus for storage or transport. The rod 176 may include medications in overpacks for a single patient, and/or the rod may include medications for patients in a particular location. One advantage to an input organization apparatus of this type may include that an automated dispensing system, such as Robot-Rx™ may be configured to automatically load medications onto the input organization apparatus in preparation for distribution.

Transport to Unit Storage

According to example embodiments of the present invention, upon organization of the medications and supplies in overpacks into groups, the grouped articles need to be transported to a location proximate the patients, or at least closer to the patients than the central pharmacy, such as a unit storage device. The mode of transportation may vary according to the type of overpacks used, the type of input organization used, etc. Provided herein are means for transporting medications and/or overpacks from a central pharmacy to a unit storage device.

Figure 18:
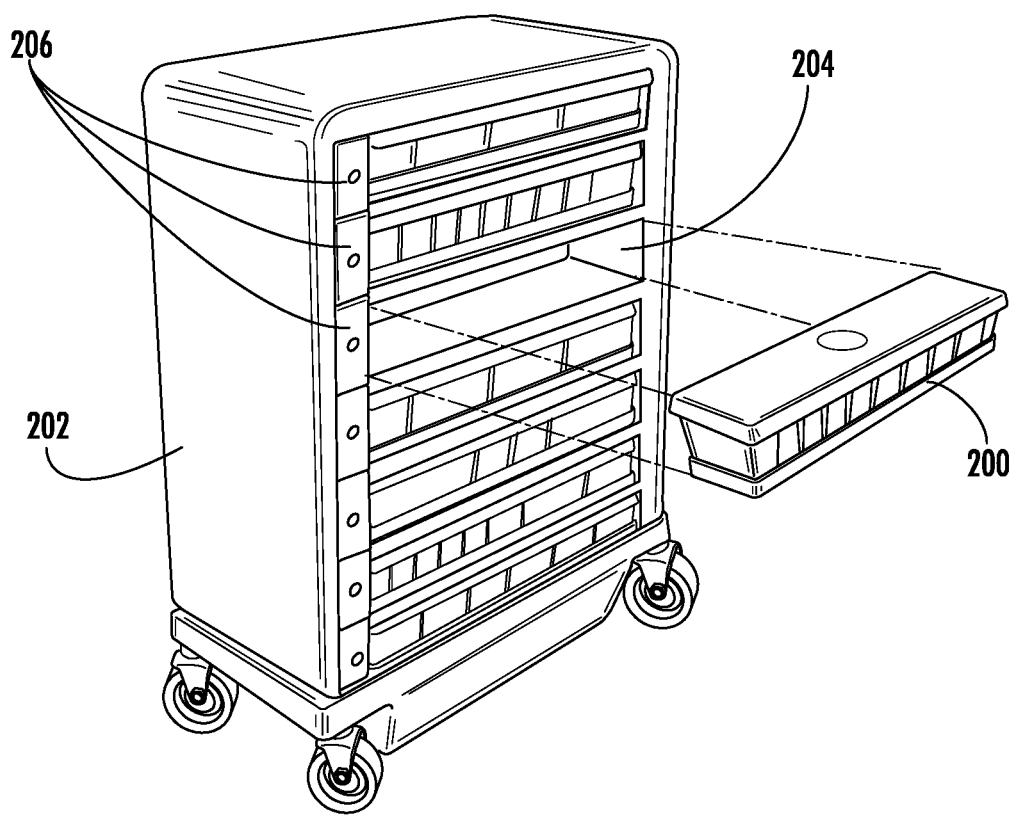
FIG. 18 illustrates an example embodiment of an apparatus configured to transport overpacks from a central pharmacy to a unit storage device.

An example embodiment of an apparatus used for transportation from the central pharmacy to the unit storage device is illustrated in FIG. 18 in which a lidded tray 200 is received within a transport cart 202. The lidded tray may be similar to that which is illustrated in FIG. 11 in which bins of varying size are received on a tray. While the illustrated embodiment shows a lidded tray 200, transport carts 202 may be configured to receive other types of overpacks and input organization devices.

The transport cart 202 may be configured with an RFID tag reader configured to read RFID tags associated with overpacks. In such an embodiment, the RFID tag reader or readers associated with the cart 202 may read the RFID tags of each of the overpacks received within the cart 202. Thus, the cart 202 may recognize the inventory stored therein for transport to a unit storage device. In some embodiments, the cart 202 may report the inventory via wireless communications to a network which monitors the location of the transport cart 202 and the contents therein. As such, an inventory control system may be configured to recognize and track the location of each overpack and unit dose medication or supply stored therein throughout the healthcare facility. Example embodiments of communication means and the networks over which such a system may operate will be described further below.

Additionally or alternatively, trays 200 may include identifying features such as RFID tags, barcodes, or other identifying indicia. Embodiments of the present invention may "build" a tray of overpacks by identifying the tray and filling the tray with identified overpacks. In such an embodiment, the tray may be tracked with an understanding of the contents of that specific tray.

Transport carts according to example embodiments of the present invention may be configured to be secure storage of the medications and supplies contained therein while transporting the articles from the central pharmacy to the unit storage devices. For example, as illustrated in FIG. 18, each tray 200 may be configured to be received within a shelf 204. The tray 200 may be configured such that individual bins or overpacks may not be removed from the tray 200 without the lid being removed. The shelf may include features or may be sized such that when a tray 200 is received within the shelf 204, the lid may not be removable. As such, the individual bins or overpacks may not be accessible without removing a tray 200 from the shelf 204. To prevent unauthorized removal of a tray 200 from the shelf 204, the cart may include a security feature to lock the trays into the shelves. The cart may include a single security feature or lock to lock all trays within all of the shelves simultaneously, or optionally, the cart 202 may include individual locks 206 for each shelf 204. Individual locks 206 for each shelf 204 may allow different authorized medical personnel access to different shelves. For example a medical staff person with a first level of authority may be authorized to remove trays 200 that do not contain controlled substances, while a medical staff with a second, higher level of authority may be provided access to shelves with trays containing the controlled substances.

The security features of carts 202 of example embodiments, whether for an entire cart or for specific shelves 204, may be configured to require a key, identification card, PIN, or biometric identifier to access the trays 200. In example embodiments in which the cart 202 is in communication with a network, a notification of access may be provided to the network in response to a tray being accessed. The notification may provide the identification of a user who accessed the tray to provide an audit trail of the medication and/or supplies of the tray from the central pharmacy to the unit storage device.

Transportation of carts from the central pharmacy to the unit storage device may be performed manually or may employ automation, or a combination thereof. For example, the cart 202 of FIG. 18 may include a drive mechanism and guiding features that allow the cart 202 to be an autonomous guided vehicle. The guiding features may include an apparatus configured to detect guide wires disposed within a floor of a healthcare facility, or the guiding features may include software with a functional knowledge of a healthcare facility layout and an ability to navigate the healthcare facility, among other autonomous guiding features.

In some example embodiments, the cart 202 may not include features to enable autonomous guidance and transport through the healthcare facility, but an autonomous guided vehicle may engage the cart 202 and guide the cart to the destination. In such an embodiment, the autonomous guided vehicle may be a compact, relatively flat device which slides under the cart 202 and guides the cart from underneath, thereby not increasing the footprint of the cart during transportation. In other embodiments, an autonomous guided vehicle may engage the cart 202 from a side, and push the cart through a facility to its destination.

Transportation of overpacks to a unit storage device may also include automated loading and unloading of the overpacks to the unit storage device. For example, a transport cart may engage a unit storage device wherein overpacks or a tray containing overpacks may be removed from the transport cart by a retrieval device, as outlined below. Such automated loading and unloading may allow transport carts to advance efficiently between unit storage devices without having to wait for manual unloading.

Figure 19:
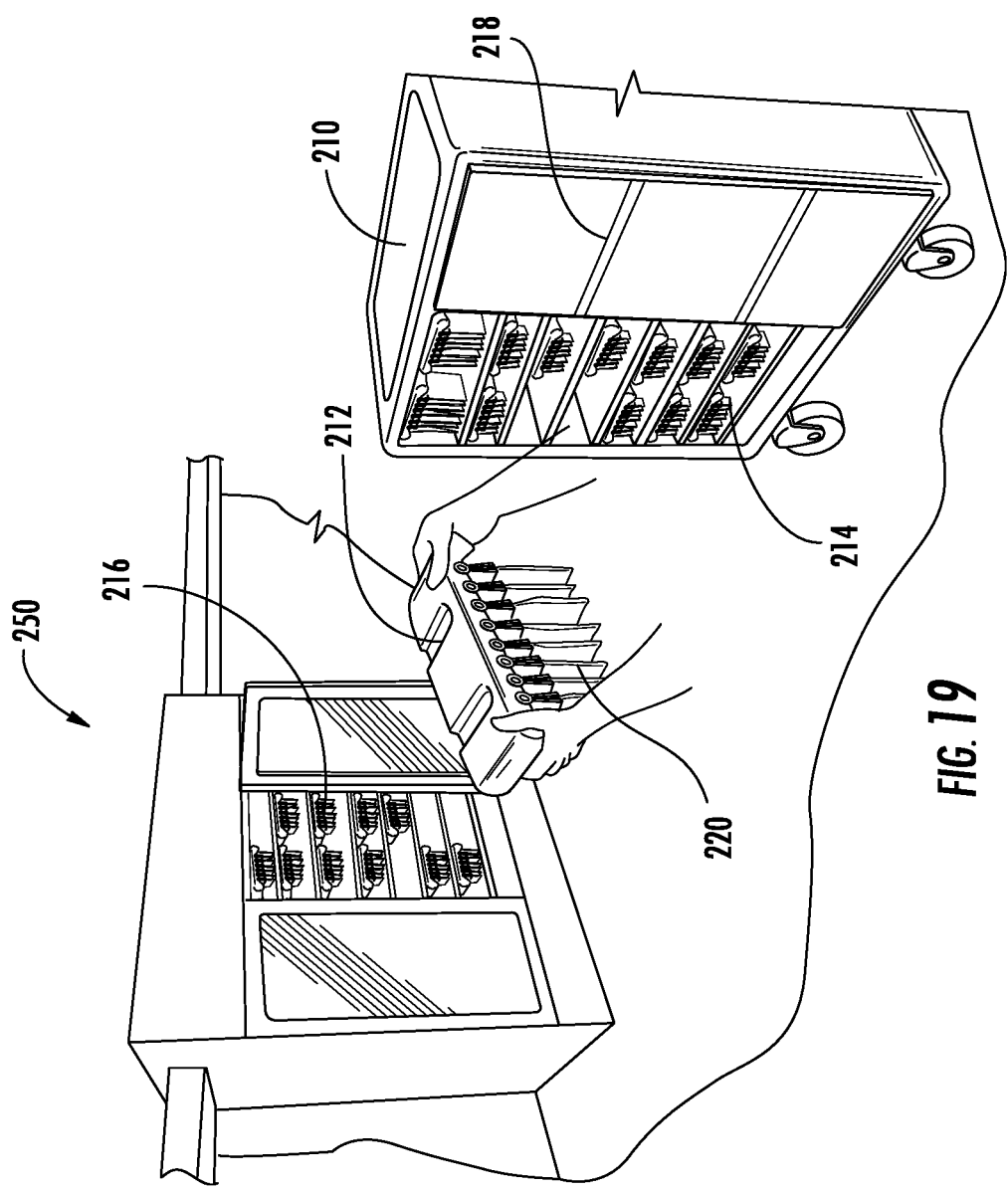
FIG. 19 illustrates another example embodiment of an apparatus configured to transport overpacks from a central pharmacy to a unit storage device.

FIG. 19 illustrates another example embodiment of an apparatus for transporting medications and/or supplies from a central pharmacy. The illustrated embodiment of FIG. 19 depicts a cart 210 configured to carry a plurality of carriers 214. In such an embodiment, the carriers may be suspended from shelves within the cart 210. The cart 210 of the depicted embodiment includes sliding doors 218 which may prevent unauthorized access by being lockable. Unlocking of the sliding doors may require identification of authorized medical personnel by identification card scanning, biometric scanning, PIN entry, or keyed entry. As outlined above with respect to FIG. 18, access to the cart 210 may be reported to a network for tracking of contents therein and for an audit trail related to the handling of the medication.

Example embodiments of cart-based transport devices may also include inventory stored thereon for replenishing as-needed medications and supplies in a unit storage device. Such inventory may be used to restock medications that have a low level of inventory at the unit storage device, or if expiring medications need to be replaced.

While the above embodiments describe cart-based transport from the central pharmacy to unit storage, other types of transport may be implemented. For example, medication overpacks may be transported to unit storage devices along track based transport systems, tube based transport systems (e.g., pneumatic tubes), elevators, or other transport systems which may be automated to varying degrees. Each of these embodiments may transport one or more overpacks at a time in dependence upon their implementation.

The efficiency of dispensing of medications and supplies within a healthcare facility may be improved by delivering the medications and supplies, including those that are known to be needed (e.g., previously prescribed) and those that are predicted to be needed, in groups to a location closer to the patients than the central pharmacy. This transportation maximizes resources, such as transport carts, while minimizing the required number of trips that must be made to deliver medications and supplies to units of a healthcare facility. Upon arrival at the healthcare facility unit, the medications and supplies may be dispensed to a local storage device that may further enhance the efficiency of distributing the medications and supplies to the patients.

Unit Storage

As outlined above, in order to more efficiently distribute medications to patients in a timely manner, it may be desirable to store medications for patients in a location closer to the patients than the central pharmacy. Further, as the majority of medications are used during only a portion of the day (e.g., 9 am-5 pm), relying on the central pharmacy to fill and distribute all medication orders directly to the patients may overburden the central pharmacy during the peak hours. Providing remote, local storage of medications for specific patients, as afforded by the predictive nature of example embodiments outlined above, allows a central pharmacy to fill medication orders and distribute medications and supplies off peak hours, ahead of the peak need for the medications. In order to support this method of distribution, unit storage devices may be employed in areas of healthcare facilities, such as in nursing units or hospital floors, for example. Embodiments of the present invention may include means for storing medications and/or overpacks at a location between the central pharmacy and the patient. The means for storing medication may also be configured with means for user interface and means for dispensing of the medications from the storage means.

An example embodiment of a unit storage device 250 is illustrated in FIG. 19 in which medications and supplies are received at the unit storage device 250 using input organization devices as outlined above. In the illustrated embodiment, carriers 212 with medications in bags 220 may be received at the unit storage device 250 and loaded into the interior 216 of the unit storage device. Each of the carriers 212 of the illustrated embodiment may be individually accessible within the unit storage device 250 such that medications for a particular patient may be easily accessed at any time. Further, when medications need to be removed from a carrier, or an entire carrier requires removal from the unit storage device, the carrier may be directly accessed for easy removal.

Figure 20:
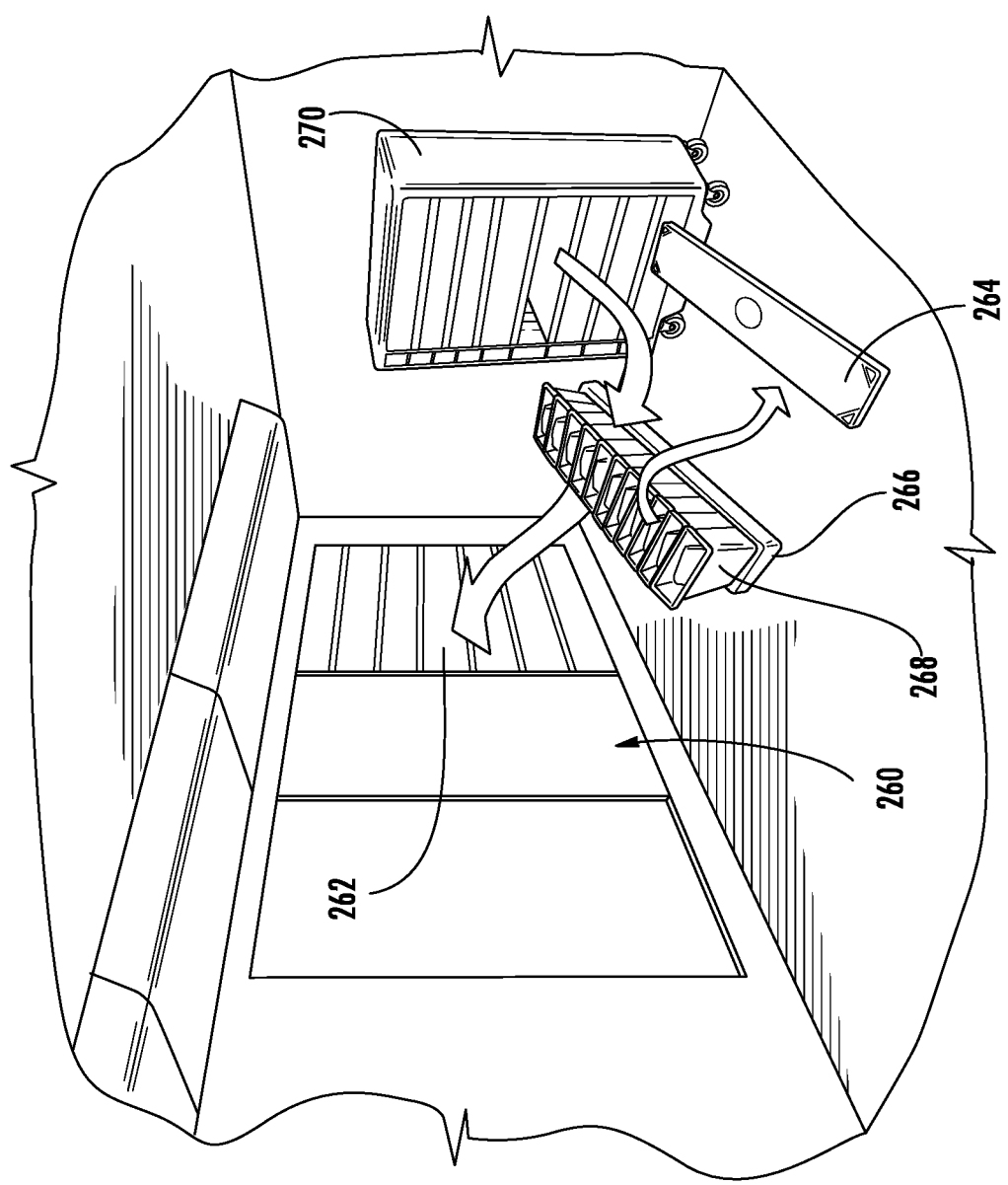
FIG. 20 illustrates a unit storage device supplied by an apparatus configured to transport overpacks from a central pharmacy according to example embodiments of the present invention.

FIG. 20 illustrates another example embodiment of a unit storage device 260 wherein a cart 270 transports trays 266 of overpacks 268, in this case various sizes of bins with a common profile. Upon removal of the tray 268 from the cart 270, the lid 264 may be removed, and the overpacks 268 may be loaded into the shelves 262 of the unit storage device 260. In some embodiments, the overpacks 268 may be removed from the tray 266 before loading into the unit storage device 260, while in other embodiments, the overpacks 268 may remain on the tray 266 to allow faster, more efficient loading.

As outlined above, the cart 270 may include features which allow the cart to report inventory to a network of the healthcare facility. Upon access to a tray 266 or carrier 212, the a communications interface of the cart 270 may provide an indication that a tray 266 or carrier 212 has been accessed, and removed for loading into a unit storage device. Similarly, the unit storage device may be equipped with a communications interface and an apparatus to detect the medications that are loaded therein. In response to receiving a tray, carrier, or medication/supply overpacks, the unit storage device may provide an indication to the network of the contents received therein for inventory tracking.

Unit storage devices according to embodiments of the present invention may have controlled access such that only authorized medical personnel may access the contents of the unit storage device for loading, unloading, or accessing the medications and supplies stored therein. Access may be granted to an authorized medical person in response to identification of the authorized medical person by identification card, PIN, biometric scan, or key. Further, the access may be reported via a communications interface to the healthcare facility network as appropriate.

Figure 21:
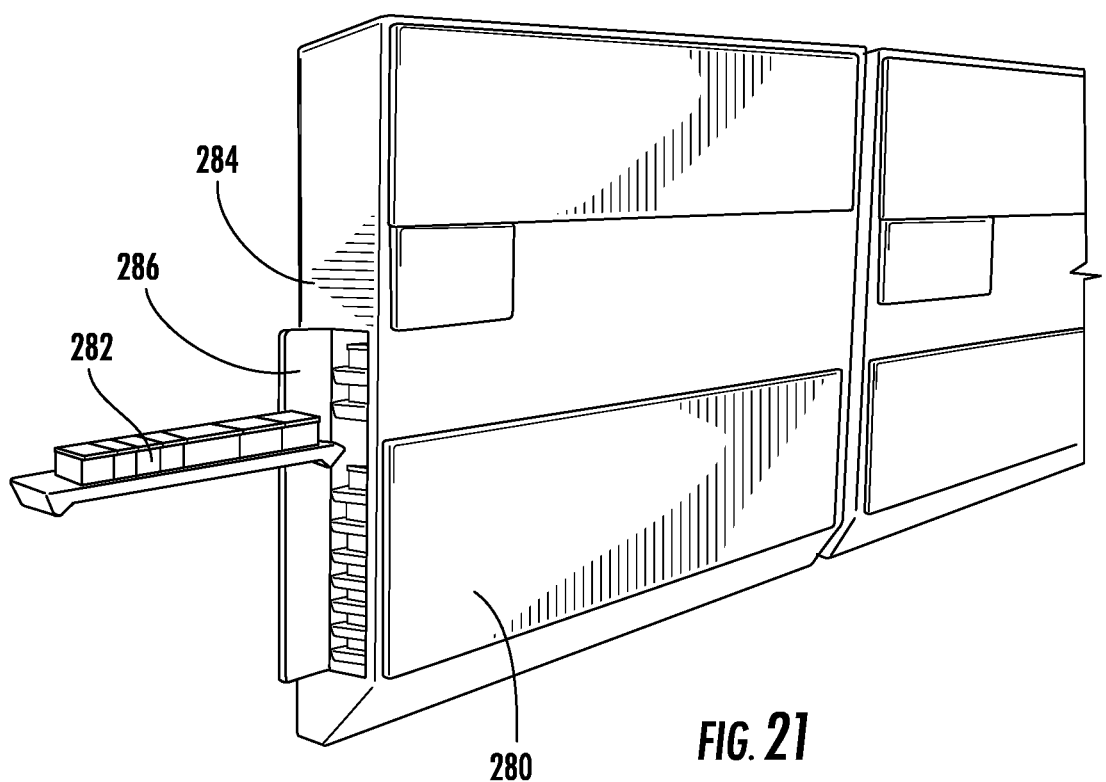
FIG. 21 illustrates another unit storage device according to example embodiments of the present invention.

FIG. 21 illustrates another example embodiment of a unit storage device 280 which may be loaded from a side of the unit storage device. In the illustrated embodiment, a tray of overpacks 282 may be inserted into a side 284 of the unit storage device 280 accessible through a door 286. One advantage to the illustrated unit storage device 280 may include that it has a shallow depth relative to a wall. For installation of unit storage devices into existing facilities, space in which to locate a unit storage device may be scarce. As such, when locating a unit storage device 280 in an existing hallway, a shallow depth may be imperative. Further, allowing the unit storage device to be loaded from a side 284 may allow the unit storage device to be loaded without encroaching into the hallway.

Unit storage devices of example embodiments may be configured to store medications and supplies in overpacks specifically designated for individual patients and they may be configured to store bulk medications which are not designated for individual patients. For example, a unit storage device may include the predicted medications for the patients in a unit of a healthcare facility needed over a particular period of time; however, certain as-needed medications may not be included in the predicted medications. Medications such as aspirin, antacids, etc. may be stored in unit storage devices for dispensing on an as-needed basis. Such medications may be provided to an authorized medical person at the unit storage device, or transported to a nurse server or patient server as detailed further below. The as-needed medication may be stored within a unit storage device in magazines, cartridges, spools of unit dose packages (e.g., separated by perforations), or the like.

Unit storage devices according to embodiments of the invention may have an inventory monitor or control, which may be implemented at the unit storage device, or remotely implemented configured to monitor inventory and information about the medication stored within the unit storage device. In this manner, the inventory monitor may monitor medications stored in the unit storage device for patients, and monitor inventory information regarding as-needed medication and supplies. For example, as-needed medications and supplies stored within the unit storage device may include lot numbers, manufacture dates, expiration dates, or the like. Inventory levels may be monitored for purposes of reordering medications and/or supplies to be delivered to the unit storage device. The inventory monitor may be configured to monitor a plurality of unit storage devices and monitor the use of particular medications or supplies at the various unit storage devices.

Medication that may be stored in unit storage devices for use on an as-needed basis, as opposed to patient-specific medication, may be stored in a unit storage device for a period of time. During storage, a particular as-needed medication may approach an expiration date. In response to approaching the expiration date, an inventory monitor may evaluate other unit storage devices to determine if any other unit storage devices within a healthcare facility use the particular as-needed medication at a higher rate. For example, an intensive-care unit may use more pain medication than a cardiac unit. In response to determining a higher rate of use of the particular as-needed medication at another unit storage device, the inventory monitor may be configured to direct a transfer of the medication approaching the expiration date to the unit storage device with a higher use rate of that medication. Such a transfer may reduce waste of medications that have expired and may reduce inventory costs.

An inventory monitor may also be able to predict upcoming shortages of a particular medication. For example, an urgent care unit may have a supply of flu vaccines. In response to an increase in flu cases, the inventory monitor may determine an increased need for flu vaccines and predict demand to outstrip current supply. In response, the inventory monitor may initiate a request for additional flu vaccines to be provided to the unit storage device. The request may be sent to a central pharmacy, for example. Should the central pharmacy not have sufficient inventory to meet the demand, the inventory monitor may initiate an order from a remote facility or distribution center.

Unit storage devices according to example embodiments of the present invention may also be configured to provide refrigerated storage. Some medications require refrigerated storage until they are ready to be administered. According to embodiments in which medications are temporarily stored at the unit storage device, such refrigerated storage may increase the shelf life of the medication and may allow the unit storage device to store refrigerated medications for a longer period of time than otherwise possible.

Figure 22:
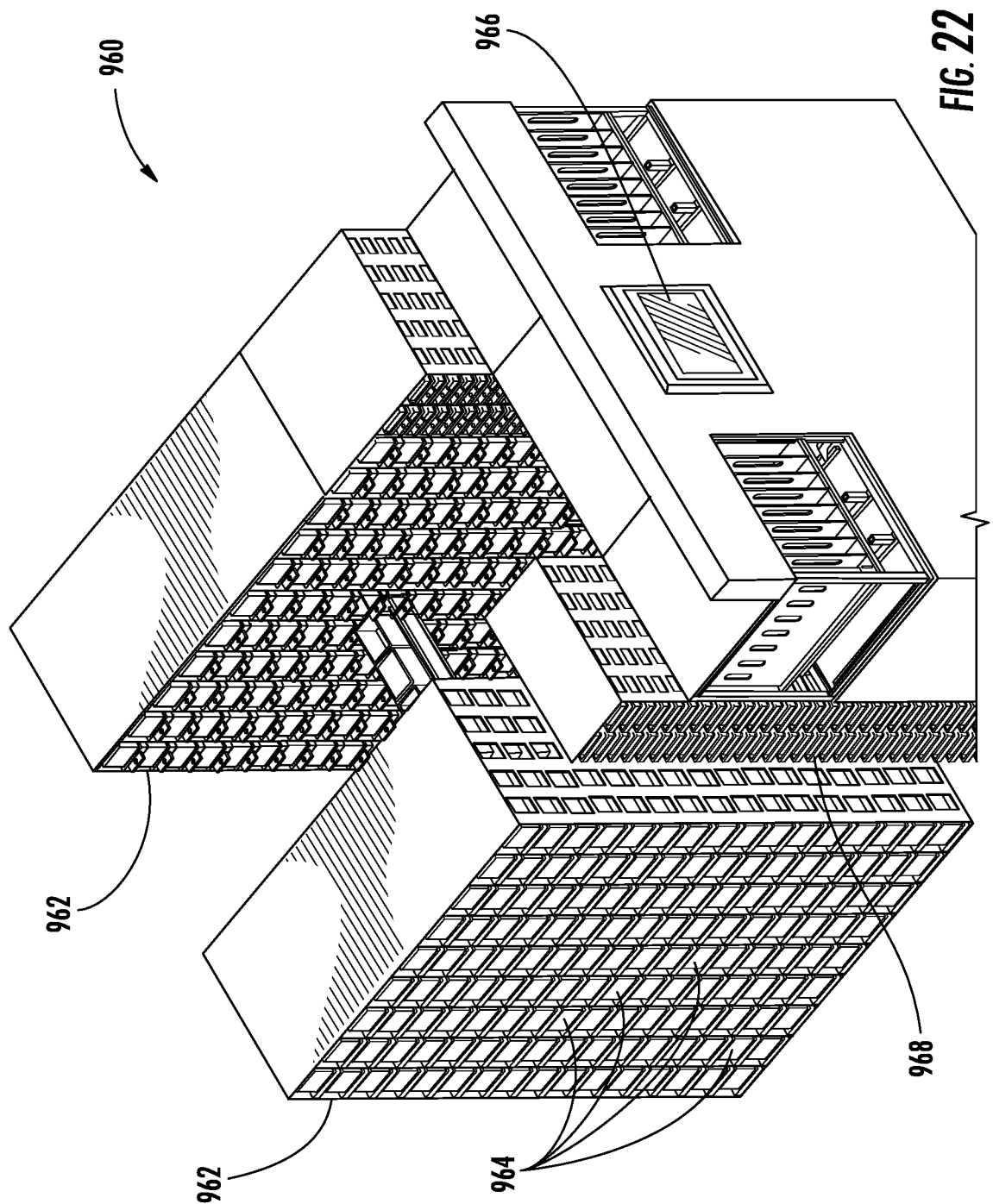
FIG. 22 illustrates an example embodiment of a high-capacity unit storage device.

FIG. 22 illustrates an example embodiment of a high-capacity unit storage device 960. The illustrated embodiment includes two banks 962 of shelves configured to hold a plurality of medication or supply overpacks. The overpacks of the illustrated embodiment may include a common profile (e.g., frontal width and/or frontal height) while having various sized depths to accommodate different sizes of items. For example, each of the overpacks may be a bin with a width of about four inches, and the depths may be two, six, or twelve inches. The banks may have a depth of about 24 inches, and each bank may have a plurality of compartments 964 configured to receive the overpacks. Each compartment 964 may hold overpacks totaling 24 inches in depth. In some example embodiments, overpacks may be grouped together in compartments of the banks according to the patient for whom they are intended. Additionally or alternatively, overpacks may be grouped together in compartments of the banks according to the size of the bins. For example, all twelve-inch deep bins may be stored in a particular area of the banks, while six-inch and two-inch deep bins may be grouped in a respective area of the banks.

A compartment may hold two twelve-inch deep overpack bins, four six-inch deep overpack bins, or twelve two-inch deep overpack bins.

The illustrated embodiment of FIG. 22 may further include storage of blister packs separate from the common-profile overpack bins. In the illustrated embodiment, blister pack storage 968 may be configured to hold in each compartment a tray of unit dose medications, each stored in a blister pack. As blister-packs are relatively common form factors, and since packaging a blister pack in an overpack bin may be less spatially efficient, the blister pack storage may allow more unit dose storage of blister packs in a smaller footprint.

The unit storage device of FIG. 22 further includes user interface 966 which may be used by authorized medical personnel to verify inventory, place medication orders, review medication order histories, etc. The user interface may allow orders to be placed for distribution to other locations, and may provide alerts and messages as will be described further below.

The illustrated embodiment of FIG. 22 may further include storage of as-needed medication. Such storage may be in the form of magazines (e.g., as shown in FIG. 9) or as-needed medication may be stored in compartments in the overpack bins. For example, aspirin may not be a medication that is specified on a medication order, but may be administered to patients on an as-needed basis. As such, one or more compartments of blister pack storage may be configured to hold unit-doses of aspirin. Such as-needed medication may be dispensed on request, with or without other medication orders.

While the unit storage devices illustrated in FIGS. 19-22 are configured to hold trays of overpacks or carriers, other example embodiments of unit storage devices are provided herein. For example, in an embodiment in which the input organization comprises a rod, as illustrated in FIG. 8, the unit storage device may include a peg-board style receiving area in which rods may be inserted for storage within the unit storage device. Unit storage devices according to further example embodiments may also be configured to use carousels which may include shelves, rods, or other storage means to accommodate the overpacks provided. Unit storage devices according to embodiments of the present invention may further be configured to receive overpacks without trays or carriers. For example, overpacks may be loaded onto shelves of a unit storage device as detailed further below.

Unit Storage Loading/Unloading

Unit storage devices according to example embodiments of the present invention may be configured to retrieve requested medications automatically in response to a request. For example once a unit storage device is loaded with the medications which are needed, or predicted to be needed on a unit during a period of time, the medications may be requested, or delivered in anticipation of a request, to a nurse server or patient server. In some embodiments, the unit storage device may be configured to dispense medications and supplies directly to authorized healthcare personnel at the unit storage device.

Figure 23:
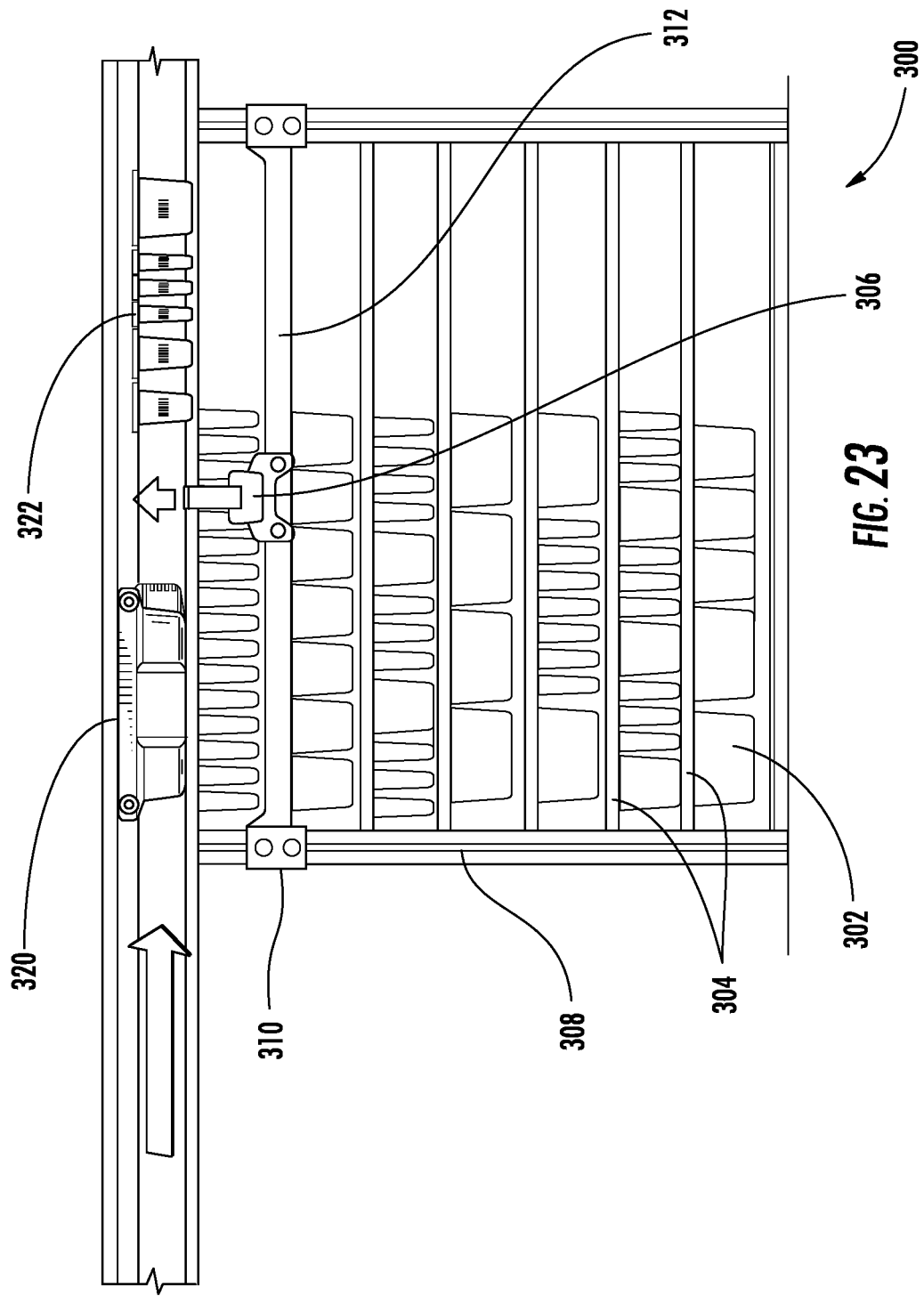
FIG. 23 illustrates another unit storage device including a retrieval device and a transport device according to an example embodiment of the present invention.

Embodiments of the present invention may include a means for retrieving requested medications in response to a request and means for loading medications onto or into a transport device. Embodiments of the present invention may provide a retrieving device for retrieving the requested medication or supply overpack from the unit storage device and a loading device to load the retrieved medication onto a transport device configured to transport the requested medication or supply to the nurse server or patient server. The retrieval device may be embodied in a number of different forms. FIG. 23 illustrates an example embodiment of a unit storage device 300 containing overpacks 302 of medication and/or supplies. The overpacks 302 of the illustrated embodiment are variable width bins; however, overpacks of many forms may be implemented with embodiments of the unit storage device and retrieval device described herein. The overpacks 302 are situated on shelves 304 within the unit storage device 300.

Additionally, while the illustrated embodiment of FIG. 23 illustrates a single layer of overpacks available for retrieval, further embodiments may include multiple layers of overpacks such that overpacks may be behind the first layer, requiring overpacks on the first layer to be moved to access the second layer, as shown in FIG. 22. In still other embodiments, the unit storage device may be two sided, such that two layers of overpacks are directly accessible to be retrieved by virtue of being arranged on both sides of the retrieval device.

The overpacks 302 of the illustrated embodiment of FIG. 23 may include identifying indicia disposed on the exposed, front side, such as barcodes, text, etc. The overpacks 302 may optionally include RFID tags for identification. The unit storage device 300 may determine the overpacks 302 stored therein by reading the RFID tags of the overpacks or by reading other identifying indicia of the overpacks when the overpacks are initially loaded into the unit storage device. As shown, the overpacks 302 may be arranged on a substantially vertical plane whereby each of the overpacks 302 is individually accessible and retrievable without requiring removal or movement of other overpacks.

The retrieval device of the illustrated embodiment includes an X-Y robot 310 configured to traverse the substantially vertical plane on which the overpacks 302 are arranged. The X-Y robot 310 of the retrieval device may include a retrieval unit 306 disposed on an X-axis arm 312. The retrieval unit 306 may be configured to move laterally along the X-axis arm 312 to access the width of the unit storage device 300. The retrieval unit may be configured with a drive mechanism to advance laterally along the X-axis arm. For example, the retrieval unit may include a pinion gear that is rotated by an electric motor, where the pinion gear of the retrieval unit 306 engages a rack gear disposed along the length of the X-axis arm. A rack-and-pinion gear arrangement would afford the retrieval unit 306 precise indexing capabilities desirable for repeatably retrieving overpacks accurately. Alternatively, the X-axis arm may include a belt or chain-drive mechanism which advances the retrieval unit 306 along the X-axis arm as a carriage. Such an embodiment may move the drive mechanism from the retrieval unit to a mechanism located on the X-axis arm, providing a smaller, potentially more nimble retrieval unit.

The X-axis arm may be movable along the Y-axis along a pair of vertical columns 308. While the illustrated embodiment includes a pair of vertical columns 308, embodiments may implement a single vertical column. Further, the vertical columns 308 illustrated are disposed at the distal edges of the unit storage device 300; however, the vertical columns 308 could be disposed anywhere along the width of the unit storage device. The X-axis arm may be configured to move vertically along the columns 308 by one or more pinion gears disposed on the X-axis arm, engaging one or more rack gears disposed on one or more of the columns 308. Optionally, the X-axis arm may be advanced along the columns 308 by a chain or belt drive disposed in or on the columns 308 moving the X-axis arm as a carriage.

While the above described and illustrated embodiment of an X-Y robot retrieval device includes stationary columns 308 and a movable X-axis arm, example embodiments may include a movable Y-axis arm and one or more stationary X-axis arms arranged at the top and/or bottom of the unit storage device.

The retrieval unit 306 may be configured with a scanning device configured to scan identifying indicia of the overpacks 302. The scanning device may include a barcode scanner, an image detection device, or an RFID tag reader, for example. The retrieval unit 306 may be configured to identify the overpacks and their locations within the unit storage device upon loading of the overpacks into the unit storage device. For example, when a tray of overpacks is loaded into a shelf of the unit storage device, in response to the unit storage device being closed (i.e., a loading door being shut), or in response to a user command, the retrieval device may advance along the shelves of the just-loaded overpacks and scan each of the overpacks for identifying indicia. Upon identifying an overpack, the retrieval device may store the location and contents of the overpack.

The X-Y robot 310 and retrieval device 306 may also be configured to organize or arrange overpacks within the unit storage device. For example, upon loading of the unit storage device, software may determine a more appropriate layout for the overpacks contained within the unit storage device. Some medications may require refrigeration, in which case those overpacks may be moved to a refrigerated section. Further, overpacks may be grouped according to a time frame in which the medications contained therein may be needed. As such, the X-Y robot 310 may optimize the layout of the overpacks to increase the efficiency of retrieval and distribution of the medications.

In response to receiving an indication of the need of a particular medication, or all of the medications for a particular patient or group of patients, the retrieval device may commence the retrieval process in which the required medications are retrieved. The retrieval device may advance along the X and Y-axes of the unit storage device to the location of the first overpack to be retrieved. Upon arrival at the location of the first overpack to be retrieved, the retrieval unit 306 may scan the identifying indicia of the overpack to confirm it is the correct overpack intended to be retrieved. In response to a positive confirmation, the retrieval unit may retrieve the overpack from the location. The retrieval may be in the form of pulling the overpack from the shelf and sliding the overpack onto a holding surface of the retrieval unit 306. Optionally, the retrieval unit may be configured with a grasping device configured to grab and hold the overpack to advance the overpack to the transport device, described further below.

In response to retrieving the first overpack to be retrieved, the retrieval unit 306 may be advanced by the X-Y robot to a location within or adjacent to the unit storage device for loading onto a transport device 320. Optionally, the retrieval unit 306 may position the retrieved overpack in a staged position ready to be placed onto a transport device as illustrated at 322. In the example embodiment of FIG. 23, the transport device 320 may be located above the unit storage device 300, configured to advance along a channel proximate the ceiling as will be described further below.

In some example embodiments, the retrieval device may retrieve the overpack and place the overpack in a staged position awaiting the transport device. In such an embodiment, a loading device may be configured to load the overpacks onto the transport device. The loading device may be as simple as a mechanism by which overpacks are pushed or pulled onto the transport device. Additionally or alternatively, the transport device may include the loading device, whereby the transport device is configured to load the overpacks onto the transport device. The retrieval device may also operate as the loading device, configured to retrieve the overpacks and load them directly onto the transport device.

Figure 24:
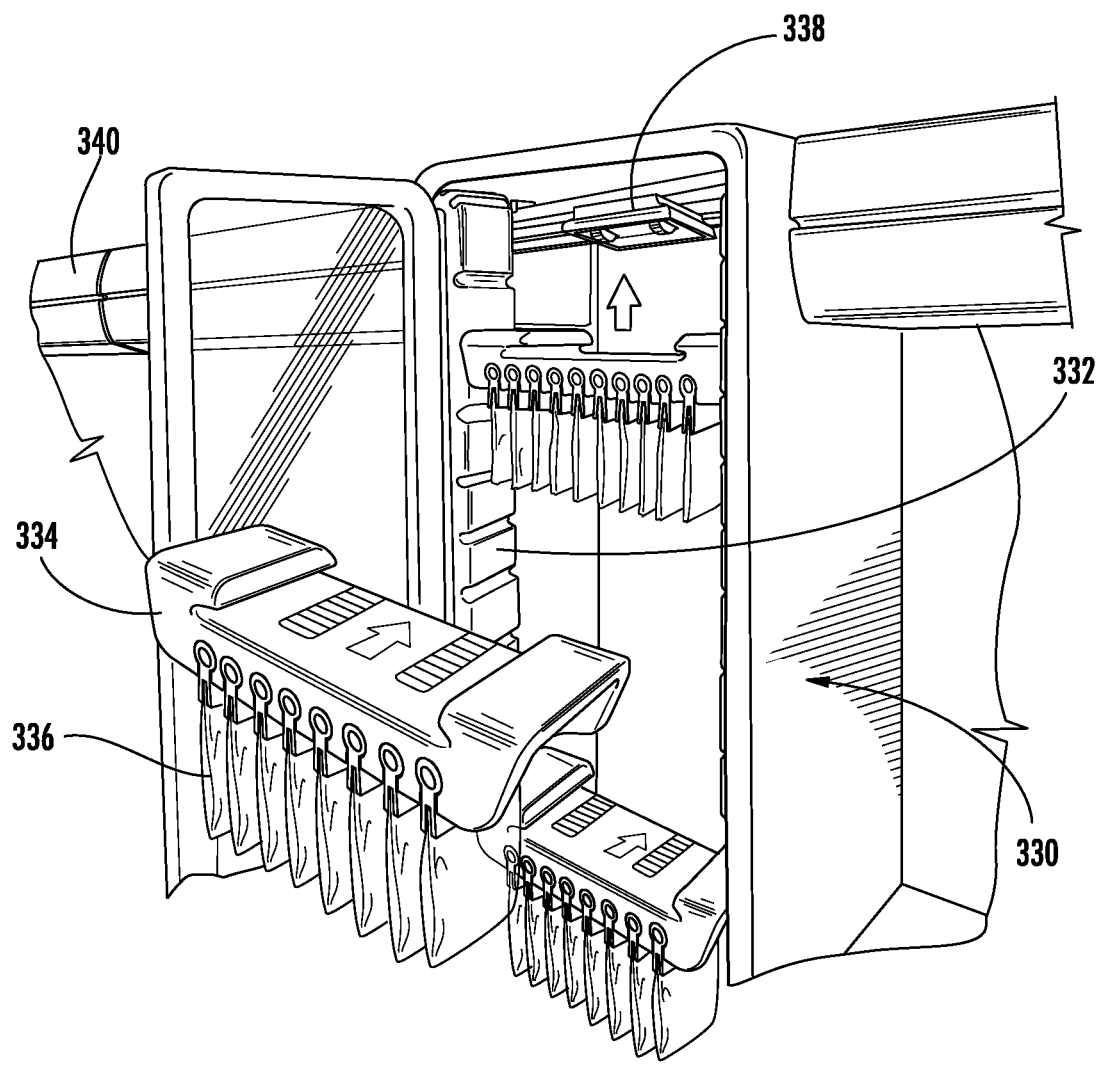
FIG. 24 illustrates a unit storage device including a loading device according to an example embodiment of the present invention.

While the illustrated unit storage device is configured to temporarily store overpacks of medications and supplies awaiting delivery to a location proximate a patient, embodiments of the unit storage may also include devices arranged to load transport devices with overpacks upon their arrival at the unit storage. For example, as illustrated in FIG. 24, the unit storage device 330 may be implemented as a loading device to load a transport device. The illustrated embodiment includes a unit storage device 330 including a conveyor system 332 configured to receive a carrier 334 holding a plurality of overpacks 336. Once the carrier 334 is loaded into the conveyor system 332, the conveyor advances the carriers 334 toward a shuttle 338. The shuttle 338 is configured to advance the carriers along a path defined by a track along which the shuttle 338 rides. The track may be disposed within an area proximate the ceiling of a healthcare facility unit and may be enclosed as illustrated at 340.

Figure 25:
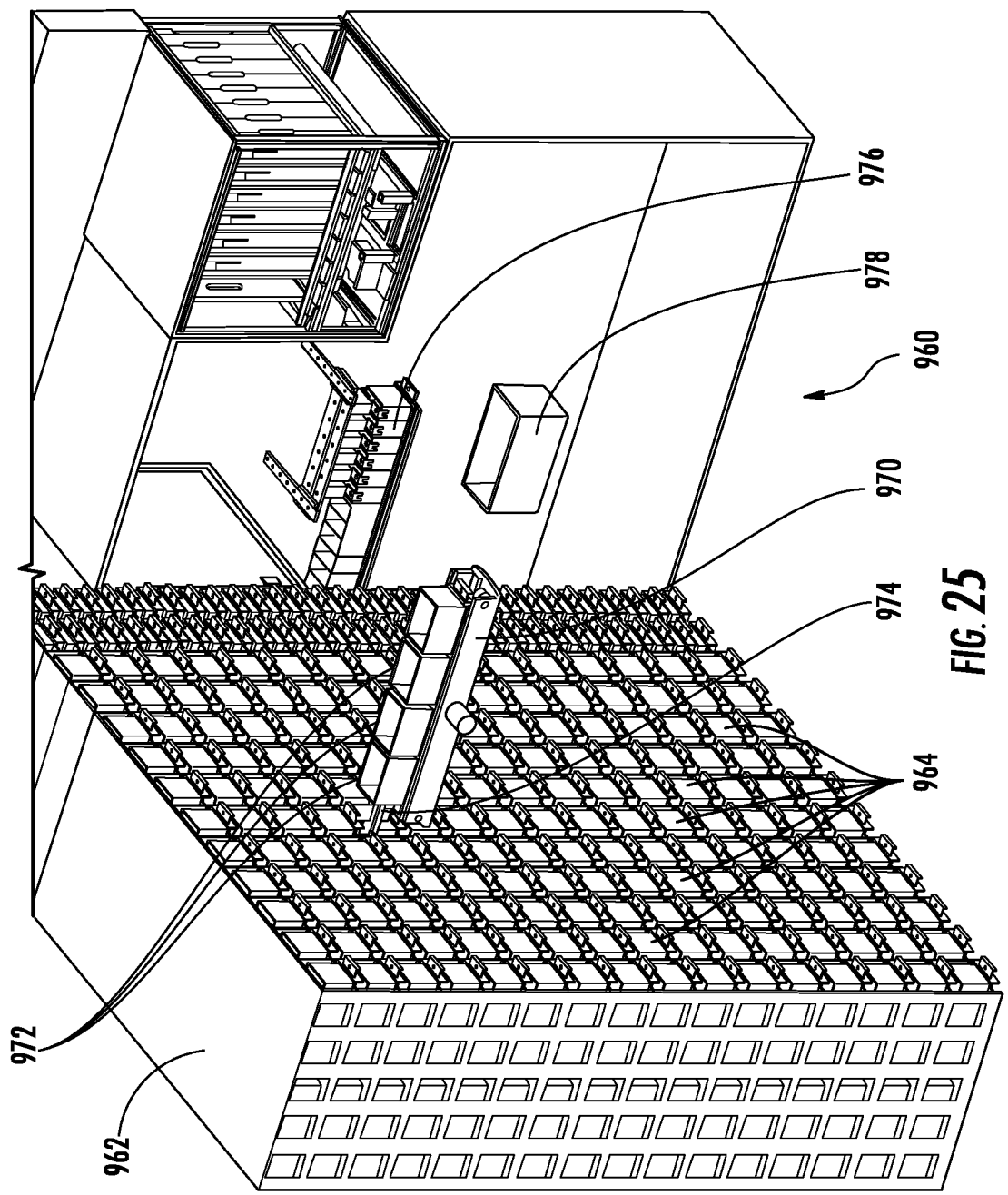
FIG. 25 illustrates a method for loading and dispensing overpacks from a high-capacity unit storage device according to example embodiments of the present invention.

FIG. 25 illustrates another view of the example embodiment of the high-capacity unit storage device with one of the banks 962 omitted for ease of understanding. In the illustrated embodiment, an end-of-arm-tool (EOAT) is configured to be attached to a mechanism, such as a robot arm or an X-Y robot, and moved into alignment with any of the compartments 964 of the banks 962. The mechanism for moving the EOAT between compartments is not shown in the illustrated embodiment. The EOAT of the illustrated embodiment is configured to be a retrieval device arranged to withdraw overpacks 972 from their respective compartment 974. As shown, the EOAT has retrieved four medium sized overpacks 972 from compartment 974.

In practice, a request for medication and/or supplies may be received at the unit storage device 960. The request may be received automatically from a network entity configured to request medications in anticipation of their need. Requests may also be received from the user interface 966 of the unit storage device 960, a nurse server, patient server, nurse cart, workstation, or mobile device. Upon receipt of the request, the unit storage device may be configured to fill the medication order by retrieving each of the medications and supplies that are requested. The EOAT may be moved into alignment with a compartment 964, 974 containing one or more of the requested medications or supplies. The EOAT may retrieve the overpacks 972 of the compartment, which may include overpacks that do not contain medication or supplies that are part of the order. The EOAT 970 may move the retrieved overpacks 972 to a dispensing area 976 of the unit storage device 960. The dispensing area 976 may include a mechanism for removing the overpacks 972 containing medications or supplies that are part of the order from the EOAT 970. Overpacks 972 containing medications or supplies that are not part of the order may remain on the EOAT 970. The EOAT 970 may then return the overpacks 972 not needed, and retrieve any additional overpacks from any additional compartments which may contain medication or supplies that are part of the medication order. The additional overpacks may be grouped with the previously retrieved overpacks until all of the overpacks containing medication or supplies in the request are retrieved.

The overpacks containing the medication or supplies in the request are grouped and may be transported to a nurse server or patient server by a transport device as described further below, or dispensed from the unit storage device to an authorized medical person. While the above described embodiment includes grouping the overpacks, in another example embodiment, the overpacks containing the medication and/or supplies may be emptied at the dispensing area 976 to a patient-specific container 978. The emptied overpacks may then be returned to their compartment with any unused overpacks, or alternatively, returned to an empty-overpack return area for subsequent return to the central pharmacy. The patient specific container 976 may be transported to a nurse server or patient server, or optionally, dispensed from the unit storage device to an authorized medical person.

Figure 26:
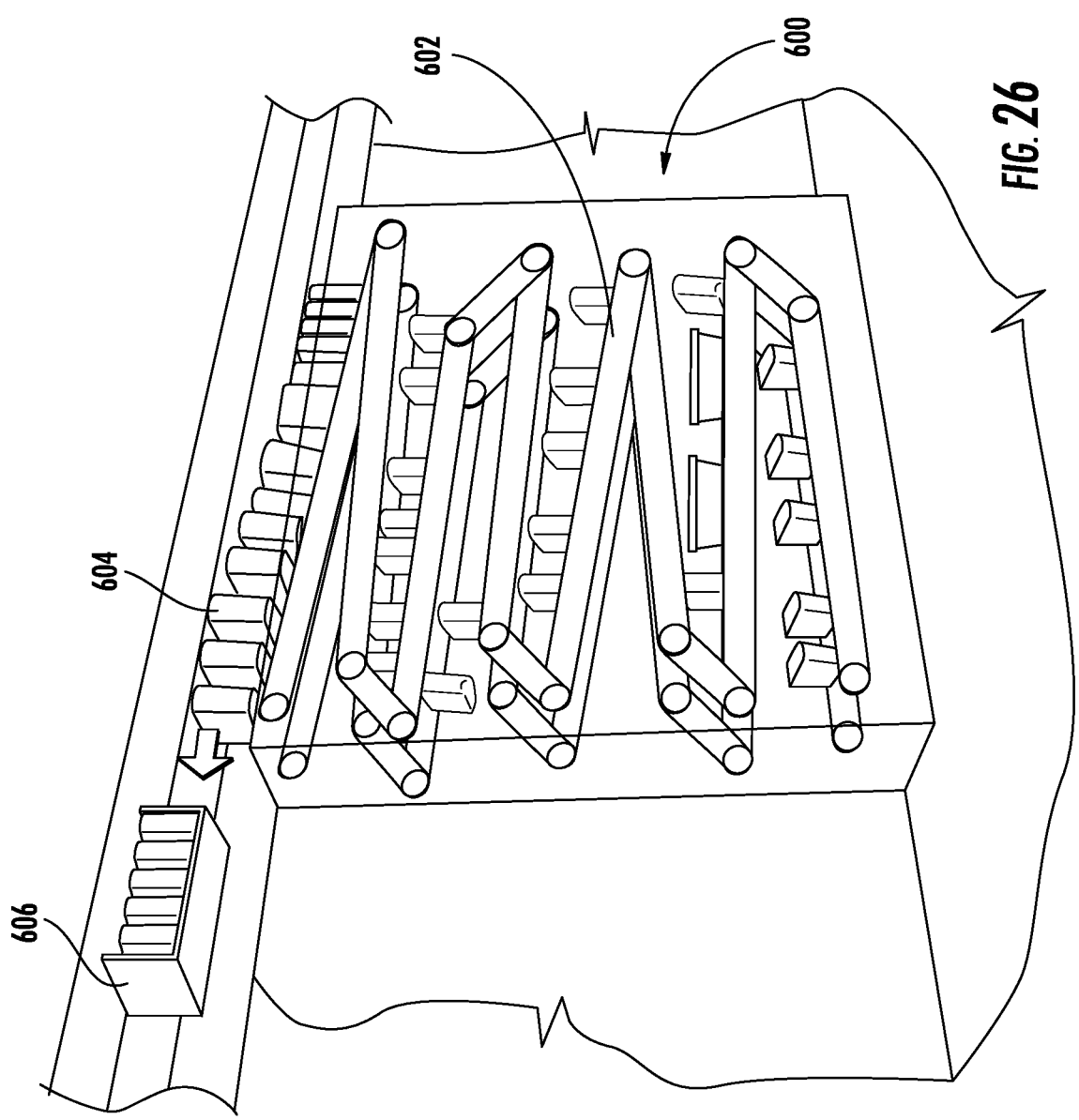
FIG. 26 illustrates a unit storage device according to another example embodiment of the present invention.

FIG. 26 illustrates another example embodiment of a unit storage device 600 which is configured to load a transport device 606 with overpacks for transport to a location closer to the patient for whom the medication or supplies are intended. The unit storage device 600 of FIG. 26 may not be configured for static storage of overpacks, but instead receives a plurality of overpacks and queues them for transport to a nurse server or patient server. In the illustrated embodiment, a serpentine conveyor 602 advances overpacks received at the unit storage device 600 to a staging area 604 where the overpacks await a transport device 606 to transport the overpacks to the appropriate nurse server or patient server. Embodiments according to the illustration of FIG. 26 may be configured to be very narrow and thus may be used in facilities in which floor space is limited. The embodiment of FIG. 26 may protrude only minimally from the wall to allow installation in hallways or quarters where minimal space is available.

Overpacks may be loaded into the unit storage device 600 grouped according to their destination such that they may be loaded onto transport devices in groups. Optionally, in embodiments in which the overpacks are not grouped according to destination, a scanner within the unit storage device 600 may scan identifying indicia of the overpack to determine destination, and subsequently load each overpack onto a transport device destined for that destination. The unit storage device may assign a destination to a transport device once enough overpacks to fill the transport device have been scanned. Alternatively, if there are not enough overpacks to fill a transport device and the time waiting for enough overpacks has exceeded a predefined threshold, the overpacks may be loaded to a transport device and sent to their destination without the transport device being full.

Figure 27:
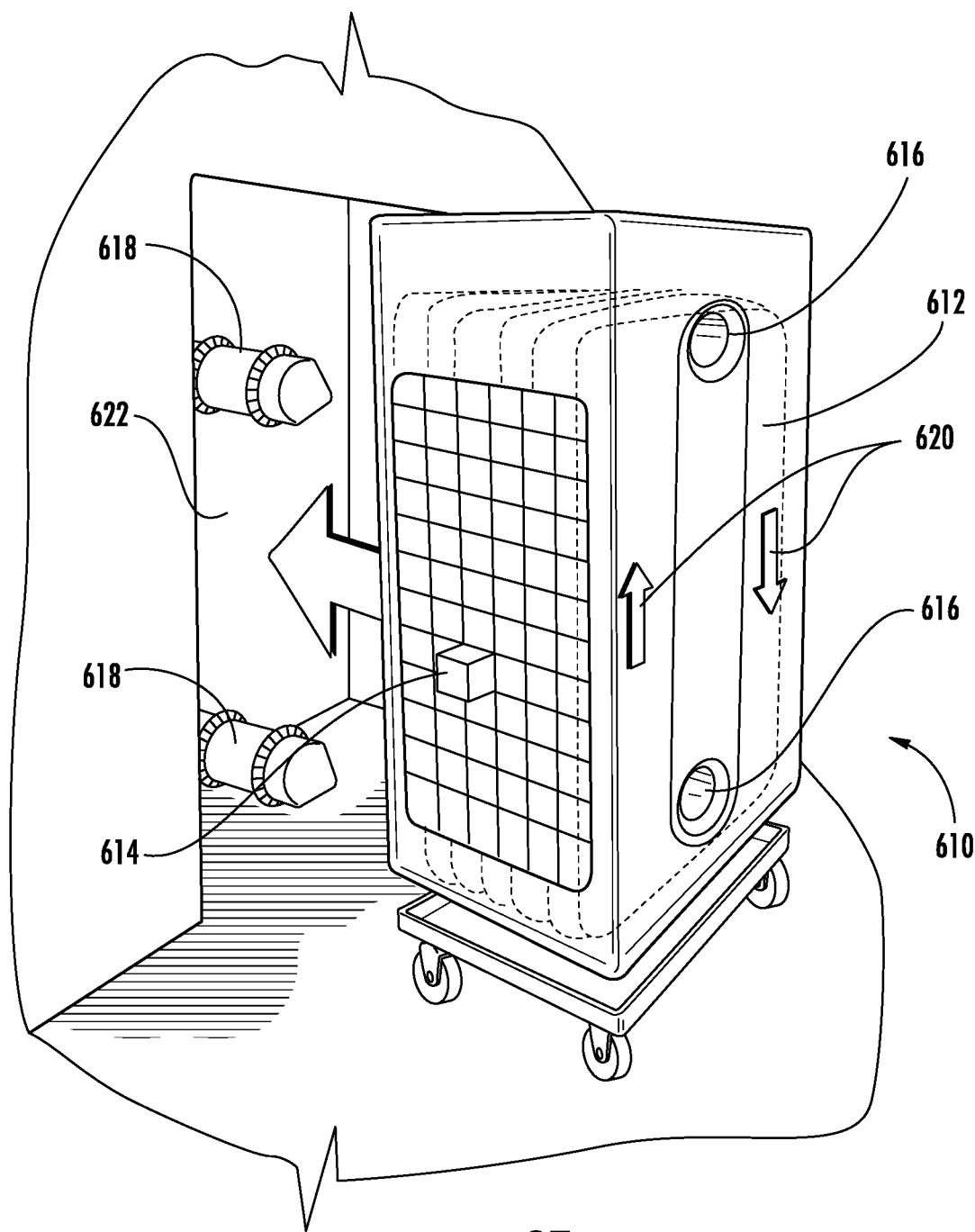
FIG. 27 illustrates a unit storage device according to yet another example embodiment of the present invention.

FIG. 27 illustrates another example embodiment of a unit storage device 610 which may be transportable from the central pharmacy to the unit of the healthcare facility. In the illustrated embodiment, a cart including a carousel that rotates as shown by arrows 620 may include a plurality of bins 614 or locations where overpacks may be loaded at the central pharmacy. The unit storage device 610 may be mobile such that upon loading at the central pharmacy, the device 610 may be transported (e.g., manually or via AGV) to a unit of the healthcare facility. A unit storage device receiver 622 may be located on the unit configured to receive the unit storage device 610 therein. The unit storage receiver 622 may include a door or may be substantially closed off in response to receiving the unit storage device 610. The unit storage receiver may also include spindles 618 configured to be received within bores 616 of the unit storage device. The spindles 618 may rotate within the bores 616 to turn the carousel. The carousel may be rotated to provide access to each of the overpacks stored therein. An automated retrieval device, such as the X-Y robot described above, or potentially a single-axis robot, may retrieve the overpacks from the carousel and load them onto a transport device for transport to a location proximate the patient to whom the medication or supplies are to be administered.

While the illustrated embodiment depicts a mobile unit storage device 610 including a carousel, embodiments may include only a cart with the overpacks stored thereon, where the cart may be received at a unit storage receiver and a retrieval device may retrieve the overpacks from the unit storage device as needed. Further, while the embodiment of FIG. 27 relies on the rotating mechanics of the spindles 618 to be disposed in the unit storage receiver 622, further embodiments may include a motive mechanism within the unit storage device 610. The unit storage receiver 622 may provide power, such as an electrical connection, to power the motive mechanism of such a unit storage device.

Further example embodiments of unit storage devices may include dynamic shelves (i.e., movable shelves) that may be loaded as outlined above with respect to static shelves. While an X-Y robot may be employed to load/unload static shelves in a unit storage device as outlined below, dynamic shelves, such as a carousel with a vertical axis of rotation, may allow a robot configured only to move in a Y-axis to access all of the shelf locations of the unit storage device as the carousel rotates.

Unit storage devices according to example embodiments of the present invention may also be configured to present overpacks directly to an authorized medical person in response to receiving a request. For example, a nurse may be aware of an immediate need for a medication for a patient and may be near the unit storage device. The nurse may request the medication via user interface or via a remote device (e.g., a mobile device or nurse cart). The unit storage device may be configured to present the requested medication to the nurse in response to receiving the request.

Transport to Proximate Storage

As outlined above with regard to the carrier including a plurality of bag-type overpacks, a shuttle may be configured to advance the carrier to a second location, which may include a nurse server or a patient server as will be detailed further below. The shuttle 338 of FIG. 25 may be configured to advance along a track to the nurse server or patient server, each of which will be detailed further below.

Embodiments of the present invention provide various means for transporting medications and overpacks from unit storage to a location proximate a patient, such as a nurse server or patient server. Embodiments may further include means for transporting medications and overpacks from the central pharmacy to a location proximate the patient. Such transport means as described herein may provide a substantially automated mechanism for moving medications and overpacks throughout a healthcare facility.

Figure 28:
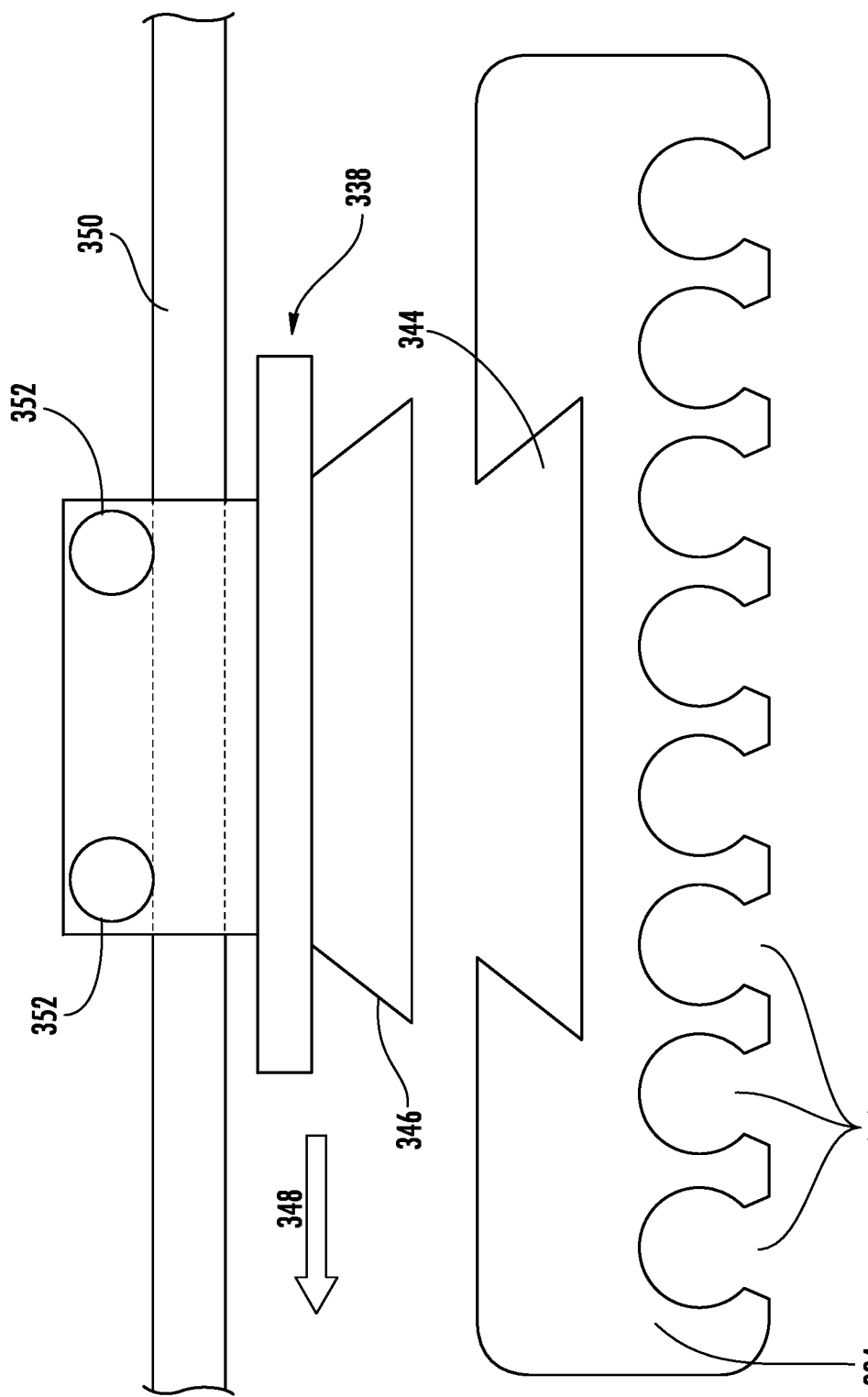
FIG. 28 illustrates an example embodiment of a carrier configured to carry overpacks and a shuttle configured to transport the carrier.

FIG. 28 illustrates an example embodiment of the carrier 334 of FIG. 25 illustrated with a plurality of receivers 342, each configured to receive a clip (not shown). In some embodiments, the clips may be integrally formed with the carrier and not be removable. In other embodiments, such as the illustrated embodiment, the clips may be removable from the receivers 342 of the carrier 334.

The illustrated embodiment of the shuttle 338 includes a trapezoidal shaped projection 346 configured to be received within the trapezoidal recess 344 of the carrier 334, similar to a dove-tail joint. In this regard, the carrier 334 may be received on the shuttle 338 by a laterally sliding movement. The carrier 334 may be locked or latched onto the shuttle 338; however, a lock or latch may be unnecessary if the rate of movement of the shuttle and the lateral movement of the shuttle is below a degree in which the carrier would slide on the shuttle. When the shuttle 338 moves along the track in the direction of arrow 348, or opposite arrow 348, the carrier is precluded from movement relative to the shuttle in the direction of arrow 348 or opposite arrow 348 by the shape of the joint formed by the projection 346 and recess 344.

The shuttle 338 may be configured to be advanced along a track 350 by a variety of mechanisms. For example, as shown in the illustrated embodiment, the shuttle 338 may include rollers 352 attached to a portion of the shuttle 338, and the rollers 352 may be configured to ride along a track 350. The shuttle 338 may be suspended from the track 350 and advanced by the rollers 352 along the track. The rollers 352 may be driven by, for example, an electric motor, which may receive power from a battery pack, or alternatively from one or more bus bars extending along the track 350. Alternatively, the shuttle 338 may be advanced along the track 350 by a cable or belt arranged proximate or inside of the track configured to pull the shuttle 338 along the track 350. In some embodiments, the shuttle may be configured to advance along the track 350 using magnetic levitation or mag-lev. As will be appreciated, a variety of mechanisms may be employed to advance the shuttle 338 along the track 350.

As shown in FIG. 25, the track along which the shuttle 338 and carrier 334 may ride may be enclosed by enclosure 340 to preclude unauthorized access to the medications during transport and to prevent external interference with moving shuttles, carriers, and the overpacks carried therewith. Example embodiments of transport devices that use tracks may enjoy advantages over conventional transport means as the tracks may be disposed proximate a ceiling, out of the way of patients, nurses, and physicians in a healthcare facility. As embodiments of the present invention may be implemented in existing facilities which were not originally designed to accommodate such transport devices, positioning the track and enclosure 340 proximate a ceiling may enable a facility to implement the transport device while not interfering with areas used by people, wheelchairs, and other portable medical equipment. While example embodiments may be implemented in existing facilities, example embodiments may also be accommodated in the designs of new structures, allowing the transport devices to travel above a ceiling or between floors of a healthcare facility.

FIGS. 25 and 28 illustrate an example embodiment of a shuttle that is loaded with a carrier; however further example embodiments of the present invention may provide for alternative transport devices that may be used to move medications from a unit storage device to a location proximate a patient. For example, pneumatic tube systems may be implemented as a transport device to advance medications as directed by a software system and/or a user interface.

In a pneumatic tube system of example embodiments, a pneumatic tube carrier may be loaded, either automatically or manually, at a unit storage device, and transported through a pneumatic tube network to the destination proximate a patient. In some embodiments, the overpack for the medication and/or supplies may be a pneumatic tube carrier, or configured to be received within a pneumatic tube carrier.

Another example embodiment of a transport device which may be used with example embodiments of the present invention may include a train system that is configured to carry overpacks to a location proximate a patient. As described above with regard to the shuttle and carrier, a track-based system may be implemented in which a vehicle is advanced along the track. The train may include a single car or multiple train car embodiment which carries overpacks to their destination.

Referring back to FIG. 23, the retrieval device 306 of the X-Y robot of the illustrated embodiment may be configured to retrieve overpacks from the unit storage and transport them to either a transport device 320 or a staging area 322. The retrieval device may also be configured to load the retrieved overpacks onto the transport device 320, or alternatively, a separate loading device may be implemented to load the retrieved overpacks onto the transport device 320. In the illustrated embodiment of FIG. 23, a car may be configured to receive the overpacks from the retrieval device 306. A single car may be configured to hold a plurality of overpacks, and additional cars may be coupled together for the transport of a greater number of overpacks.

The retrieval device 306 of FIG. 23 may also be configured to unload empty bins from the transport device 320. For example, after dispensing the contents of a reusable overpack, such as a bin, the empty bin may be returned to the unit storage 300, and the retrieval device 306 may retrieve the empty bin and move it to an area from which empty bins may be retrieved for return to the central pharmacy.

The car of example embodiments may be configured to propel itself along the track by an electric motor, for example. The car may include one or more driven wheels which contact the rail, and either by frictional engagement or by toothed engagement (such as a pinion gear of the train engaged with a rack gear of the track), the driven wheel(s) may advance the train along the track.

Figure 29:
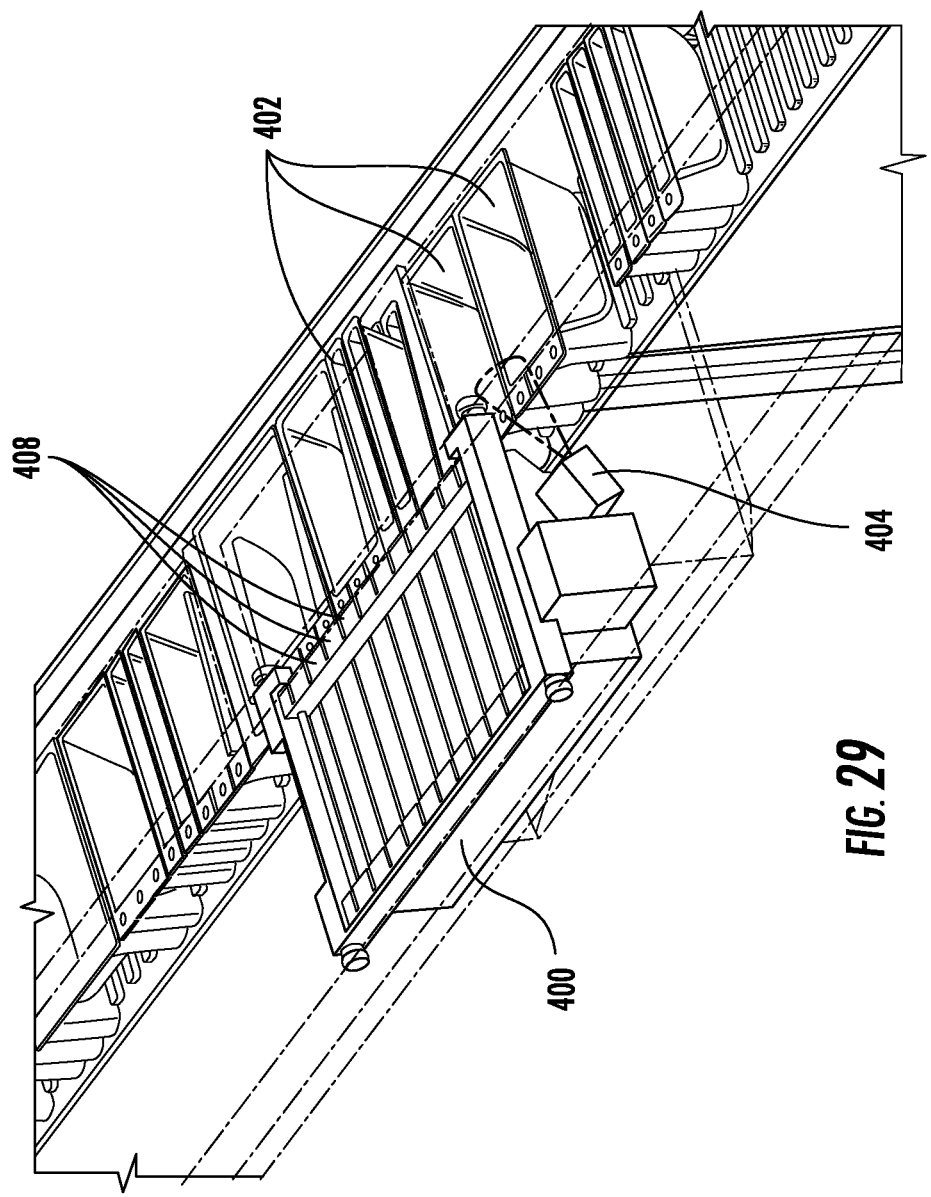
FIG. 29 illustrates a transport device and a loading device according to an example embodiment of the present invention.

FIG. 29 illustrates an example embodiment of a car 400 according to example embodiments of the present invention. In the depicted embodiment, a plurality of overpacks 402, in this case bins of a common profile but differing widths, are staged in a staging area proximate the unit storage device (e.g., staging area 322 of unit storage device 300 of FIG. 23). The car may include a plurality of loading devices 408 configured to draw the overpacks 402 onto the car. The loading devices 408 may also be configured to unload the overpacks 402 from the car by pushing them off to a staging area, nurse server, or patient server. The loading devices 408 of the illustrated embodiment may each be sized according to the width of the smallest overpack 402 such that a single loading device 408 may be used to load and/or unload one of the smallest overpacks. Larger overpacks may use more than one loading device 408 for loading and unloading. For example, an overpack that is twice the width of the smallest overpack may use two loading devices 408 for loading and unloading.

While the illustrated embodiment includes the loading devices 408 on the car 400, further example embodiments may include one or more loading devices disposed at the location where a car is to be loaded or unloaded, thereby removing the loading devices and their related structure from the mobile car 400.

The depicted embodiment of a car 400 further includes a scanner 404 configured to scan the identifying indicia on the overpacks 402. As outlined above, the identifying indicia may include a barcode, RFID tag, text, or the like. As such, the scanner may include a barcode scanner, an RFID reader, an image capture device, etc. to scan the indicia to read the identifying information contained therein. The scanner 404 may provide an indication of the contents of the overpacks to software controlling the car 400 and the loading devices 408 such that the loading devices 408 load only the overpacks 402 that are to be transported on the car 400.

While the staged overpacks 402 are described above as being disposed proximate the unit storage device, in some example embodiments, as further outlined below with regard to the nurse server and patient server, there may be staging areas proximate the patient.

In any of the above referenced track or tube based transport devices, sensors may be disposed along the length of the track to determine where a car may be located. Sensors may be disposed at specific locations proximate to the unit storage device and proximate to the car destination to facilitate accurate positioning of the car at the unit storage device and nurse server or patient server. Sensors may include optical sensors, proximity sensors, RFID sensors (which may also determine the identity of the car), or contact sensors. Additionally or alternatively, sensors may be disposed on the car and they may be configured to detect specific markings or way points disposed along the track to determine their position.

Figure 30:
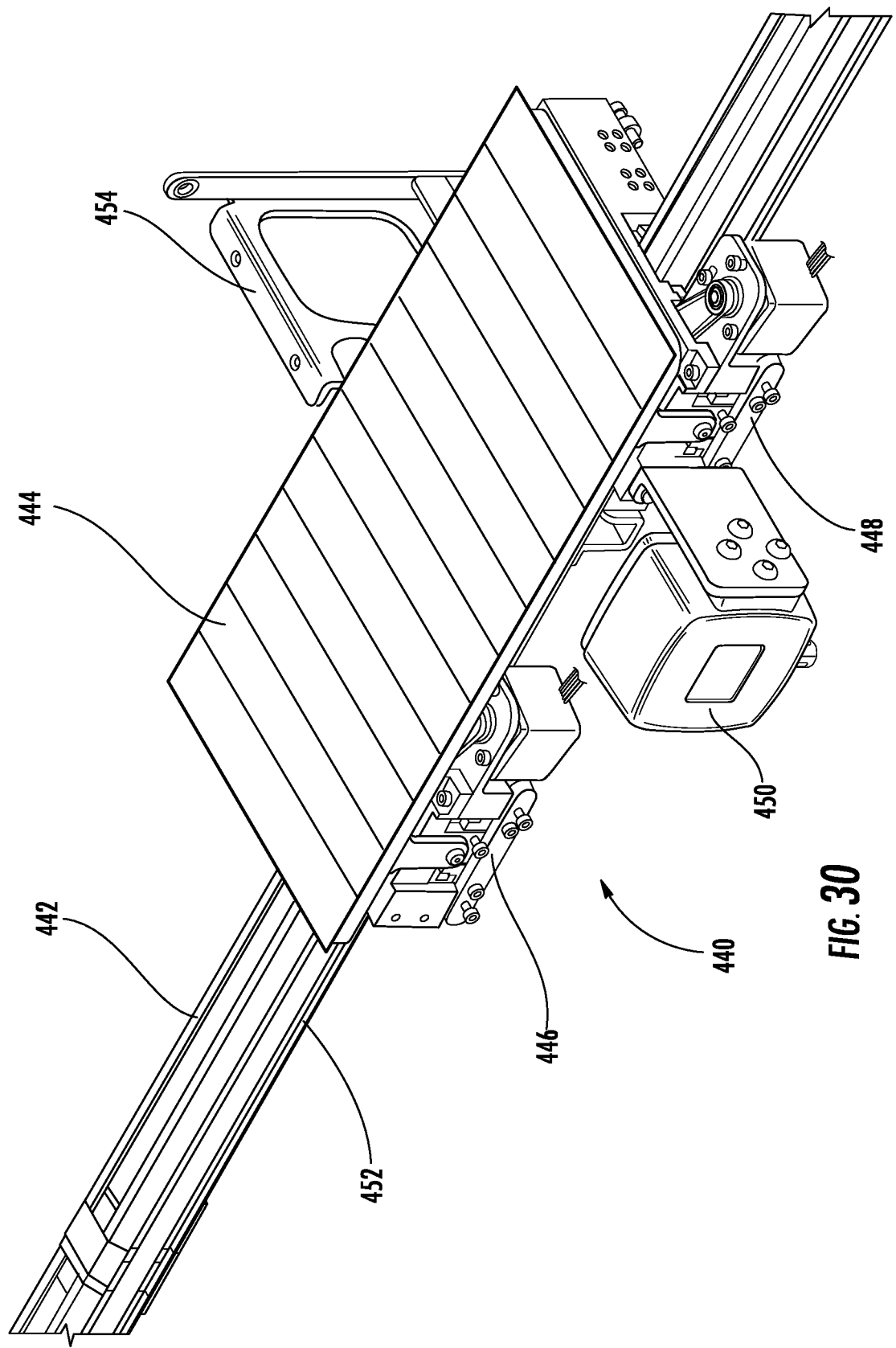
FIG. 30 depicts a track-based transport system according to an example embodiment of the present invention.

Another example embodiment of a track-based transport system is illustrated in FIG. 30 which depicts a car 440 engaged with a track 442. The illustrated car 440 includes a payload platform 444, a first bogie 446, and a second bogie 448. The car 440 further includes a reader 450 configured to obtain location information by reading a location identifying tape 452 which extends along the length of the track 442. Bracket 454 is illustrated as an example embodiment of a support which may be used to support the track 442 in an elevated, suspended position.

Figure 31:
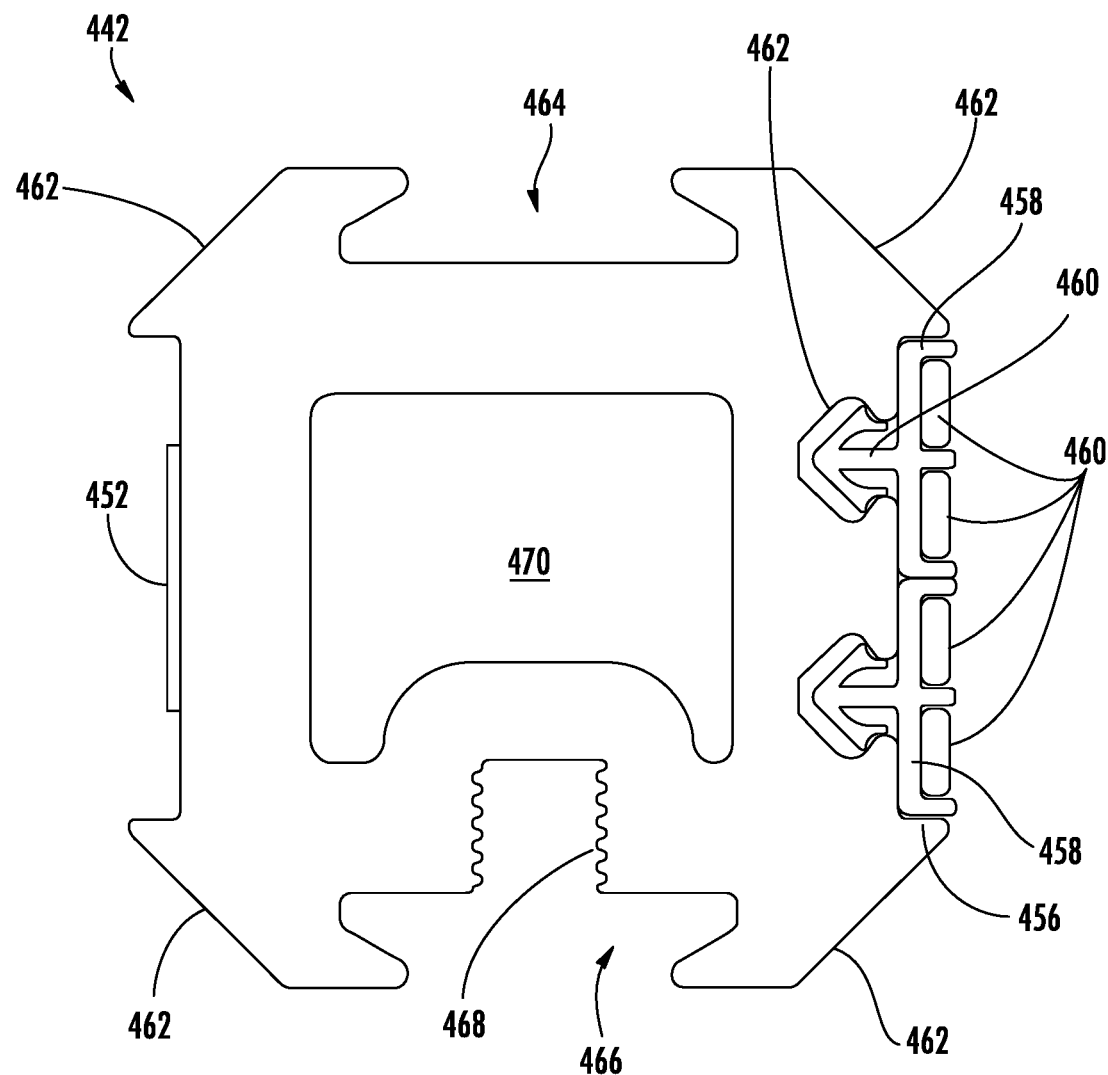
FIG. 31 illustrates a cross-section of a track used with track-based transport systems of example embodiments of the present invention.

The track 442 may be of a variety of profiles to accommodate various car and bogie designs. FIG. 31 illustrates the cross-section or profile of a track according to an example embodiment of the present invention. The illustrated embodiment includes substantially square profile with chamfered corners 462 creating surfaces, some or all of which may be engaged by rollers of the bogies as described further below.

According to some embodiments of the present invention, bus bars 460 may be disposed along the length of the track in order to conduct electricity for providing power to a drive system for a car riding along the track, to provide power for any processing capabilities which may be implemented on the car (e.g., positioning/locating, loading/unloading, reading overpack indicia, etc.). Bus bars 460 of example embodiments may also be configured to provide a communications channel to and from the car or cars riding along the track. As the bus bars 460 necessarily are electrically conductive, and as the track may be made of an electrically conductive material (e.g., extruded aluminum), the bus bars 460 may require electrical insulation from the track 442.

The track profile of the illustrated embodiment further includes a channel 456 in which one or more bus bar insulators 458 may be received. While the illustrated embodiment includes two bus bar insulators 458, embodiments may include one bus bar insulator, or more than two bus bar insulators dependent upon the number of bus bars and the number of bus bars accommodated by each bus bar insulator 458. The bus bar insulators 458 are configured to receive therein one or more bus bars 460 and are made of a material that is a poor conductor of electricity, such as a plastic. In some embodiments, the bus bars 460 may be mechanically held in place by the bus bar insulators (e.g., by frictional engagement or by snapping the bus bars into place) or the bus bars 460 may be adhered to the bus bar insulators by an adhesive or the bus bars 460 may be heated and pressed into the insulators such that the insulator material softens, conforms around the edges, and holds the bus bars in place. The bus bar insulators 458 may be held in the channel 456 by a deformable snap 461 received into a channel 462. The deformable snap may be that of a Christmas-tree fastener or other push-in clips. The deformable snap 460 may extend along the length of the bus bar insulator 458, or the deformable snap 460 may be disposed at intervals along the length of the bus bar insulators, sufficient to secure the bus bars and bus bar insulators to the track.

The profile of the track 442 of FIG. 31 further illustrates a location identifying tape 452 which is received along the length of the track 442. The location identifying tape may be continuous along the entire length of the track, or may be disposed periodically along the track. Location identifying tape according to embodiments of the present invention may include demarcations along the length of the track. Such demarcations may be read by a reader (such as reader 450 of FIG. 30) to ascertain the location of the car along the track. The demarcations may be located proximate (i.e., at short intervals) to one another to afford greater accuracy to location determination; however, embodiments of cars configured to engage the track may be configured to accurately discern distance traveled such that the demarcations may serve to re-calibrate or verify the location of a car along the track. In such an embodiment, the demarcations may be disposed along the track at greater intervals. Additionally or alternatively, while the illustrated embodiment includes a location identifying tape along the length of the track, in some example embodiments, the location identifying tape may be disposed along a wall of the enclosure in which the track-based transport device travels, or a wall of the facility along which the track extends.

Example embodiments of a track profile may further include one or more alignment slots, such as dovetail slots 464 and 466. Such alignment slots may be configured to receive alignment tabs, as detailed further below, and/or to receive locking or securing members configured to facilitate locking or securing of track sections together. Track profile embodiments may further include one or more grooved channel, such as grooved channel 468. The grooved channel 468 may include grooves that are arranged to engage a particular size and thread-pitch of fastener, such as an M6, M8, M10, M12, 1/4-20, 1/4-28, 3/8-16, 3/8-20, or any such threaded fastener. The dovetail slots 464, 466, and/or the grooved channel 468 may also be configured for use as mounting location for mounting a bracket thereto. The bracket may be used to mount the track to a wall or other surface to suspend the track as necessary for routing through a facility.

Track profiles according to example embodiments of the present invention may be configured to accommodate lateral bends (e.g., left and right turns) such that a track may follow contours of a facility. Further, track profiles may also be configured to accommodate vertical bends (e.g., up-hill, down-hill) to accommodate changes in elevation which may be necessary. The bends of the track may be accomplished in a number of manners. For example, in the case of an extruded aluminum track, the track may be mandrel bent to the degree necessary. Further, while straight track sections may be made of a first material (e.g. extruded aluminum), bends may be made of a second material which may be more flexible. For example, a bend may be made of a polymer such as high-density polyethylene (HDPE) which may not be suitable for long, straight runs between supports, but the HDPE sections may be well suited for lateral or vertical bends, where supports may be more closely spaced. Track sections made of more flexible materials, such as plastics, may include a structural member inserted there through to provide rigidity. For example, if a bend were to be made of HDPE, a rib, such as a steel rod or tube of the same radius and degree of bend may be inserted into a cavity in the track section, such as cavity 470 of FIG. 31. A flexible length of track may also be bent to the appropriate bend and injected with a material into cavity 470 which may cure to render the track section relatively rigid. Track sections made of non-conductive materials, such as plastics, may not require the bus bar insulators 458 and may have channels for the bus bars formed directly onto the track section.

Figure 32:
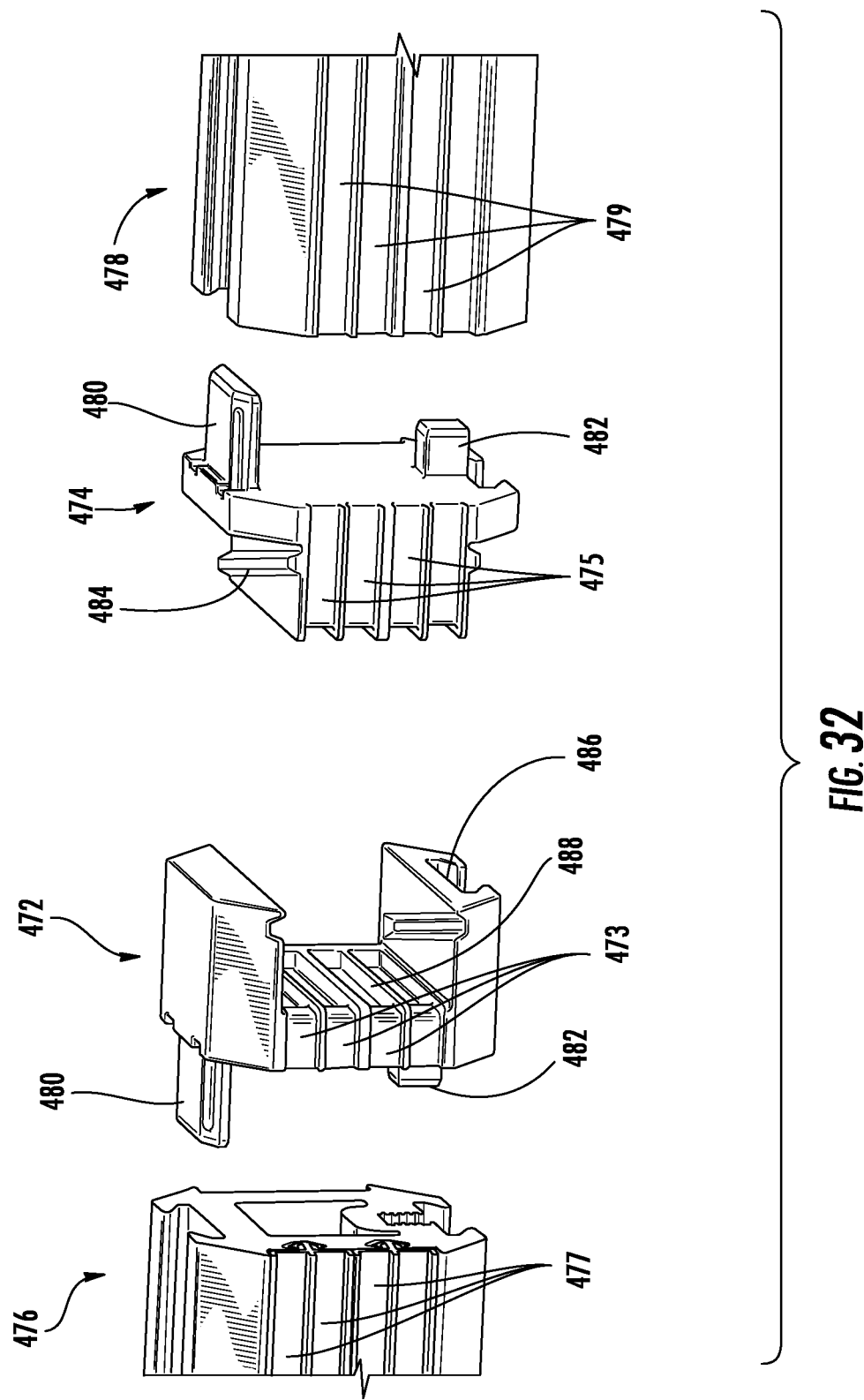
FIG. 32 illustrates a pair of end caps configured to join track sections together according to example embodiments of the present invention.

As outlined above, a track-based transport system may use a track that is formed in sections. However, the sections of the track may require secure joints there between that align the track sections and maintain electrical continuity of bus bars extending along the track. FIG. 32 illustrates an example embodiment of a pair of end caps which may be used to join together sections of track securely while maintaining alignment and electrical continuity of the bus bars. The first end cap 472 is configured to be attached to the end of a first section of track 476 and the second end cap 474 is configured to be attached to the end of a second section of track 478. The first end cap 472 is a female end cap while the second end cap 474 is a male end cap. The first section of track 476 and the second section of track 478 each include channels 477, 479 for bus bars. These channels may be disposed, for example, on bus bar insulators 458 as illustrated in FIG. 31. Each of the end caps 472, 474 also include channels 473, 475 configured to receive the bus bars. As can be seen on the first end cap 472, the channels extend parallel and aligned with the channels 477 of the first section of track 476, and continue, at an angle substantially perpendicular to the length of the track section, around a face 488 of the first end cap 472. While not visible in FIG. 32, the channels 475 of the second end cap 474 similarly extend across a face of the second end cap, substantially perpendicular to the length of the second track section 478. The end caps 472, 474 may be made of a material, such as a plastic, such that the channels 473, 475 do not require separate bus bar insulators. Further, as described in detail below, end caps made from a plastic may allow deformation of features that may engage the track sections to provide a more secure engagement.

Each of the first end cap 472 and the second end cap 474 of the illustrated embodiment include a first tab 480 and a second tab 482 configured to be received within the section of track to which they are engaged. The first tab 480 is configured as a dovetail to engage the top dovetail groove as illustrated in FIG. 31 as 464. The second tab 482 of each end cap is configured to be received in the grooved channel 468 of the track profile of FIG. 31. In order to hold the end cap to the end of the track sections, the dovetail tab 480 may include deformable elements configured to be deformed as the dovetail tab 480 is inserted into the dovetail groove 464. The second tab 482 may be configured to be wider than the narrowest portion of the grooved channel (i.e., between the peaks between the grooves) and narrower than the widest portion of the grooved channel (i.e., between the bottoms of the grooves). In this manner, the ridges between the grooves may "bite" into the second tab 482 as it is inserted into the grooved channel 468.

The protrusion of the second, male end cap 474 may be configured to be received within the recess of the first, female end cap 472. The second end cap may also include an alignment ridge 484 while the first end cap may include an alignment channel 486. As shown in FIG. 32, the first, female end cap 472 may include channels 488 disposed across the face or width of the end cap 472 for receiving therein one or more bus bars.

Figure 34:
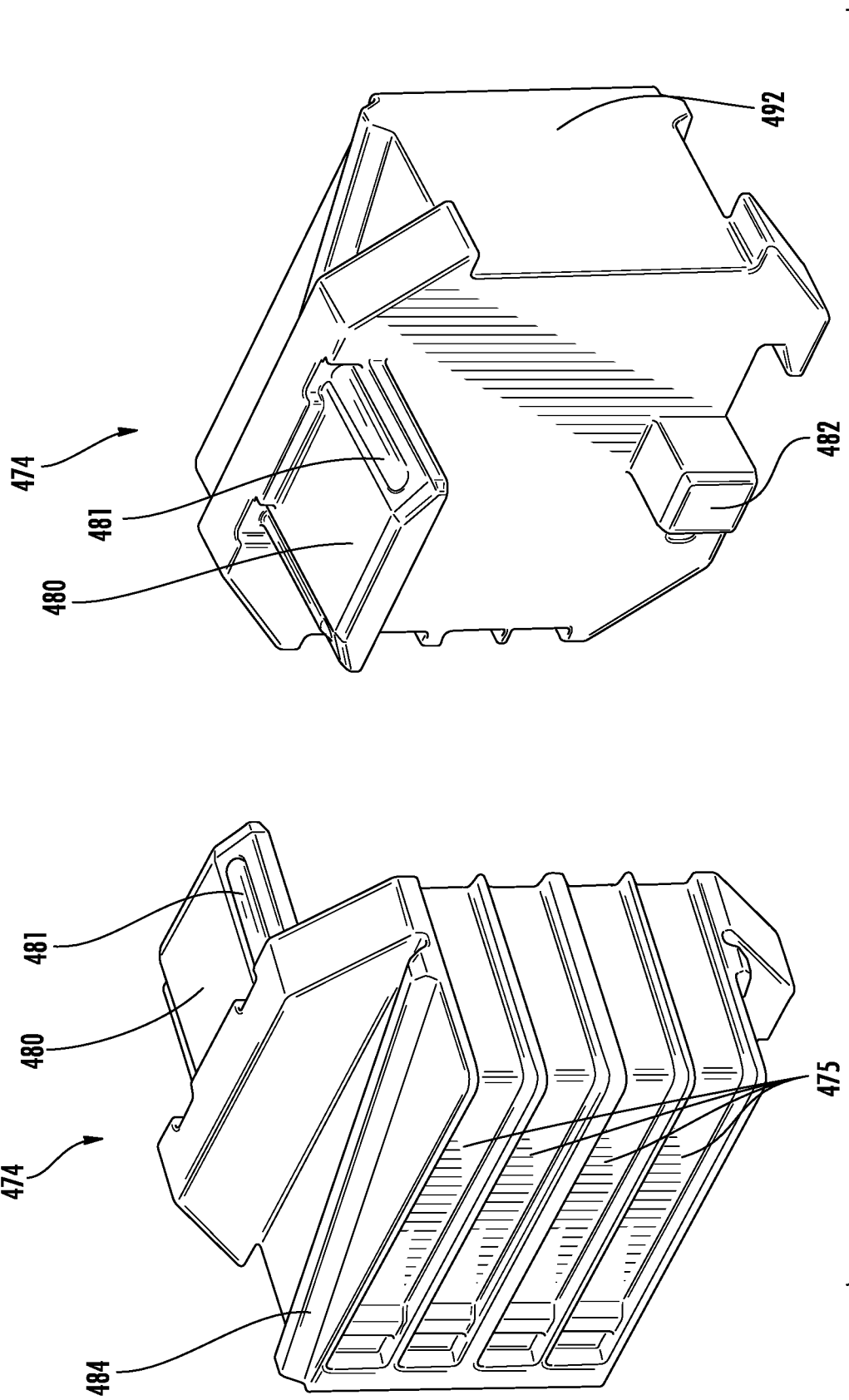
FIG. 34 illustrates an example embodiment of a male end cap used to join track sections together according to an example embodiment of the present invention.

FIG. 33 illustrates two perspective views of the female first end cap 472 including the bus bar channels 473, the first tab 480, the second tab 482, and the alignment channel 486. Also illustrated are the deformable members 481 of the first tab 480, and the recess 490 that receives the second end cap 474. FIG. 34 illustrates two perspective views of the male second end cap 474 including the bus bar channels 475, the first tab 480, the second tab 482, and the alignment ridge 484. Also illustrated are the deformable members 481 of the first tab 480, and the protrusion 492 that is received within the recess 490 of the first end cap 472. As illustrated, the first end cap includes an alignment channel at both the top and bottom of the recess 490 while the second end cap includes an alignment ridge at both the top and bottom of the protrusion 492.

Figure 37:
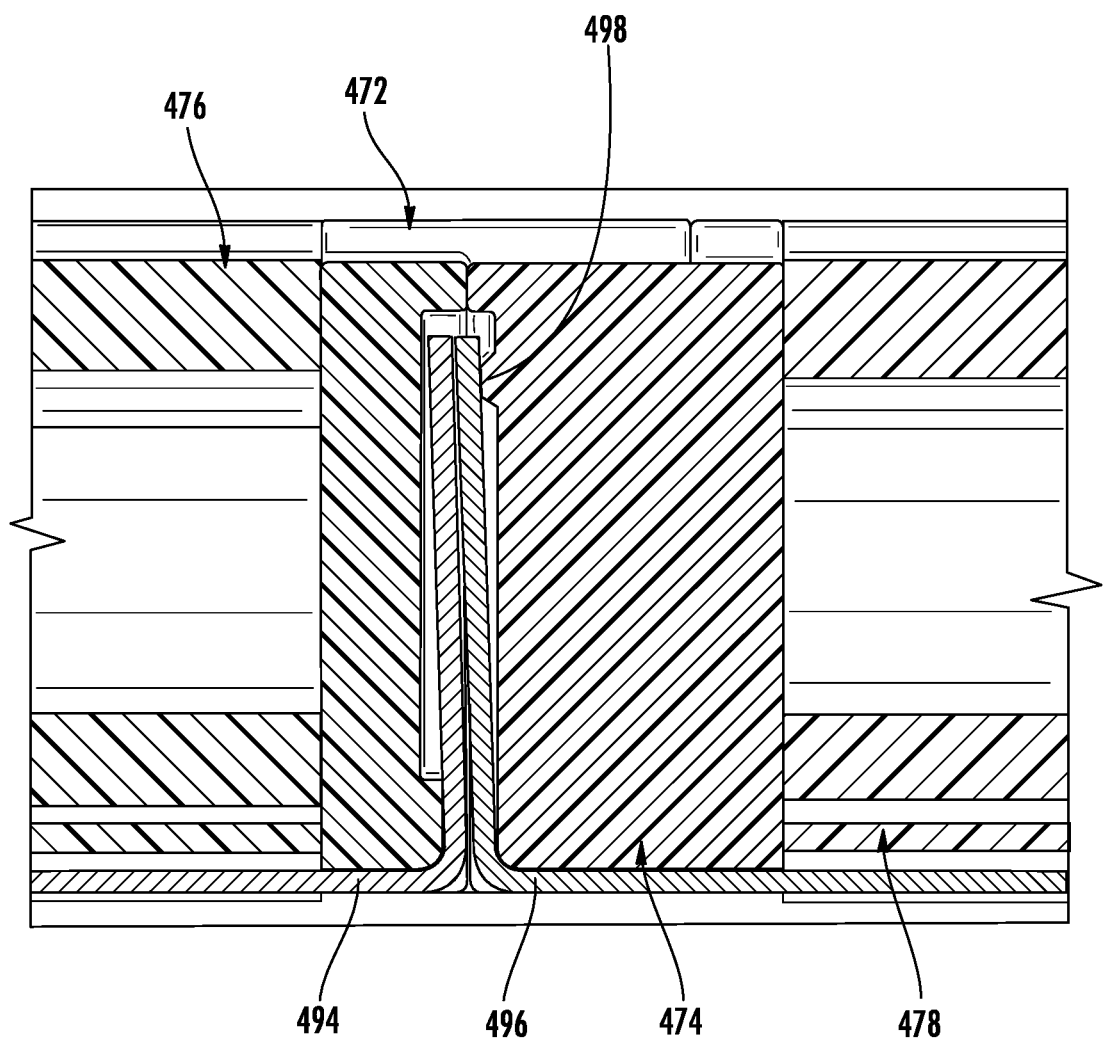
FIG. 37 illustrates a cross-section of the end caps of FIGS. 35 and 36 in an engaged position.

FIGS. 35 and 36 illustrate how the first end cap 472 and the second end cap 474 cooperate to align the first track section 476 and the second track section 478. The first end cap of FIGS. 35 and 36 is shown as transparent for illustration purposes. As shown in FIG. 35, the first track section 476 and the second track section 478 are misaligned laterally with the alignment ridge 484 of the second end cap 474 aligned with the alignment channel 486 of the first end cap. The alignment ridge 484 is received within the alignment channel 486, and as the first track section 476 and the second track section 478 are brought into alignment (aligning their lengths to be substantially collinear) as shown in FIG. 37, the protrusion 492 of the second end cap 474 is received within the recess 490 of the first end cap 472. As the first end cap 472 and the second end cap 474 align the first rack section 476 with the second track section 478, the bus bars extending across the face of the first end cap 472 (within the recess 490) are brought into engagement with the bus bars extending across the face of the second end cap 474 (around the protrusion 492). FIG. 37 illustrates a cross section of the first track section 476 and the second track section 478 joined together by the first end cap 472 and the second end cap 474, with the bus bars 494, 496, engaged along their lengths that extend across a respective end cap. Also visible in the cross-section of FIG. 37 is a biasing ridge 498 configured to bias the bus bars 496 of the second end cap 474 into engagement with the bus bars 494 of the first end cap.

Figure 38:
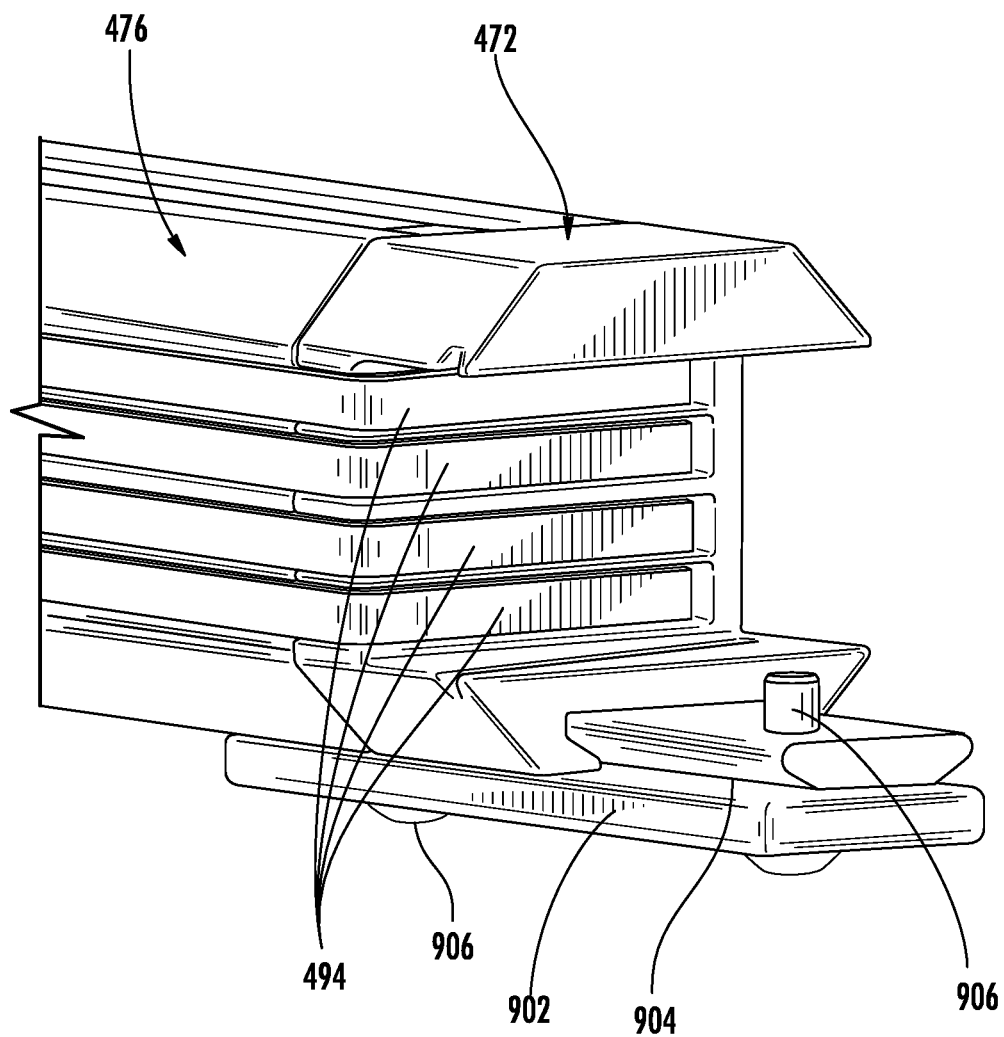
FIG. 38 depicts a female end cap including an alignment and securing feature for aligning and securing together track sections according to example embodiments of the present invention.

FIG. 38 illustrates an example embodiment of a mechanism for securing the track sections together once aligned and engaged with the first end cap 472 and the second end cap 474. The second end cap and second track section are omitted from FIG. 38 for ease of illustration. As shown, the first track section 476 includes the bus bars 494 which extend around the end cap 472, across the face of the end cap, substantially across the width of the track profile. The mechanism for securing the track sections together includes a dovetail insert 904, a plate 902, and threaded fastener 906. A second threaded fastener is shown received within the grooved channel of the first track section 476. The dovetail insert 904 is configured to be inserted into the lower dovetail groove (dovetail groove 466 of FIG. 31) of the first track section 476, prior to engagement with the second track section. The dovetail insert can be inserted before or after the first end cap 472 is engaged with the first track section. The first end cap 472 is configured with a dovetail groove that aligns with the lower dovetail groove 466 of the first track section.

When initially inserted, the dovetail insert is received fully within the first track section 476 and the first end cap 472, not extending beyond the first end cap. Alternatively, the dovetail insert 904 could be inserted into the second track section 478 and the second end cap 474. After assembling the first track section 476 with the first end cap 472 to the second track section 478 with the second end cap 474, the lower dovetail grooves of the first track section, the first end cap, the second track section, and the second end cap, are aligned. The dovetail insert 904 may then be slid within the aligned dovetail grooves to extend from the first track section to the second track section. The plate 902 may then be aligned with the dovetail insert 904 and threaded fasteners 906 may be inserted through the plate 902 and into threaded holes of dovetail insert 904. The threaded fasteners may then engage the threaded holes of the dovetail insert and be tightened. The first track section and the second track section may then be secured by the tightened threaded fasteners 906. The dovetail insert resists lateral movement between secured track sections, thereby precluding the first end cap 472 and the second end cap 474 from disengaging from one another laterally along the alignment ridge 484 and the alignment channel 486.

Figure 39:
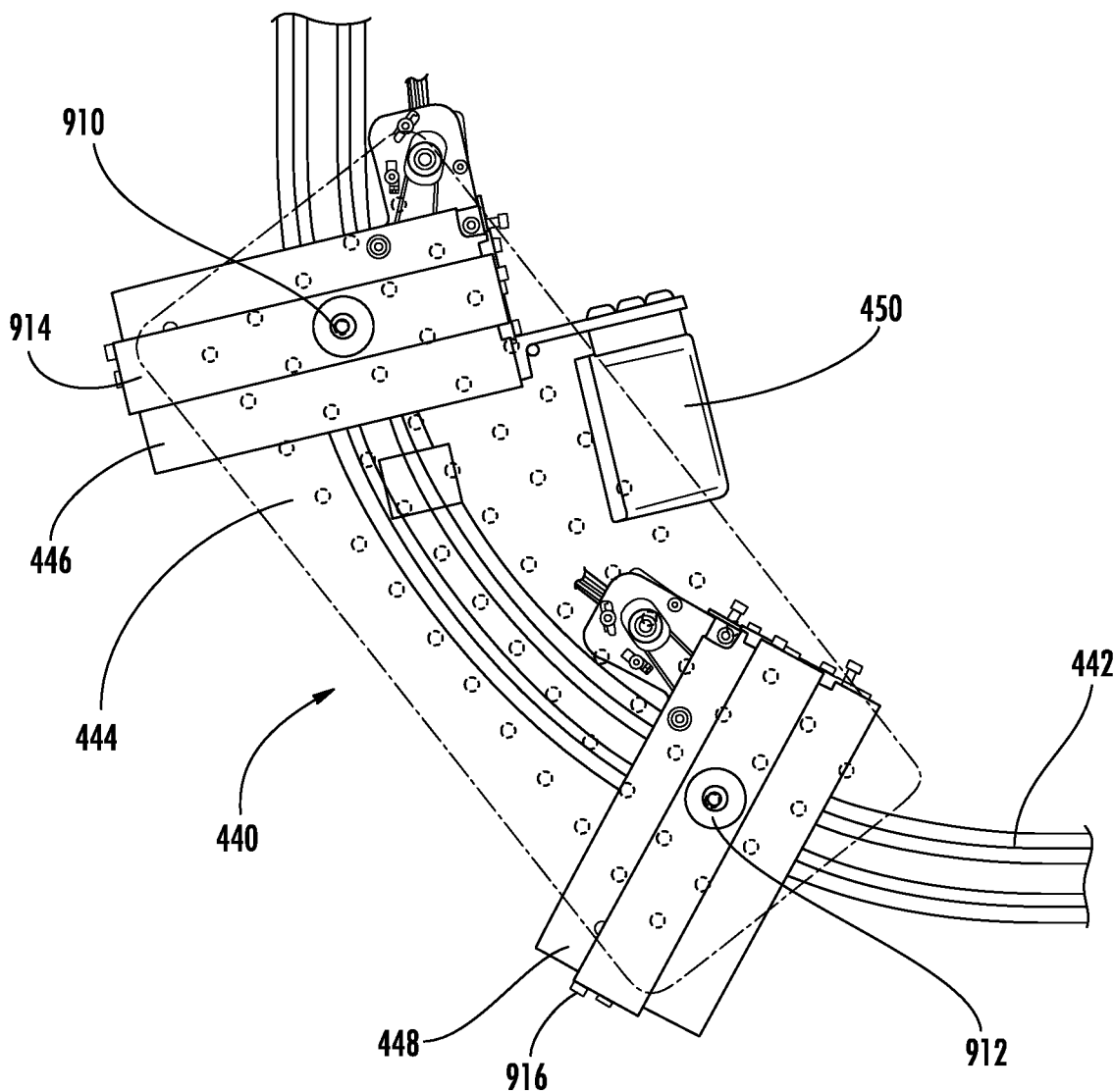
FIG. 39 illustrates an example embodiment of a car of a track-based transport system traversing a corner.

Referring back to FIG. 30, example embodiments of track-based transport systems may include a car 440 configured to advance along the track 442. FIG. 39 illustrates an example embodiment of a car 440 including a payload platform 444, a first bogie 446, and a second bogie 448. In order to turn lateral bends of a track 442 as shown, each of the first bogie 446 and the second bogie 448 may be rotatably coupled to the payload platform 444. In the illustrated embodiment, each bogie includes a tilt bracket 914, 916 that is rotatable relative to the payload platform about a rotation axis 910, 912. The axes about which the tilt brackets 914, 916 rotate are orthogonal to a plane defined by the payload platform 444. In this manner, the tilt brackets 914, 916 may turn relative to the payload platform 444 as the car 440 advances along the track 442 around a bend.

Figure 40:
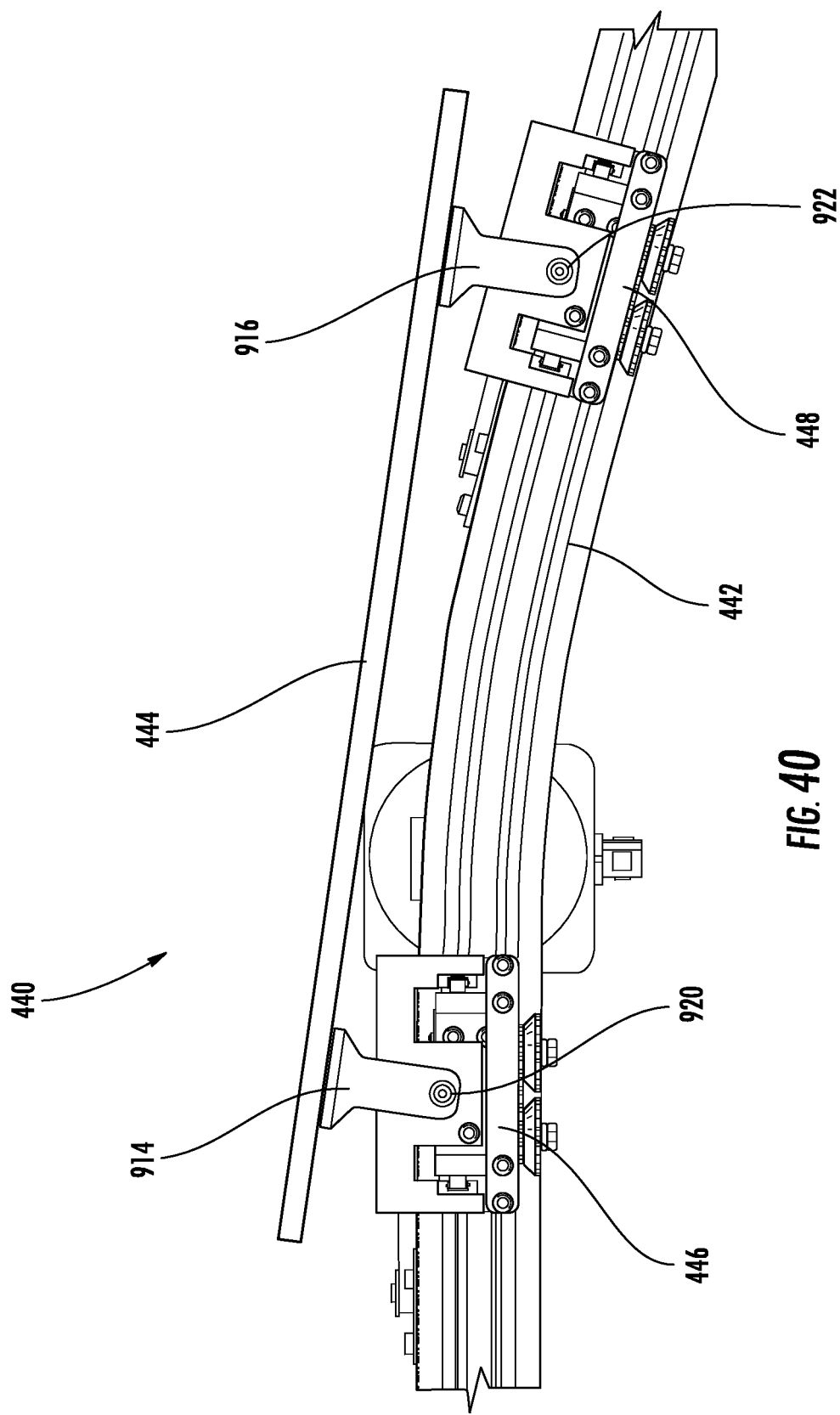
FIG. 40 illustrates an example embodiment of a car of a track-based system traversing an incline.

FIG. 40 illustrates an example embodiment of a car 440 according to the present invention configured to traverse vertical bends to transition from traveling on a flat section of track to traveling on an incline or decline. As shown, the car 440 includes a payload platform, a first bogie 446 and a second bogie 448. The first bogie is rotatably coupled to the payload platform 444 by tilt bracket 914 and the second bogie is rotatably coupled to the payload platform 444 by tilt bracket 916 as shown in FIG. 39. The first bogie 446 is pivotably connected to the first tilt bracket 914 by pin 920 which defines a first pivot axis. The second bogie is pivotably connected to the second tilt bracket 916 by pin 922 which defines a second pivot axis. The first pivot axis is perpendicular to the first rotation axis about which the first tilt bracket 914 rotates relative to the payload platform 444 (i.e., about rotation pin 910). The second pivot axis is perpendicular to the second rotation axis about which the second tilt bracket 916 rotates relative to the payload platform 444 (i.e., about rotation pin 912). The ability of the bogies 446, 448 to pivot relative to the payload platform along the pivot axes enables the car 440 to transition between flat track sections and inclines or declines.

While the example embodiment of FIG. 40 can transition to inclines and declines, the distance between the bogies, the degree to which the bogies pivot, the grip of the drive wheels on the track, the power of the drive motors, the weight of the car, and the weight of the payload each contribute to determine the degree of transition that can be traversed by the car. Each of these factors can be configured according to the track layout for a particular facility. Further, the tilt brackets 914, 916 may be adjustable relative to the payload platform 444 to adjust the distance between the tilt brackets.

Figure 41:
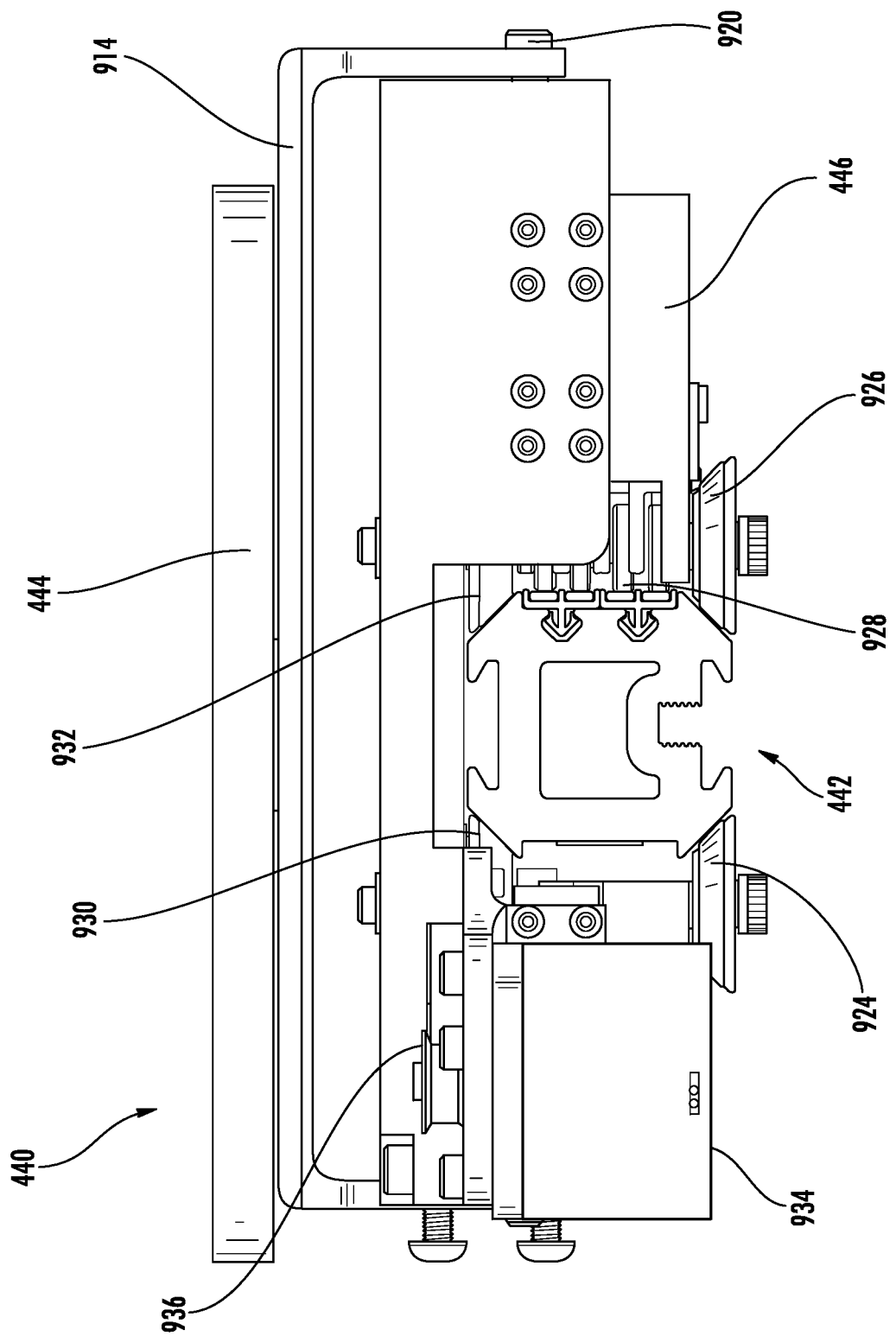
FIG. 41 illustrates the engagement of a bogie with a track profile according to an example embodiment of a track-based transport system of the present invention.

FIG. 41 illustrates a view of the car of FIGS. 39 and 40 engaged with a track section 442 as viewed through a cross-section of the track. As shown, the car 440 includes the tilt bracket 914 and bogie 446 coupled together by pin 920. A second pin may couple the bogie 446 to the tilt bracket 914 on the opposite side of the track 442; however, that pin is not visible in the illustrated view. The bogie 446 may include a first pair of rollers 924, 926 with each roller configured to engage an opposing surface of the rail, such as the lower surfaces 462 of the chamfered corners illustrated in FIG. 31. The bogie 446 may also include a second pair of rollers 930, 932 with each roller configured to engage an opposing surface of the rail, such as the upper surfaces 462 of the chamfered corners of FIG. 31. As shown, each of the rollers is separated from an adjacent roller, at least in part, by the track. The axis of rotation of each of the rollers is configured to be substantially orthogonal to the plane defined by the payload platform 444 when the car 440 is on a flat track surface. Each of the rollers includes a roller surface that is disposed at an angle relative to the axis of rotation of the roller, where the angle is between about thirty degrees and about sixty degrees.

According to some embodiments, one or more of the rollers may be configured to be a driven roller. In the illustrated embodiment, one roller 930 of the bogie 446 is configured to be driven. The driven roller 930 of the illustrated embodiment is driven by an electric motor 934 with a belt drive 936 arranged between the motor 934 and the driven roller 930. In the illustrated embodiment, the motor has an axis of rotation that is parallel to that of the driven roller 930 and the other, idler rollers 924, 926, and 932. While some example embodiments of a car 440 may include a power source such as a battery to drive the motor, the illustrated embodiment taps electrical current from the bus bars of the track. FIG. 41 depicts a series of rollers 928 configured to be electrically coupled to the bus bars. Each bus bar is contacted by one or more conductive rollers, and the conductive rollers are engaged by a brush or contact to create an electrical connection between the bus bars and the car 440. The car may use one or more of the bus bars to provide current to the electric motor 934 and drive the car 440 along the track 442.

Figure 42:
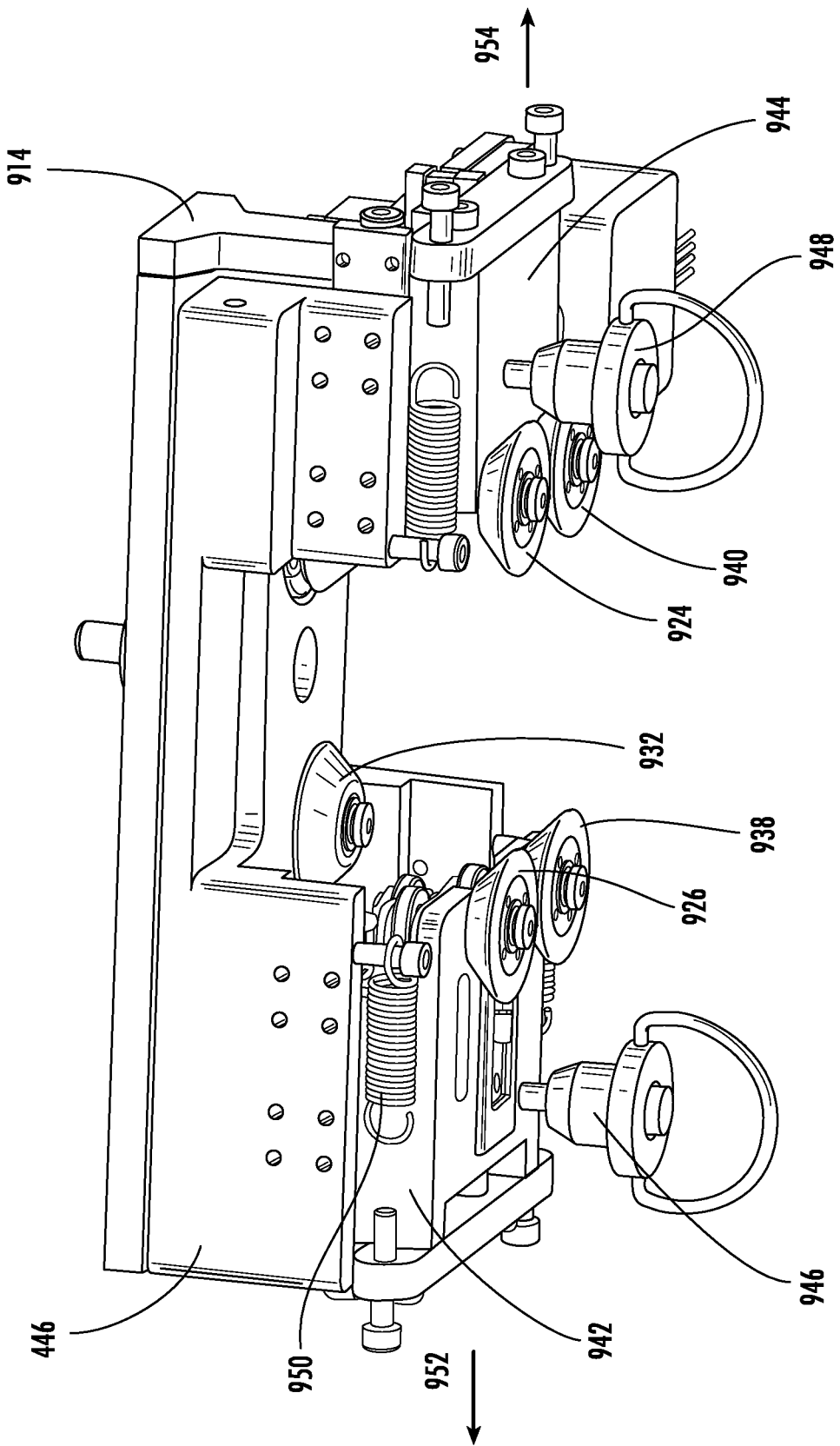
FIG. 42 depicts a bogie configured to be removed or loaded onto a track of a track-based transport system of example embodiments of the present invention.

FIG. 42 illustrates the bogie 446 of FIG. 41 as viewed from the opposite side, with the track removed. As shown, the bogie 446 includes roller 924, 926, 930, and 932. The bogie may also include another pair of rollers 938, 940, which may provide additional stability to the bogie relative to the track. Each of rollers 938 and 940 may also engage the lower surfaces 462 of the track. The rollers configured to engage the lower surfaces 462 of the track may ride on carriages 942, 944 configured to move laterally away from the track, along arrows 952, 954. Moving the rollers 924, 926, 938, and 940 away from the track enable the bogie 446, and thus the car to be lifted off of the track. In the illustrated embodiment, the carriages 942 and 944 may include biasing elements, such as springs 950 configured to bias the carriages 942 and 944 toward the track, and thus drive the rollers 924, 926, 938, and 940 into engagement with the lower surfaces 462 of the track, in an engaged position. Lock pins 946 and 948 may be used to retain the carriages 942, 944 and the associated rollers in a loading position, wherein the bogie may be free to be loaded and unloaded from the track.

While the aforementioned transport devices include track-based transport systems, further transport devices may also be used to transport overpacks to locations proximate a patient. For example, another embodiment of a transport device may include a continuous conveyor mechanism to which carriers or train cars are coupled when they are ready for transport, and the carriers or train cars may be decoupled from the conveyor mechanism when they reach their destination along the path of the continuous conveyor. A conveyor may be configured to continuously move along a transport path of a unit of a healthcare facility (e.g., in an overhead transport enclosure) and overpacks may be arranged to be loaded and unloaded from the conveyor by a loading device. For example, an overpack that is to be transported from a unit storage facility to a location proximate a patient may be pushed onto a moving conveyor. The conveyor may advance along its path toward the location proximate the patient. A scanner at the location proximate the patient may scan the identifying indicia of the overpack and recognize the overpack as being destined for the location proximate the patient. A loading device at the location proximate the patient may unload the overpack from the conveyor, either to a staging area proximate the patient or to a patient or nurse server. Similarly, the loading device at the location proximate the patient may load an empty overpack to the conveyor for return to the unit storage device or to a location specifically configured for the return of empty or unneeded overpacks.

While above example embodiments of transport devices may can be implemented in existing facilities by mounting a track and enclosure 340 proximate a ceiling, other transport devices may not require a track or enclosure to transport medication to a location proximate a patient. For example, an automated guided vehicle may transport medications and supplies from a unit storage device to a location proximate a patient while traveling along hallways shared with patients, nurses, and physicians. An automated guided vehicle, or AGV, may arrive at a unit storage device and may be loaded either manually or automatically with medications and supplies. The AGV may then transport the medications and supplies to the location proximate the patient, by guiding themselves along the hallways of the healthcare facility. The AGVs may be configured to advance along conductive tracks embedded into the floors, or the AGVs may be programmed with facility layouts to guide themselves through hallways. In either embodiment, the AGVs may be capable of detecting obstacles and people to slow down or stop to avoid contacting an obstacle or person. The detection capabilities may be in the form of proximity sensors, optical sensors, contact sensors, etc. The AGVs of example embodiments may be powered by batteries which may be rechargeable.

The aforementioned transport devices may be configured to transport medication and supplies from a unit storage device to a location closer to a patient, which may be in the form of a staging area proximate a patient, a nurse server, or a patient server, embodiments of which are described herein below. While the aforementioned transport devices may be described with respect to transporting medication from the unit storage device to a location closer to a patient, embodiments may include transport devices configured to transport medications directly from the central pharmacy to a location proximate a patient. Such an embodiment may be implemented where the central pharmacy includes various features described above with respect to the unit storage device. For example, a central pharmacy may include a pneumatic tube system or track-based transport system which may be loaded and sent directly to a location proximate the patient.

Proximate Storage

Embodiments of the present invention as described above may be configured to transport medication and supplies from a unit storage device, via a transport device, to a location proximate a patient. Embodiments of the present invention may provide means for staging and or storing medication at a location proximate a patient. The location proximate to a patient may include a location that is disposed between the unit storage device and the patient bed. Example embodiments of the location proximate the patient may be referred to herein as proximate storage, including a staging area proximate the patient, a nurse server, and a patient server.

Proximate storage embodiments including a staging area may be used in conjunction with a nurse server or patient server. The staging area may be configured to receive medication and supplies, such as in the overpacks described above, and temporarily store the overpacks while awaiting dispensing to authorized medical personnel. As illustrated in FIG. 29, the staging area may be arranged adjacent to the track of a track-based transport device such that the transport device may transport the overpacks from the unit storage device to the staging area proximate the patient and leave the overpacks at the staging area while the transport device delivers additional overpacks to additional staging areas. The staging area used for proximate storage may allow a transport device to continue to transport overpacks, thereby improving the efficiency with which the transport device is operating. Further, staging proximate a nurse server or patient server may reduce delivery time of medications.

As outlined above, the track-based transport device may be configured to travel along a track that is enclosed (e.g., enclosure 340 of FIG. 25) proximate a ceiling of a unit of a healthcare facility. The track may also be disposed in an area above the ceiling, or below the floor of a unit of a healthcare facility. As such, a staging area may similarly be disposed in an enclosure proximate a ceiling, in an area above a ceiling, or in an area below the floor in dependence upon the location of the track-based transport device. The staging areas may be arranged at locations proximate to patients and proximate to a nurse server or patient server.

Figure 43:
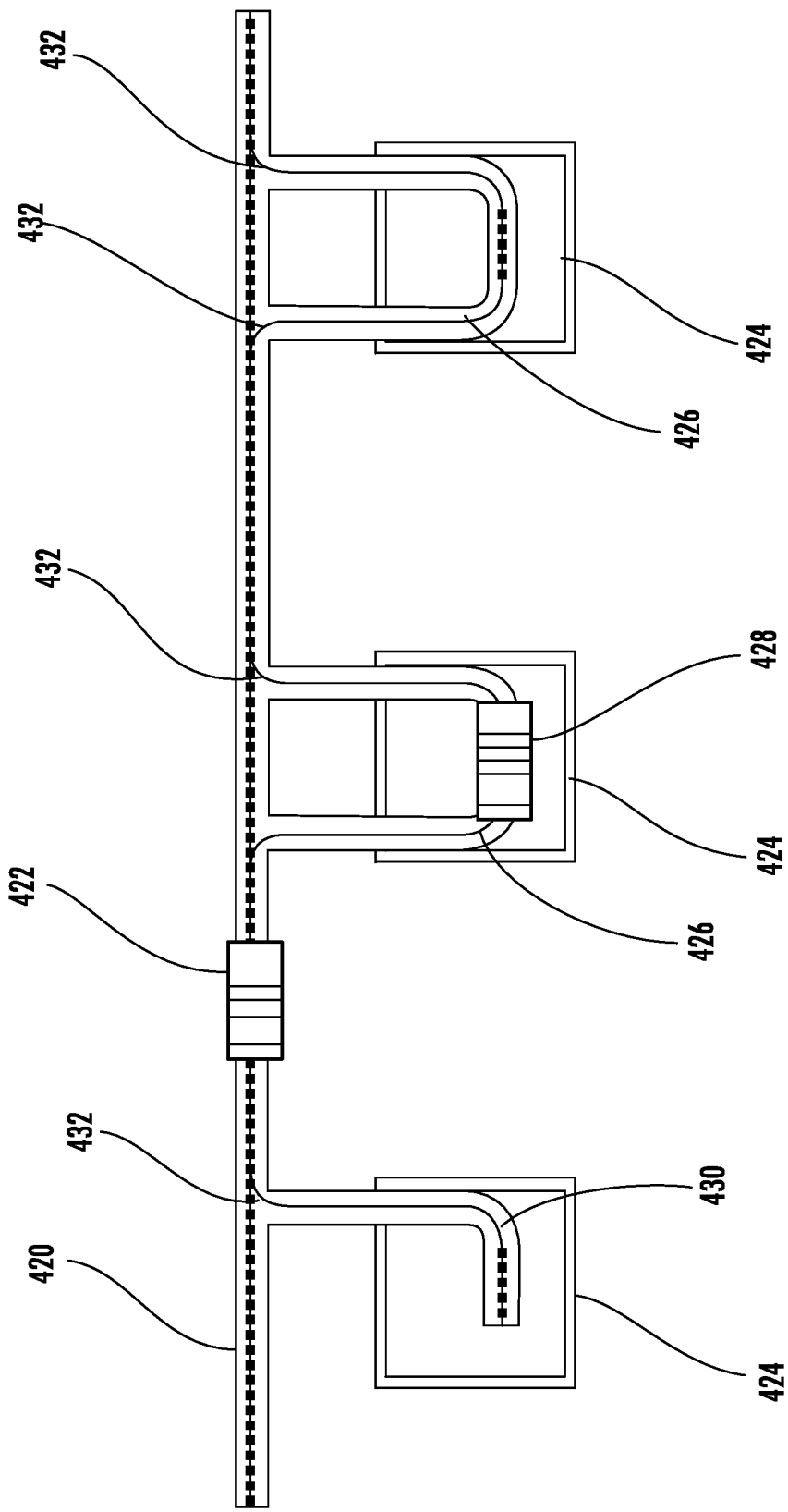
FIG. 43 illustrates a track system for a transport device according to an example embodiment of the present invention.

An example embodiment described above with respect to FIG. 29 included loading and unloading overpacks from a train car 400, some embodiments of track-based transport devices may use the transport device for storing or staging the overpacks proximate to the patient. FIG. 43 illustrates an example embodiment of a track-based transport system which includes a main track 420 and loops 426 extending from the main track. In the illustrated embodiment, each of the track loops 426 extend proximate a patient server or nurse server 424. A transport device, such as a train car 422, may be advanced from a unit storage device bound for a patient server 424. Upon arrival at the track loop 426 proximate the appropriate patient server, the train car may be diverted to the track loop of that patient server. The train car may be diverted by a conventional switch 432 used in track-based or rail-based transport devices. The diversion of the train car may be controlled, for example, by logistics software that tracks and directs transport devices to their appropriate locations. Additionally or alternatively, the car may be programmed to be autonomous with destination information. In such an embodiment, the car may be configured to control track switches as needed, or to select a track path without the use of switches.

FIG. 43 illustrates a train car 428 staged at a patient sever 424 ready to dispense the contents of the overpacks on the train car 428 to the patient server. Since the track loop 426 is arranged off of the main track 420, train car 422 may travel along the main track 420 uninterrupted to its destination. While the illustrated embodiment depicts track loops 426, embodiments may also include track spurs 430. The track spurs 430 may require fewer switches 432; however, the track spurs 430 also require the train cars to be reversed to enter back onto the main track 420. Track loops 426 also may offer additional staging space for multiple train cars 428.

Nurse Servers and Patient Servers

While staging of overpacks may be performed track-side or along the track with a track-based transport device, staging may also be performed at or in nurse servers or patient servers. A nurse server is a device configured to be accessed by a nurse (or other authorized medical personnel) for the retrieval of medication and supplies for a plurality of patients served by that nurse. A patient server is a device configured to be accessed by a nurse (or other authorized medical personnel) for the retrieval of medication and supplies for a single patient.

While the term nurse server implies access by a nurse, any authorized medical person may access the nurse server. For example, a doctor, a laboratory technician, anesthesiologist, a phlebologist, or a phlebotomist may be considered an authorized medical person which may be authorized to access one or more nurse servers as will be described further below.

The number of patients served by a nurse server may vary, and may be all of the patients for whom a nurse has responsibility or for a subset of the patients for whom a nurse has responsibility. As the nurse server is configured to provide medication and supplies for a plurality of patients, the nurse server may be located in an area close to the patients served by the nurse server. This location may be closer to the patients served than the unit storage device outlined above.

On the other hand, a patient server may be configured to serve only a single patient. The patient server may be accessed by authorized medical personnel as outlined above and described further below. As the patient server serves only a single patient, the patient server may be located close to that patient. A patient server may be located in the patient's room or nearby for convenient access by the authorized medical personnel. Generally, a patient server is not intended to be accessed by a patient, but rather by the medical personnel caring for the patient.

While example embodiments of patient servers and nurse servers differ in the number of patients they are configured to serve, their function may be substantially similar. However, some features may be better suited to one or the other as will be appreciated by one of skill in the art.

As outlined above medication and supplies may be received at a nurse server or patient server and staged to await dispensing to authorized medical personnel. Medication and supplies may also be received in response to a request such that they are dispensed upon arrival rather than staged. In still other embodiments, medication and supplies may be delivered to the nurse server or patient server for just-in-time (JIT) dispensing to authorized medical personnel.

Medications and supplies may be dispensed from the nurse server or patient server in a variety of manners. In one example embodiment, when the medication needed by a patient arrives at the nurse server, a message may be sent to the appropriate authorized medical person that is responsible for retrieving and administering the medication to the patient. In such an embodiment, an overpack may arrive at the nurse server or at a staging area proximate the nurse server, and upon scanning of the identifying indicia, an alert or message may be sent, for example via a wireless network or near-field communication protocol, to a device carried by the authorized medical person. The device may include a pager, a phone, a tablet computer, or any other portable device able to receive and present the alert or message.

Figure 44:
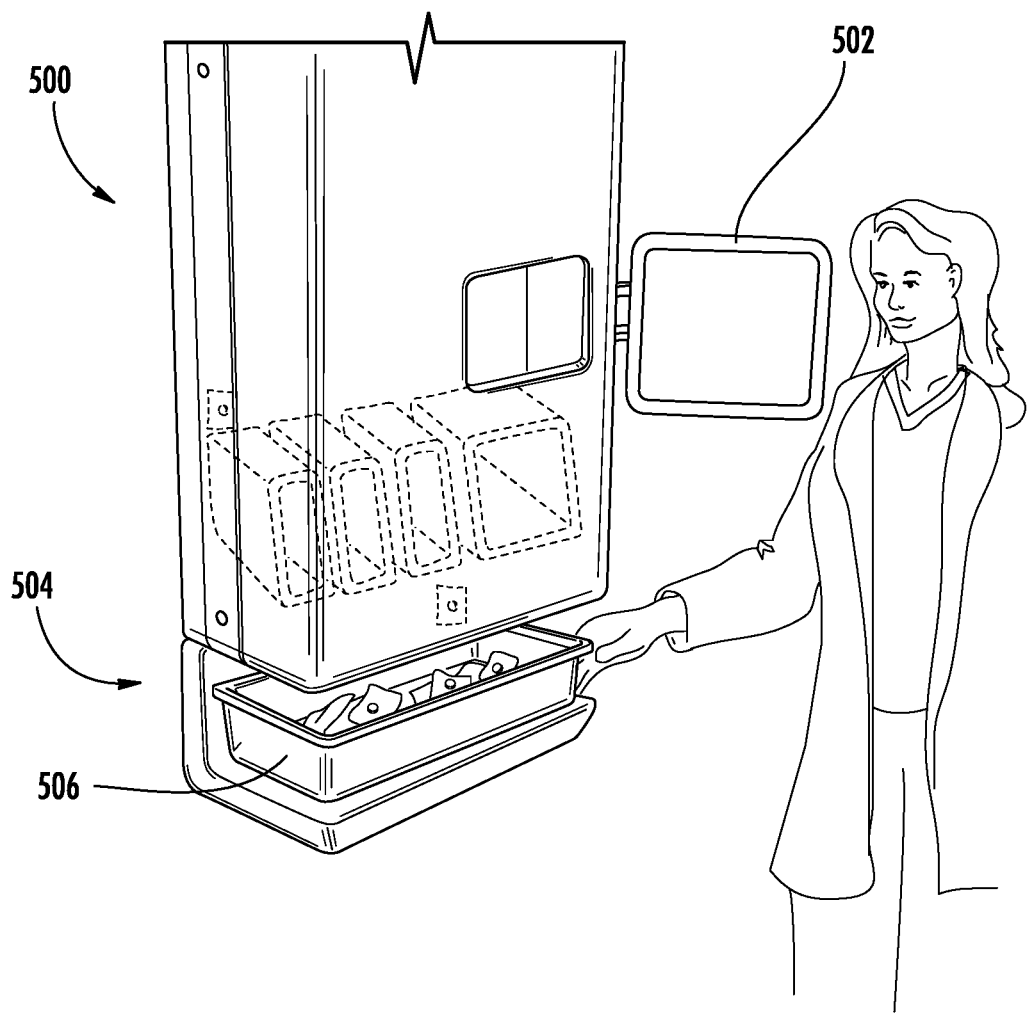
FIG. 44 illustrates a nurse server according to an example embodiment of the present invention.

In another example embodiment, described with respect to the nurse server 500 illustrated in FIG. 44, an authorized healthcare person may arrive at the nurse server, and using a user interface 502, which may include a touch screen, keypad, display, etc., request medications and supplies for a particular patient. The authorized medical personnel may first be required to provide identification of themselves to confirm that they are an authorized medical person, then the authorized person may enter a patient's identification. After receiving the patient's identification, the medication and related supplies may be dispensed, for example, to dispensing area 504. In an embodiment in which the server 500 is a patient server, the authorized medical person may only need to identify themselves and ok the dispensing of medication, as the patient server would not require the identification of the patient since it is configured to only dispense for a single patient.

In some example embodiments, the dispensing area 504 may include a bin 506 which may then be taken by the authorized medical person to the patient for administering the medication. The bin 506 may then be returned to the nurse server 500. The medication and supplies may be dispensed to the dispensing area 504 from a staging area above the nurse server 500 or they may be dispensed directly from a transport device above the nurse server. The medications and supplies may be gravity fed from the staging area or the transport device to the dispensing area.

Figure 45:
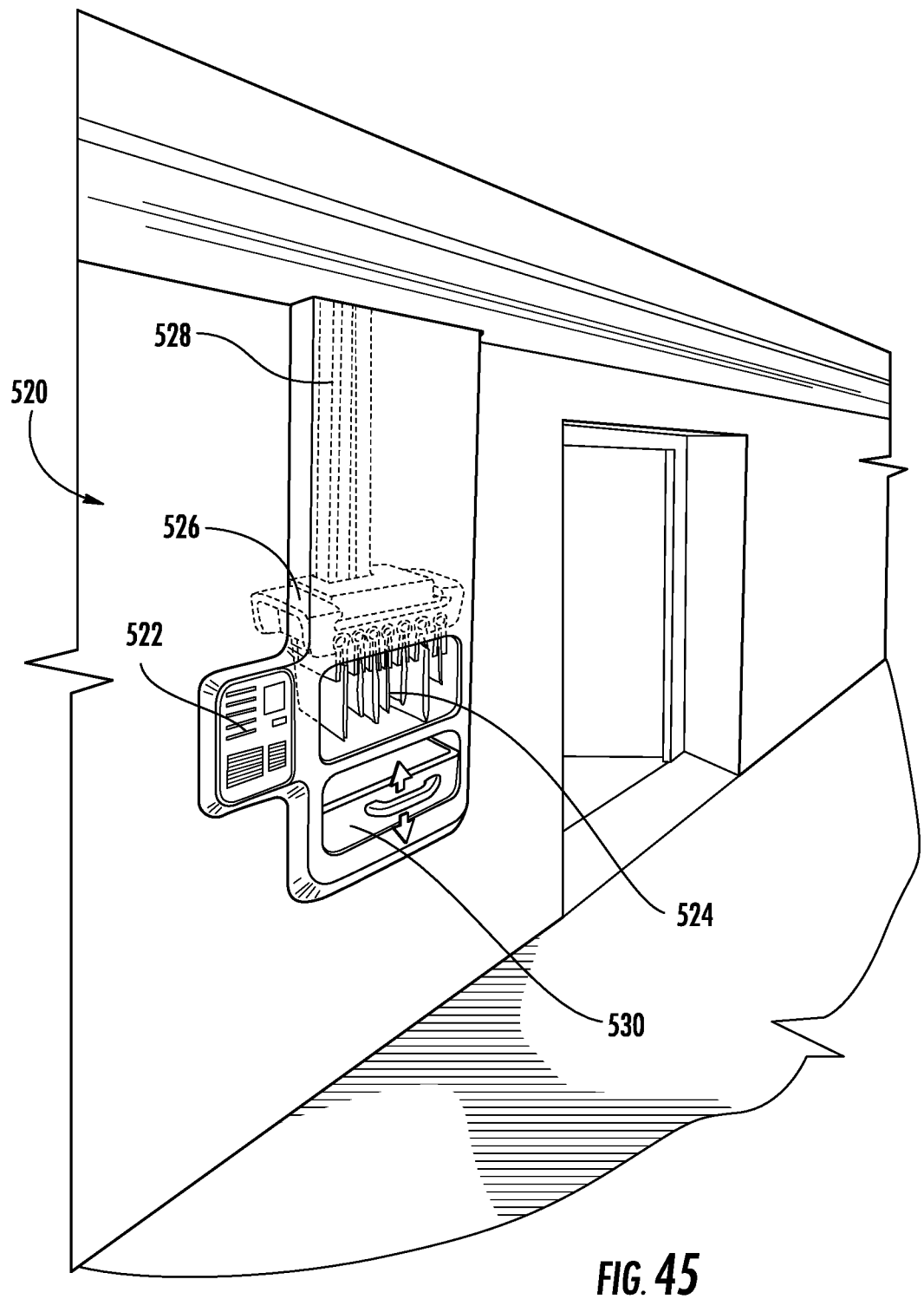
FIG. 45 illustrates a nurse server according to another example embodiment of the present invention.

FIG. 45 illustrates another example embodiment of a nurse station 520 which includes a user interface 522 and a medication dispensing drawer 530. In the illustrated embodiment, a track based transport device, such as the illustrated carrier 526, may arrive at the nurse server 520 or be staged above the nurse server awaiting dispensing. In response to a request, or ahead of an anticipated request, the carrier 526 may be advanced down thru the nurse server to a dispensing area 524, which includes a viewing window in the illustrated embodiment. After authorization of the authorized medical person, the medication and supplies overpacks may be dispensed to the dispensing drawer 530. The authorized medical person may then remove the medications and supplies for administering to a patient. The embodiment of FIG. 45 may also be implemented as a patient server configured to dispense medication only for a single patient.

Figure 46:
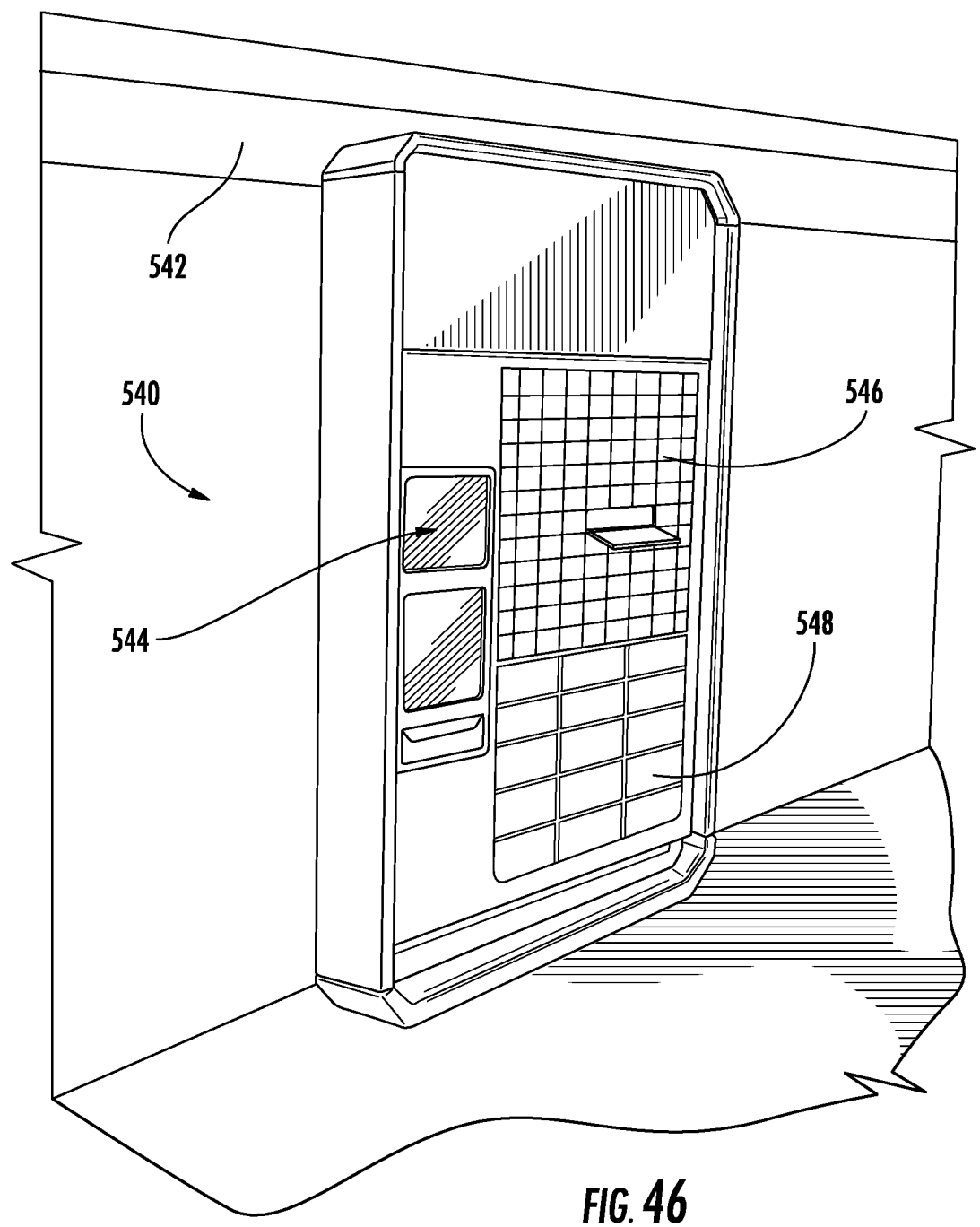
FIG. 46 illustrates a nurse server according to yet another example embodiment of the present invention.

FIG. 46 illustrates another example embodiment of a nurse server 540 according to an example embodiment of the present invention. The illustrated embodiment depicts an enclosure 542 proximate the ceiling of the healthcare facility unit. The enclosure 542 may enclose a track for a track-based transport device to transport overpacks of medications and supplies to the nurse server 540 ahead of or in response to requests for medication or supplies. The illustrated embodiment may be well suited for the overpacks of FIG. 5. Upon receipt of the overpack boxes, an X-Y robot within the nurse server, similar to the X-Y robot described with regard to the unit storage device above, may place the overpack boxes on shelves within the nurse server 540. The nurse server may include a user interface 544 and a plurality of doors 546, and larger doors 548, each configured to be individually openable.

Figure 47:
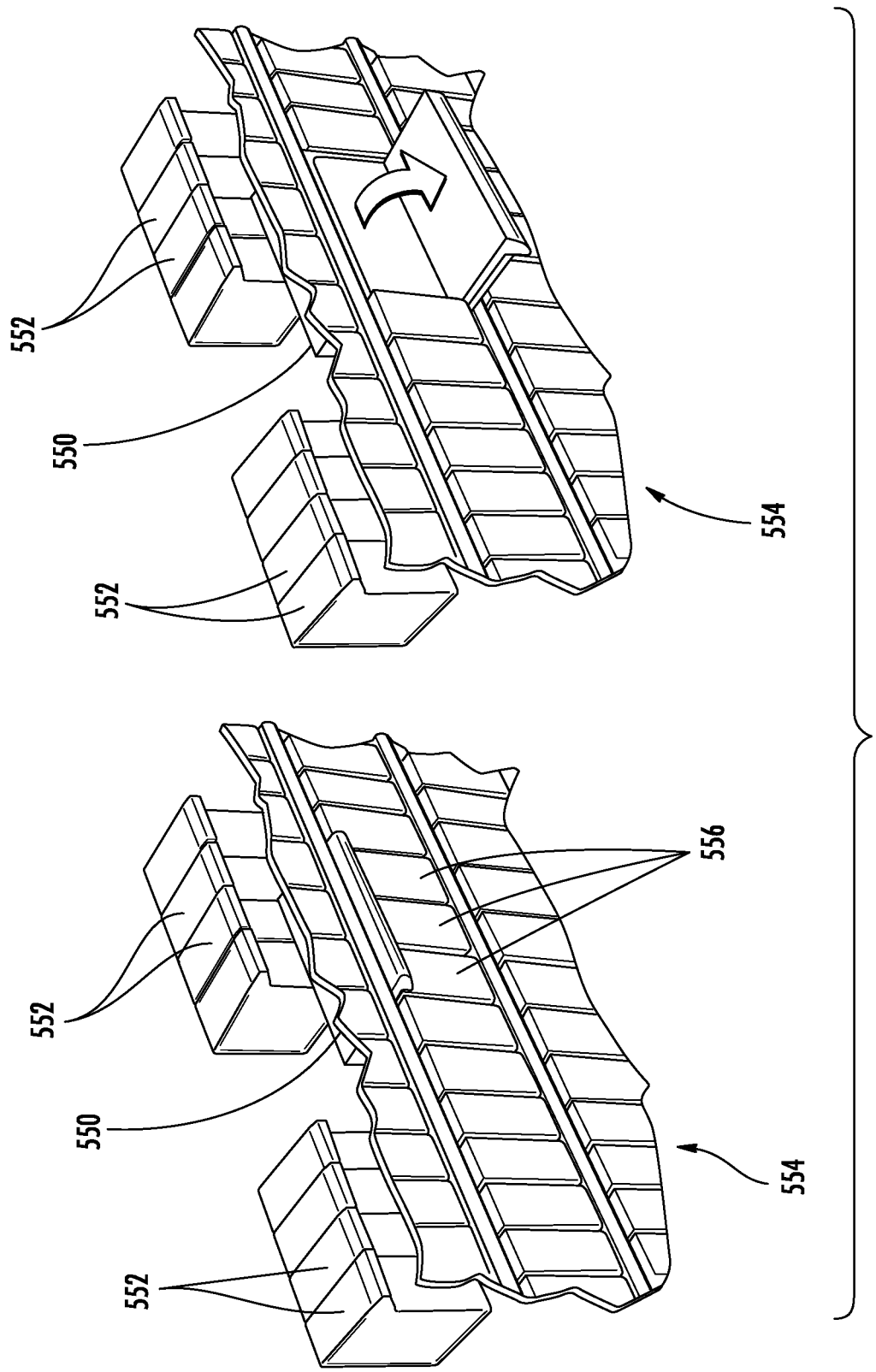
FIG. 47 depicts the overpacks and access provided thereto within the nurse server of the embodiment of FIG. 46.

In response to the authorization of an authorized medical person, and a request for medication for a particular patient, the doors arranged in front of the overpack(s) containing the medication requested may be unlocked allowing the person to open the doors, or the doors may be configured to open automatically. The authorized medical person may then access the contents of the overpack. FIG. 47 illustrates an example embodiment of how a nurse server according to FIG. 46 may operate. In the illustrated embodiment, an overpack containing the requested medication is advanced from the plurality of overpacks available 552 to the plurality of doors 554. In response to the overpack 550 being placed at a subset of the plurality of doors (namely doors 556), the doors become unlocked or unlatched. The doors may then be opened as illustrated to access the contents of the overpack 550. Doors that are not arranged in front of the selected overpack 550 may remain locked, precluding access to the plurality of overpacks 552 other than the selected overpack 550. The selected overpack 550 may be advanced, for example, by the X-Y robot or by actuators disposed in the nurse server arranged to present selected overpacks to an authorized person.

Referring back to FIG. 46, the nurse server 540 may include larger doors 548 arranged to provide access to larger overpacks, or alternatively, the large doors 548 may provide access to manually loaded bins containing medications and supplies not provided to the nurse server by the automated transport device. Medications such as as-needed medications or supplies that may be used on an as-needed basis may not be predicted by a system of example embodiments such that a supply of as-needed supplies and medications may be maintained at a nurse server or patient server.

Figure 48:
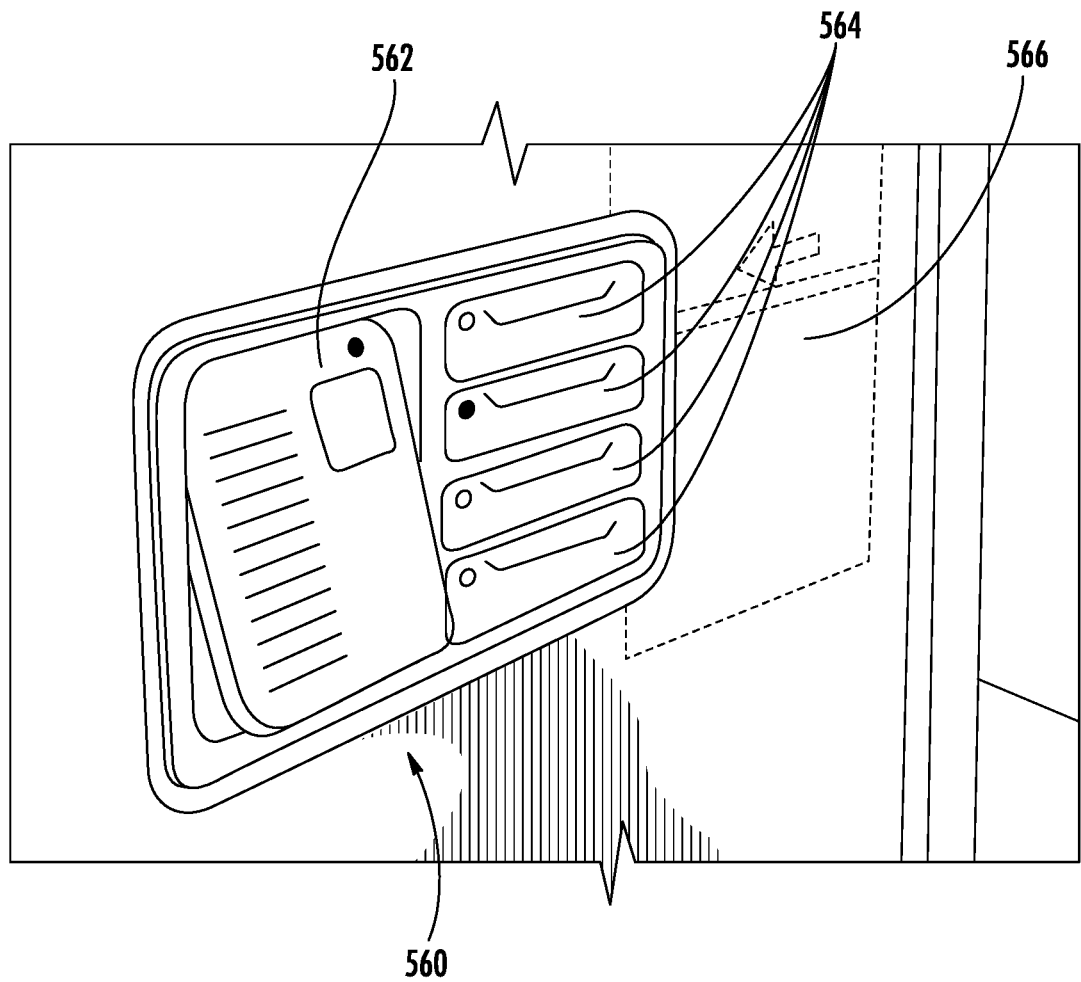
FIG. 48 illustrates a nurse server according to a further example embodiment of the present invention.

FIG. 48 provides another example embodiment of a nurse server 560 according to the present invention. The illustrated nurse server 560 may be a fully integrated nurse server that is recessed into a wall of a healthcare facility; however, embodiments may also include units extending from the wall in facilities where the wall does not provide sufficient room, or in embodiments where the nurse server and transport devices are added after construction of the facility. The depicted embodiment includes a user interface 562 and a plurality of drawers 564. The drawers may be patient specific such that all of the medication and supplies needed by a patient may be contained within a single drawer 564. In the case of a patient server, each of the drawers 564 may be time-specific for the patient served by the patient server, such that one drawer may contain medications needed for the morning, one for mid-day, and one for evening.

While the drawers 564 of the illustrated embodiment of FIG. 48 may be manually loaded, example embodiments of the present invention may provide for automatic loading of the drawers 564 via a transport device as described above. A transport device may move medications and supplies from a unit storage device to the nurse server 560 along, for example, a track, and upon arrival at the nurse server, the overpacks carried by the transport device may be moved to the appropriate drawer by a lift 566 which may be integrated into a wall of the facility or alternatively integrated into a nurse server projecting from the wall.

Each of the example embodiments of nurse servers described above may include an area configured to receive medications and supplies delivered to the nurse server but not needed or empty, returnable overpacks. The return area of the nurse server may be a drawer, bin, or other receiving area which is arranged to receive articles for return to the unit storage device or to the central pharmacy. The return area of some embodiments may stage overpacks for retrieval by a transport device for automated return of the overpacks, or alternatively, returns may be manually collected for return to the unit storage or the central pharmacy.

Figure 49:
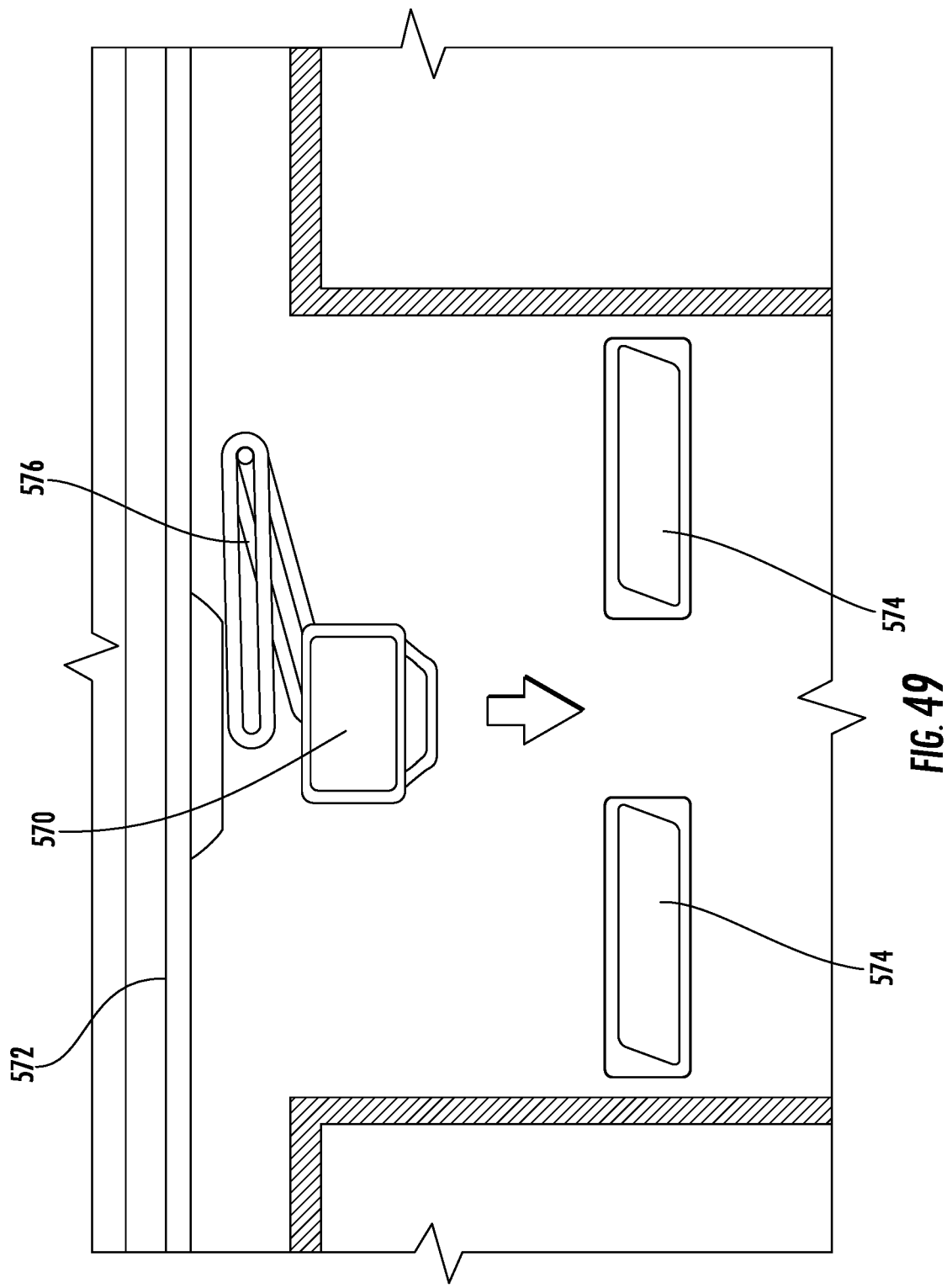
FIG. 49 illustrates a nurse server user interface according to an example embodiment of the present invention.

FIG. 49 illustrates another example embodiment of a nurse server according to embodiments of the present invention. In the illustrated embodiment, a user interface 570 is disposed on an articulated arm 576 which may include spring or weight counter-balancing to enable the user interface 570 to be easily positioned in a raised position as shown, or in a lowered position, accessible by authorized medical personnel. A nurse or other authorized medical person may arrive at the nurse station, pull the user interface 570 down to an accessible position, and upon authorization, provide a request for medication or supplies. The medication or supplies may be staged nearby, such as in the overhead storage 572 which may be track-side storage as outlined above. In response to the authorized request, the medication or supplies may be dispensed to a retrieval area 574. The authorized medical person may then retrieve the medication or supplies for administration to a patient. When the dispensing is complete, the user interface 570 may be moved back to a raised position, out of the way. The example embodiment of FIG. 49 may be implemented in healthcare facilities where hallway widths do not allow for additional, permanent structures to project from the walls.

Figure 50:
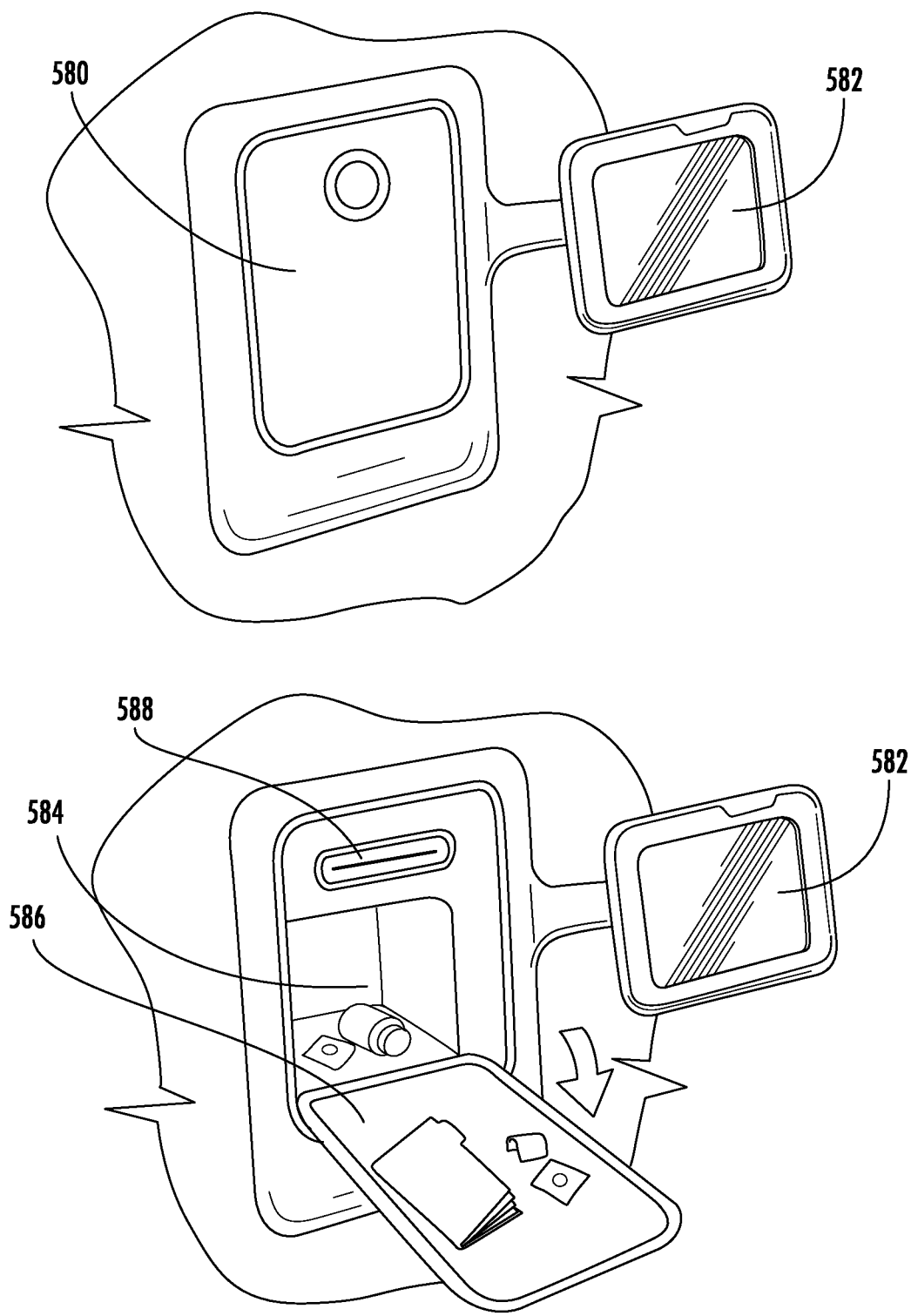
FIG. 50 illustrates a nurse server according to yet another example embodiment of the present invention.

FIG. 50 illustrates another example embodiment of a nurse server which may include a user interface 582 and an openable access panel 580. In response to an authorized medical person being identified at the user interface, the access panel 580 may be unlocked or automatically opened to provide access to the contents therein. The panel 580 may provide a work surface 586 when in the open position. The authorized medical person may retrieve medications and supplies for a patient from a retrieval area 584 disposed behind the access panel 580. The medication or supplies may be dispensed to the retrieval area by an automated transport device as described above. Unneeded medication or supplies, or returnable/reusable overpacks may be deposited in the return slot 588 for return to the unit storage device or to the central pharmacy.

Figure 51:
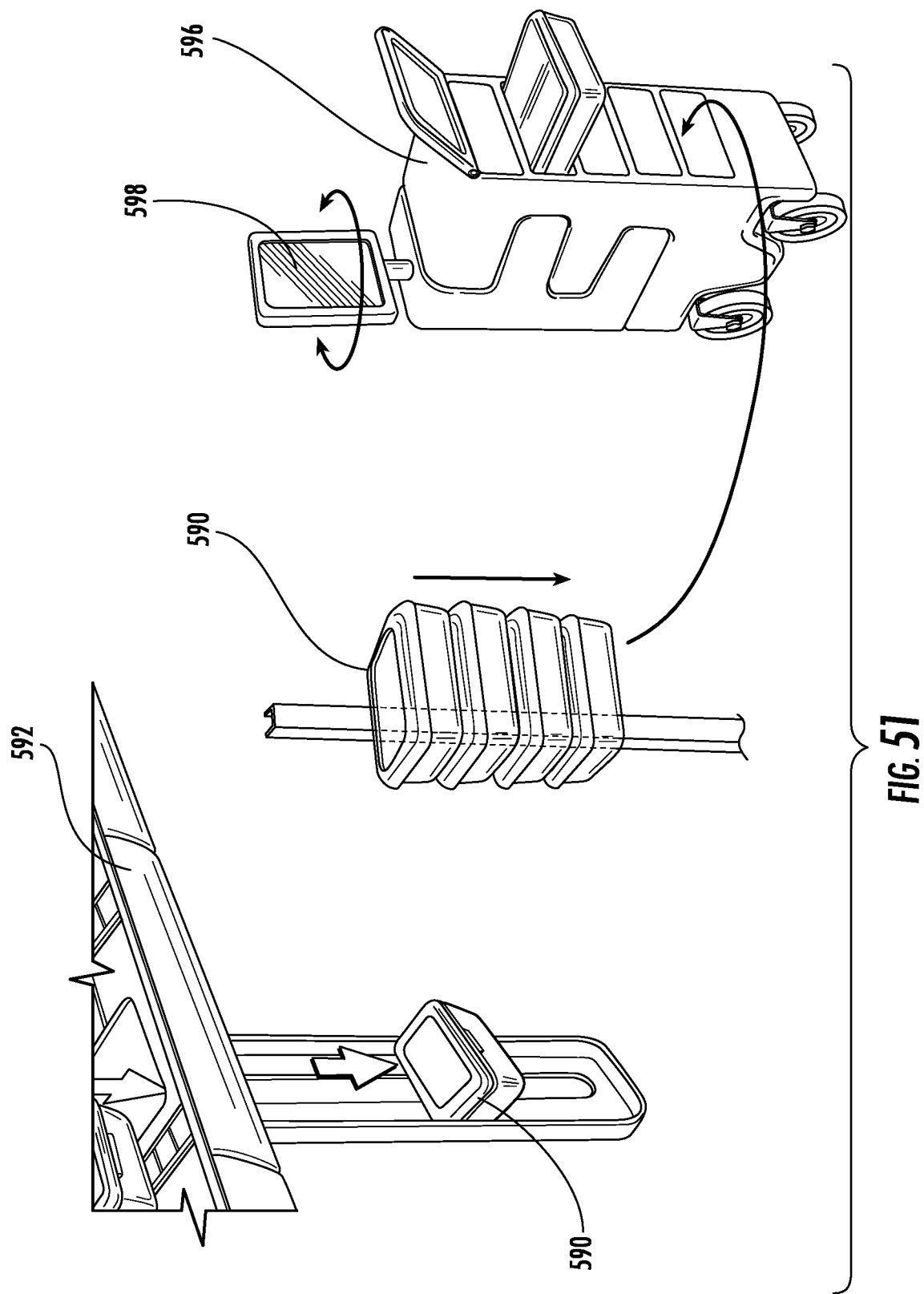
FIG. 51 illustrates an example embodiment of a nurse cart supplied by proximate storage according to the present invention.

FIG. 51 illustrates another example embodiment of a nurse server which may be embodied as a portable cart 596. The portable cart may be assigned to a nurse for use during their shift. Through a user interface, such as a user interface 598 on the cart 596, a nurse or authorized medical person may request medications and supplies for a patient or for a plurality of patients. The request may be transmitted, e.g. via a healthcare facility network, to a unit storage device. The unit storage device may load the medication overpacks onto a transport device for transport to a location proximate to the requesting nurse. Upon arrival, the nurse may be signaled that the medication has arrived. The alert may be received, for example, at the user interface 598, or other device, such as a pager or portable communication device carried by the nurse, or a healthcare facility unit dashboard (e.g., a screen displaying information at a nurse station). The nurse may then go to the proximate storage location 592 where the medications are staged, which may be, for example, in an overhead enclosure where the transport device may be disposed. The nurse may provide identification at the proximate storage location 592 through a user interface at the location, or through the user interface 598 of the cart 596, after which the medication overpacks 590 may be lowered to a location from which the nurse may retrieve them. The overpacks 590 may then be loaded into the cart for administration of their contents to the appropriate patient. The illustrated overpacks 590 may be patient specific or may be unit dose overpacks. In patient specific overpacks 590, the overpack 590 may include all of the medications needed for a patient at a particular time.

Nurse servers or patient servers according to the aforementioned embodiments may include a scanner configured to scan the medication or supplies, and/or the overpacks containing the medication or supplies. The scanner may scan identifying indicia to confirm retrieval of the scanned objects from the nurse server or patient server. The scanning may further provide an additional verification step that confirms that the appropriate medication or supply is being dispensed from the nurse server or patient server.

Nurse servers or patient servers according to the aforementioned embodiments may further include a printer. While medications transported to the nurse server or patient server may be designated for a particular patient, the patient information may not be presented on the medication, particularly since the medication or supply may be returned to the central pharmacy if it is not needed by the patient, such as if the patient is discharged before the medication is administered. As such, a printer at the nurse server or patient server may be configured to print patient information to a label to be affixed to the medication or supply, thereby designating the patient for which it is intended. The printer may print patient information in response to a scan of the medication as described above, or it may print the labels in response to the authorized medical person accessing the nurse server and retrieving the medication or supply.

In some embodiments, nurse servers may include temperature controlled areas. For example, in the embodiment of FIG. 48, one or more of the drawers 564 may include a refrigerated compartment to maintain refrigerated medications at the appropriate temperature until dispensed. In such an embodiment, a printer may be configured to print a label for the medication upon dispensing which identifies the time at which it was dispensed, which may correspond to the time the medication was removed from refrigerated storage. In such an example, the medication may have a maximum shelf-life outside of refrigerated storage after which the medication is no longer fit for administration to a patient. The time after which the medication must be disposed may be printed to the label when the medication is dispensed from the nurse server. Optionally, "printing" may be performed by writing to an RFID tag or writing to an electronic ink label.

As outlined above, some medication may require refrigeration to maintain its efficacy. Such medications may be given a maximum shelf-life outside of refrigeration. The shelf-life of such a medication may be a time since the medication was initially removed from refrigeration, or a cumulative time of the medication outside of refrigeration. According to embodiments of the present invention, as transportation and storage of medications may be automated and controlled, the logistics software for routing (i.e., mapping out a route for) and dispensing of medications may be configured to monitor the time of a medication outside of refrigerated storage. For example, a medication may be outside of refrigerated storage between the central pharmacy and the unit storage device. At the unit storage device, the medication may be maintained in a refrigerated storage area. The medication may again be outside of refrigerated storage during transport to proximate storage near a patient. Upon arrival at the proximate storage, the medication may or may not be stored in a temperature controlled location. As such, the software may monitor the cumulative length of time the medication is outside of refrigerated storage. If the medication is outside of refrigerated storage longer than the shelf-life outside of refrigerated storage, the medication may be automatically routed back to the unit storage device and/or to the central pharmacy. If the medication has shelf-life remaining at the time of dispensing, the time remaining may be displayed to a nurse on a user interface of a nurse server or patient server, or optionally printed to a label for the medication.

According to example embodiments of the invention, temperature sensitive medications or supplies may be packaged in overpacks that include temperature monitoring capabilities. The temperature monitoring may be performed by a temperature monitoring strip which displays the time that the strip or the products attached thereto, have been exposed to temperatures exceeding a threshold. Temperature monitoring may also be performed by an RFID tag configured to generate a temperature profile which may be analyzed when the information is read from the tag. Use of temperature monitoring may allow inventory monitors or controls to determine if a medication has exceeded a maximum temperature or exceeded a maximum time above a threshold temperature, in which case the medication would be returned to a central pharmacy for disposition.

Overpacks may also be configured to maintain a temperature of a medication. For example, an overpack may be insulated and may contain a cold-pack configured to keep the temperature inside the overpack below a threshold value. Overpacks may also include material, such as a phase change material, configured to maintain overpack contents at or around a desired temperature. Such overpacks may be used to extend the shelf-life of a medication or to allow transportation of medications outside of refrigerated storage for a longer period of time.

As noted above, embodiments of the present invention may require identification of the authorized medical person before providing access to the medication or supplies dispensed by the nurse server or patient server. Identification of appropriate medical personnel may be accomplished by the scanning of an identification card which may include a barcode or RFID tag. Alternatively, identification of authorized medical personnel may be accomplished by biometric scanning, such as a scan of a person's retina, finger print, hand geometry, palm vein, face, or voice to determine the identification of the person. Identification may also be provided by a personal identification number (PIN), or any combination of the aforementioned mechanisms.

Appropriate identification of medical personnel may be important to preclude unauthorized access to medications and to satisfy regulatory requirements. Requiring medical personnel to properly identify themselves may also preclude a nurse from accessing the wrong nurse server by limiting the medical personnel authorized to access a particular nurse server or patient server. Further, requiring identification of medical personnel may provide an audit trail to identify who retrieved medication for a particular patient.

Nurse servers or patient servers as described above may be configured to provide an estimated time of arrival for medications or supplies at a nurse server or patient server. For example, a nurse may enter a request for a medication or supply to be dispensed from a nurse or patient server, and the user interface may provide an estimated time of arrival for the medication or supply at the nurse or patient server. According to some embodiments, the medication or supply may be staged for immediate dispensing; however, some medications or supplies may not be present at the patient server or nurse server. Providing an estimated time of arrival for the medication or supply may allow an authorized medical person to perform other tasks while awaiting delivery of the medication or supply. As embodiments described above may include substantial automation of the retrieval and delivery of medications and supplies to locations proximate to a patient, logistic software configured to route the medication and supplies may be able to provide a very accurate estimated time of arrival of the requested medication or supply at the nurse server or patient server.

As described above, the nurse server or patient server may be used to interface with a network of a healthcare facility to ensure accurate dispensing of medications to authorized personnel. The automation and the transfer of data and information may be implemented in various embodiments of the present invention. As used herein, where a computing device is described herein to receive data from another computing device, such as receiving an indication of medication required, it will be appreciated that the data may be received directly from the another computing device and/or may be received indirectly via one or more intermediary computing devices, such as, for example, one or more servers, relays, routers, network access points, and/or the like. Similarly, where a computing device is described herein to send data to another computing device, it will be appreciated that the data may be sent directly to the another computing device or may be sent to the another computing device via one or more interlinking computing devices, such as, for example, one or more servers, relays, routers, network access points, and/or the like.

In some example embodiments, processes and steps of the invention may be carried out by computing devices that may be in communication with a network, such as an information network of a healthcare facility. The computing devices may include nurse servers, patient servers, portable communications stations, or the like. Such a network may be embodied in a local area network, the Internet, any other form of a network, or in any combination thereof, including proprietary private and semi-private networks and public networks. The network may comprise a wire-line network, wireless network (e.g., a cellular network, wireless local area network, wireless wide area network, some combination thereof, or the like), or a combination thereof, and in some example embodiments comprises at least a portion of the Internet.

In some example embodiments, computing devices configured to perform various operations of the invention may include computing devices, such as, by way of non-limiting example, a server, configured to access a network and/or server(s). In some example embodiments, computing devices may be implemented as a distributed system or a cloud based entity that may be implemented within a network. In this regard, a computing device according to the present invention may comprise one or more servers, a server cluster, one or more network nodes, a cloud computing infrastructure, some combination thereof, or the like. Additionally or alternatively, embodiments may be implemented as a web service.

Further example embodiments of the present invention may include a system comprising any number of user terminals. A user terminal may be embodied as a laptop computer, tablet computer, mobile phone, desktop computer, workstation, nurse server, patient server, or other like computing device.

The computing device of example embodiments may include processing circuitry. The processing circuitry may be configured to perform actions in accordance with one or more example embodiments disclosed herein. In this regard, the processing circuitry may be configured to perform and/or control performance of one or more functionalities of the handling, transporting, storing, or distributing of medications and/or supplies in accordance with various example embodiments. The processing circuitry may be configured to perform data processing, application execution, and/or other processing and management services according to one or more example embodiments. In some embodiments, computing device or a portion(s) or component(s) thereof, such as the processing circuitry, may be embodied as or comprise a circuit chip. The circuit chip may constitute means for performing one or more operations for providing the functionalities described herein.

Figure 52:
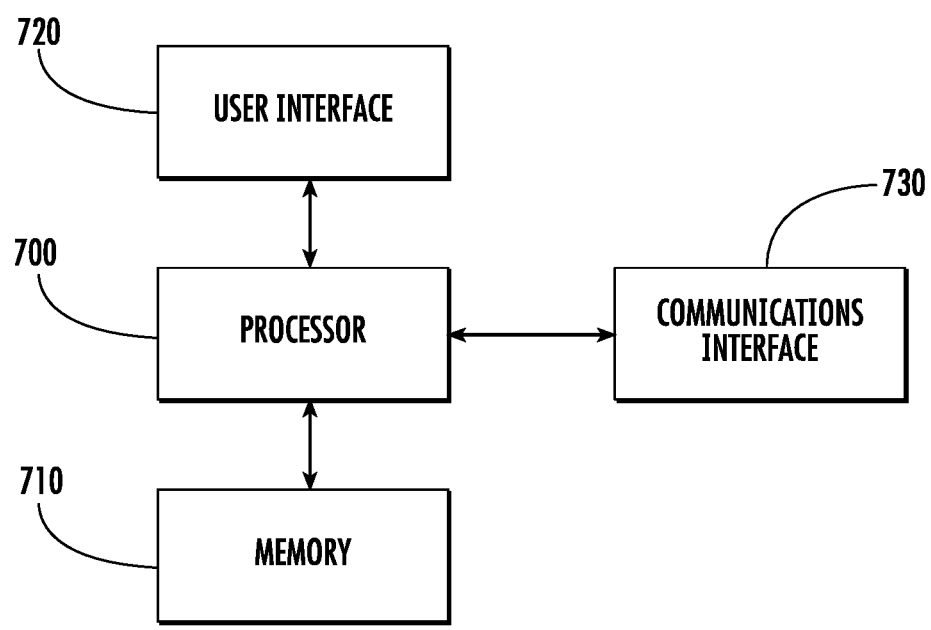
FIG. 52 is a schematic illustration of a user terminal according to an example embodiment of the present invention.

A schematic illustration of an apparatus which may be implemented as a nurse server, patient server, or user terminal in a central pharmacy or unit storage device is illustrated in FIG. 52. As shown, in some example embodiments, the processing circuitry may include a processor 700 and, in some embodiments, may further include memory 710. The processing circuitry may be in communication with, include or otherwise control a user interface 720 and/or a communication interface 730. As such, the processing circuitry may be embodied as a circuit chip (e.g., an integrated circuit chip) configured (e.g., with hardware, software, or a combination of hardware and software) to perform operations described herein.

The processor 700 may be embodied in a number of different ways. For example, the processor may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of a system for handling, storing, transporting, or distributing medication as described herein. The plurality of processors may be embodied on a single computing device or distributed across a plurality of computing devices. In some example embodiments, the processor may be configured to execute instructions stored in the memory or otherwise accessible to the processor. As such, whether configured by hardware or by a combination of hardware and software, the processor may represent an entity (e.g., physically embodied in circuitry—in the form of processing circuitry) capable of performing operations according to embodiments of the present invention while configured accordingly. Thus, for example, when the processor is embodied as an ASIC, FPGA, or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 710 may include one or more non-transitory memory devices such as, for example, volatile and/or non-volatile memory that may be either fixed or removable. In this regard, the memory 710 may comprise a non-transitory computer-readable storage medium. It will be appreciated that while the memory 710 is illustrated as a single memory, the memory may comprise a plurality of memories. The plurality of memories may be embodied on a single computing device or may be distributed across a plurality of computing. The memory may be configured to store information, data, applications, instructions and/or the like for enabling embodiments of the present invention to carry out various functions in accordance with one or more example embodiments. For example, the memory may be configured to buffer input data for processing by the processor. Additionally or alternatively, the memory may be configured to store instructions for execution by the processor. As yet another alternative, the memory may include one or more databases that may store a variety of files, contents, or data sets. Among the contents of the memory, applications may be stored for execution by the processor to carry out the functionality associated with each respective application.

A user interface 720 of example embodiments, such as the user interface of a nurse server or patient sever, may be in communication with the processing circuitry to receive an indication of a user input at the user interface and/or to provide an audible, visual, mechanical, or other output to the user. As such, the user interface may include, for example, a user input interface 720 such as a keyboard, a mouse, a joystick, a display, a touch screen display, a microphone, a speaker, and/or other input/output mechanisms. As such, the user interface may 720, in some example embodiments, provide means for user control of embodiments of the present invention. In some example embodiments in which the invention is embodied as a server, cloud computing system, or the like, aspects of user interface may be limited or the user interface may not be present. In some example embodiments, one or more aspects of the user interface may be implemented on a user terminal. Accordingly, regardless of implementation, the user interface may provide input and output means to facilitate handling, storing, transporting, or delivery of medication in accordance with one or more example embodiments.

The communication interface 730 may include one or more interface mechanisms for enabling communication with other devices and/or networks. In some cases, the communication interface may be any means such as a device or circuitry embodied in either hardware, or a combination of hardware and software that is configured to receive and/or transmit data from/to a network and/or any other device or module in communication with the processing circuitry. By way of example, the communication interface 730 may be configured to enable embodiments of the present invention to communicate with application server(s) and/or networks and/or information databases. Accordingly, the communication interface may, for example, include supporting hardware and/or software for enabling communications via cable, digital subscriber line (DSL), universal serial bus (USB), Ethernet, or other methods.

A First Example Embodiment of a System

While various components of a system for automating the dispensing of medications and supplies to patients within a healthcare facility have been described above, an example embodiment using components of the system is described herein to further illustrate the functionality of such a system.

The example embodiment system described herein is described with respect to a healthcare facility including multiple units, such as an intensive care unit, a long-term care unit, a psychiatric unit, a maternity unit, etc. Embodiments may include a central pharmacy configured to dispense medication to patients in each of the units of the healthcare facility. As such healthcare facilities may provide medication and supplies to hundreds of patients, each requiring a unique medication regimen, automation of medication distribution can be difficult. Further, medication regimens can change based on a patient's changing conditions or a patient's response to previously administered medications. Automated systems to dispense medications in such an environment may require flexibility to change medication regimens for individual patients as needed, and also provide medication as it is needed, where it is needed in the healthcare facility.

Embodiments of systems according to the present invention may provide a system for predicting the medications which may be needed by a patient over a specific period of time. The prediction may be performed by software which may be configured to use a variety of methods to determine what medications and supplies may be required over a specific period of time. The predicted medication and any known medication (e.g., medication previously prescribed) may constitute a medication order. The medication order may be sent (e.g., by a healthcare facility network), to a central pharmacy for fulfillment.

The central pharmacy of a healthcare facility may be configured to receive a medication order and to fulfill the medication order by picking the medications of the medication order from a supply of medications. The picking may be performed manually by a pharmacist or pharmacy technician, or the picking may be performed automatically by an automated dispensing system, such as a Robot-Rx™ from McKesson®. The medication, whether picked manually or automatically, may be packaged into overpacks, if not already in a suitable package for automation. For example, the types of packages handled by the Robot-Rx™ may be compatible with some embodiments of automation such that repackaging is not necessary. In other embodiments, the medication, if contained in a package, such as a blister pack, may require packaging in an overpack that is compatible with specific automation systems. In the instant embodiment, picked medications are loaded into bins, such as the bins 102-108 of FIG. 1, which are configured to be compatible with various automation components and systems described herein.

Supplies may also be part of the medication order as determined by the software (e.g., a syringe of a given size may be known by the software to accompany a medication vial of a given size). Optionally, supplies may be added to a medication order manually, for example when authorized medical personnel recognize a need (e.g., a patient's IV tubing is punctured requiring new IV tubing to be ordered). In example embodiments in which the central pharmacy and the central supply store are collocated, or in close proximity to one another, after medications are loaded into overpacks, the requisite supplies may also be loaded into the overpacks before the overpacks are grouped and transported to the unit storage device. Additionally or alternatively, particularly in embodiments in which the central supply store and the central pharmacy are not in close proximity, supplies may be loaded to separate overpacks. The overpacks of supplies may be grouped according to location and transported accordingly. The unit storage device may be configured to associate a supply with a medication for distribution to an authorized medical person.

The medications for a medication order for a patient may each be loaded into separate bins, such that the bins each contain a unit dose of medication. Supplies may also be loaded into individual bins. In some cases, supplies which correspond to a particular medication may be loaded into the same overpack bin as the medication to which they are associated. The overpacks may be loaded manually by a pharmacy technician or pharmacist, or the overpacks may be loaded automatically, as illustrated in FIG. 6. Appropriately sized bins may be selected based upon the size of the medications or supplies to be received therein. In some embodiments, software may designate the size of bin to be used for a particular medicine or supply, which may be preferred in embodiments implementing an automated overpack fill.

A label may be applied to each overpack to identify the contents received therein and/or to identify the patient for whom the overpack is intended. The overpack label may include identifying indicia such as a barcode, text, picture, etc. Optionally, an RFID tag on the overpack may be written to by an RFID encoder. The RFID tag may be written with the patient information, patient location, medication information, etc. Labels for overpacks which are intended for multiple uses may be temporarily affixed such as with a releasable adhesive, a hook-and-loop fastener system, or received within a label receiving area of the overpack, such as a transparent pouch.

Including only a single dose of medication in each overpack may allow each labeled overpack to be individually manipulated throughout the dispensing process. For example, when the overpack is at the central pharmacy, transported to the unit storage, at the unit storage, in proximate storage, or at the nurse server or patient server, the unit dose overpack may be identified by the label and manipulated as needed. In an embodiment in which a particular medication was removed from a person's medication regimen, the unit dose of that medication may be removed and routed for return to the central pharmacy at various points during the dispensing process.

In some embodiments wherein each overpack contains a unit dose medication, each overpack may be individually routed to the patient for whom it is intended. For example, upon determining that a medication is anticipated to be needed by a patient, logistics software may plan a route for the individual unit dose between the central pharmacy and the proximate storage. The route may be the same as other medications destined for the same patient; however, as each medication unit dose is individually traceable and manipulated, each overpack may have an individual route that is assigned to it. Grouping of overpacks with similar destinations may be another function of the logistics software; however, each overpack maintains its unique identity and route. As such, if a group of medications is separated during loading/unloading or transport, each of the overpacks will still arrive at the appropriate destination. Further, if an individual medication is flagged for removal from the patient's medication order, the route of that medication may be changed to re-route the medication back to the central pharmacy.

Individual routing of medications may allow individual control of the medications, such as when a medication must be removed from a patient's regimen due to a lot recall, expiration of medication, a change associated with the patient status (e.g., improving/worsening condition, discharge of patient, movement of patient to another location, etc.), a more urgent need for a medication for another patient, etc.

Embodiments may use unit-dose overpacks; however, additionally or alternatively, all of the medications and supplies for a patient that may be needed over a specific time period may be grouped together into a single overpack. Such an embodiment may reduce the overall number of overpacks needed for a facility and may increase the efficiency of dispensing the medications and supplies; however the ability to individually manipulate unit doses automatically may be lost. Some medications may be grouped together by their purpose, for instance a medication that includes nausea as a side effect may be grouped with an anti-nausea medication. As such, removing the medication with a side effect removes the need for the nausea medication, such that the medications may be grouped together in a single overpack without the need to track them individually.

While the above embodiment has been described with respect to a central pharmacy of a healthcare facility, the central pharmacy role may be removed from the healthcare facility and may be implemented in a remote location. A remote central pharmacy may be a pharmacy which serves multiple healthcare facilities and may benefit from economies of scale, particularly when servicing smaller healthcare facilities. As such, embodiments of the above may be implemented at a remote central pharmacy where the overpacks are prepared off-site, and subsequently delivered to a healthcare facility for distribution to healthcare facility units and/or patients.

The overpack bins of the above described embodiment may be staged in a location at the central pharmacy (or at a receiving location within a healthcare facility) and may be grouped according to their destination. For example, overpacks that are designated to go to a patient on the long-term care unit may be grouped together, while overpacks designated to go to an intensive care unit (ICU) may be grouped together. The grouping of overpacks together may be performed automatically, for example by the logistics software that routes medications to the appropriate patients. Optionally, the grouping of overpacks may be performed manually.

The grouping of overpacks may include placing the bins on a tray, as illustrated in FIG. 11. The bins may be lidded bins, or a lid may be placed over the group of bins on the tray as illustrated. The grouped overpacks may then be loaded onto a transport cart, as shown in FIG. 18, for transport to the appropriate local storage or unit storage device.

The transport cart may be moved automatically, for example, using an automated guided vehicle, or the cart may itself be an automated guided vehicle. In other embodiments, the cart may be moved manually to the unit storage device in the appropriate unit of the healthcare facility.

Upon arrival at the unit storage device, as shown in FIG. 20, a tray containing the overpacks may be removed from the cart, and loaded into the unit storage device. The lid from the tray may be removed, and the tray may be loaded into the unit storage device. Optionally, the overpacks may be loaded into the unit storage device without the tray, and the tray and lid may be returned to the cart for return to the central pharmacy.

The transport cart may include only medications and supplies for a specific unit of a healthcare facility, or optionally, the transport cart may include trays of overpacks for different units of a healthcare facility. In such a case, the trays designated for a first unit storage device may be loaded into the first unit storage device, while trays designated for a second unit storage device may be loaded into a second unit storage device as the transport cart makes rounds delivering the appropriate trays to the appropriate unit storage device.

The unit storage device may be configured with a retrieval device as illustrated in FIG. 23, which may include an X-Y robot arranged to traverse the unit storage device. The overpacks may each be accessible to the retrieval device as the X-Y robot moves the retrieval device across the unit storage device. As outlined above, the medications for a medication order may be needed for a specific time period. The medications may be stored within the unit storage device until such time as the medications are anticipated to be needed, or when they are actually needed. In an example embodiment, the medications of a medication order are retrieved in advance of the time at which they are anticipated to be needed. The overpacks may be staged proximate a transport device, such as the train of FIG. 23. Before the time that the medications are anticipated to be needed, a loading device may load the overpacks containing the medication order onto a transport device.

Figure 53:
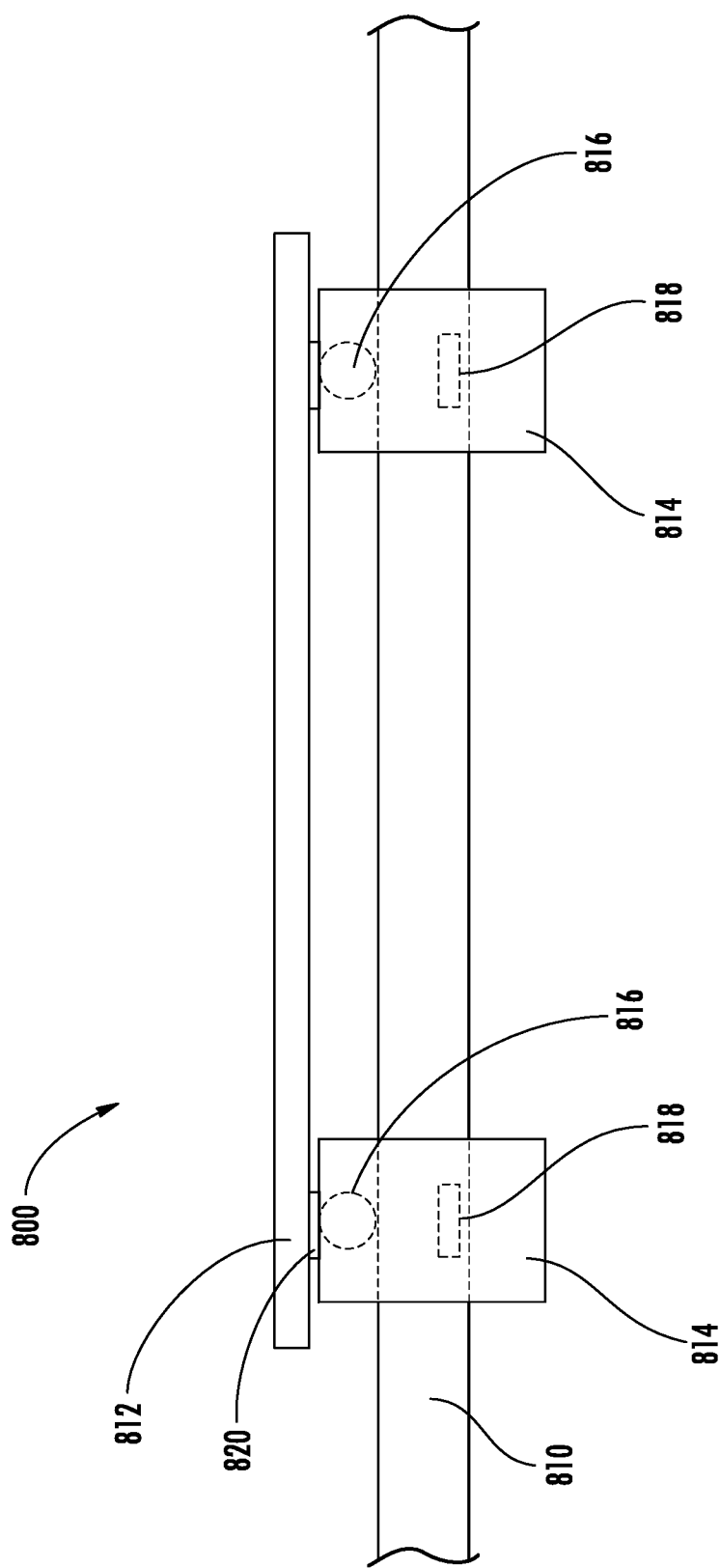
FIG. 53 illustrates a car for a track-based transport system according to an example embodiment of the present invention.

A transport device according to example embodiments of the present invention may include a train car with one or more bogies adapted to ride along a rail. FIG. 53 illustrates a side view of an example embodiment of a train car 800 configured to advance along track 810. The train car 800 includes a load surface 812 arranged to carry medication and supply overpacks. The load surface 812 may be configured to carry any specific kind of overpack securely. For example, in the case of the bin-type overpacks, the train car may be equipped with a top that is arranged proximate the top of the bins loaded into the train car. The top may be configured to prevent shifting and moving of the overpacks as the train car travels along the rails. The illustrated train car 812 further includes bogies 814 which are configured to ride along the rail 810. The bogies may each include at least one top roller 816 adapted to ride along the top of the rail 810, and a pair of side rollers 818 arranged on either side of the rail 810 and adapted to keep the bogie 814 centered on the track 810. The bogies 814 may each be pivotably connected to the load surface 812 by pivot points 820. The pivot points 820 may allow the bogies 814 to turn relative to the load surface 812 such that the train car can advance around bends. The length of the train car 800 (or the length between the bogies) and the pivotability of the bogies 814 may determine the minimum radius track turn that can be used in a system using the train cars 800.

The train car 800 may be advanced along the track by a drive wheel, which may be one or more of the top rollers 816 and/or side rollers 818. Embodiments may include a local energy source disposed on the train car, such as a battery, which may drive an electric motor to turn the drive wheels. Optionally, the track may include bus bars to conduct electricity along the track from which the train car 800 may tap into. As such, the track may provide power to the motor which drives the drive wheels. Other mechanisms for advancing the train car along the track may include a cable disposed within or proximate to the track which may pull the train car along the track. A cable disposed within the track may be configured in a continuous loop through the track disposed in an overhead location of a healthcare facility unit. The cable may move substantially constantly, and the train may be adapted to engage the cable to advance the train, and disengage the cable to stop the train. Other embodiments may include a magnetic levitation system adapted to advance the train car along the track.

The transport device may receive the overpacks as outlined above, and then transport the overpacks to proximate storage. The overpacks may be staged at the proximate storage, or at a nurse or patient server as outlined above. In some embodiments, the transport device is staged along with the overpacks.

As illustrated and described above with reference to FIG. 29, a train car according to example embodiments may include a scanner 404 configured to read the identifying indicia of the overpacks. The scanner may be disposed on the train car configured to scan overpacks to be loaded; however, scanners may also be implemented at the proximate storage staging area, the unit storage device, and the nurse server. Scanners may be implemented to provide additional tracking and confirmation of the arrival of medications at particular locations. For example, a proximate storage location may include a scanner which scans the overpacks on a transport device that has arrived at the proximate storage location, and direct unloading of the overpacks that are to be staged at the proximate location.

Embodiments of a transport device according to the present invention may include a system for tracking the location of the transport device. Such a system may include radio frequency beacons disposed along the track and an RFID tag on the train car. Such a system could identify the location of the train car anywhere along the track with high accuracy. Other embodiments may include sensors disposed along the track configured to detect the presence of a train car and to scan an identity of the train car to determine and track the train car's location. In other embodiments, location codes may be disposed about the track. The location codes may be in the form of RFID tags, barcodes, or other indicia which may be read by a scanner of a train car. The train car may scan the indicia along the track and provide that information to a system tracking the location of the train car. As such, the specific location of a train car and the contents thereon may be known throughout the transport process.

When an authorized medical person is prepared to administer medication to a patient, they may access a nurse server or patient server according to any of the embodiments described above. The authorized medical person may access the user interface of nurse server or patient server by identifying themselves and the nurse server confirming that they are an authorized medical person. In an example embodiment in which no user interface may be present, such as the nurse server of the embodiment of FIG. 51, the staged medication may be dispensed to the authorized medical personnel. In an example embodiment in which a user interface is present on the nurse server, the authorized person may select the patient or simply accept the medication that is staged awaiting dispensing. Thereafter, the medication may be dispensed to the authorized medical person.

To dispense the medication from the overpacks of the aforementioned example embodiment, the bins may be tilted or "dumped" to have the contents dispensed from the nurse server. The nurse server may include structure sufficient to slow the descent of the medications and supplies to accommodate a relatively soft landing at the dispensing area of the nurse server. Alternatively, the overpack bins may be lowered through the nurse server and presented to the authorized medical person for retrieval of the medications and supplies. The empty overpacks may be returned to the nurse server, which may return the overpacks to the transport device, or to the staging area configured to be retrieved by the transport device. The transport device may return empty overpacks or overpacks containing unused or unneeded medications back to the unit storage device. The empty overpacks and unneeded medications may be retrieved and returned to the central pharmacy for reuse.

A Second Example Embodiment of a System

Another example embodiment of a system incorporating various components outlined above is described herein. According to an example embodiment, a system may be configured to deliver medications that are anticipated to be needed by a patient ahead of the anticipated need. In one embodiment, a system may be configured to predict the needs of patients in a healthcare facility. The system may predict the anticipated medication needed by the patient using a variety of manners, such as one or more of a conventional medication regimen for a particular ailment, a physician specific medication regimen for a particular ailment, a historical record of unit dose medications, or an algorithm. The algorithm may predict the anticipated medications needed by a patient by factoring in patient conditions, symptoms, patient information (e.g., gender, age), etc. The algorithm may determine a medication or plurality of medications which may be used to treat a patient with the combination of symptoms and conditions.

Upon predicting the medications anticipated to be needed by a patient, the medication order, including each of the anticipated medications, may be sent to a central pharmacy. The central pharmacy may manually or automatically fulfill the medication order. For example, a Robot-Rx™ automated dispensing system may receive the medication order and dispense each of the medications anticipated to be needed by the patient. The medications may be loaded into overpacks; however, in the case of an automated dispensing system, the medications may already be contained in packages which are suitable for automated dispensing. As such, the medications dispensed by an automated dispensing system may be ready to be loaded into a carrier according to example embodiments of the present invention. Medications which may not already be packaged in packaging suitable for automated manipulation may be packaged into such overpacks. In the example embodiment, the overpack may include a bag, such as the bag illustrated in FIG. 4. The bag may include a hole 142 to provide a grasping and holding location for automated devices.

Figure 54:
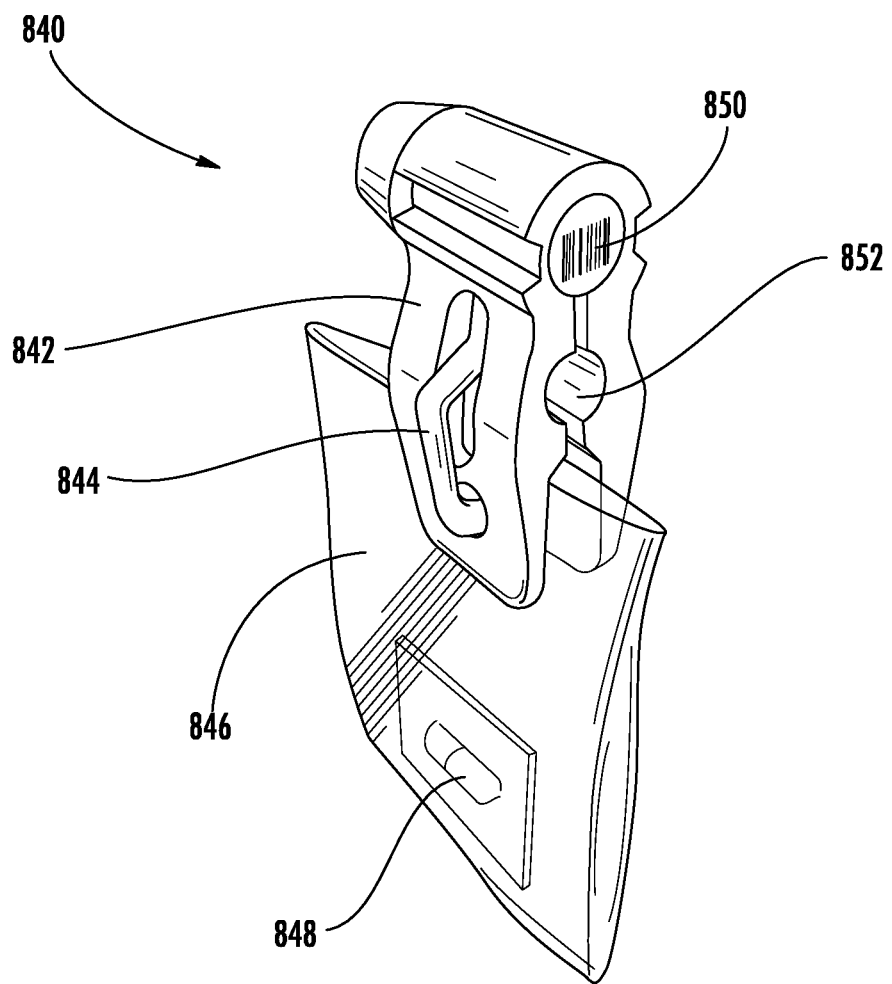
FIG. 54 illustrates a clip for holding a medication overpack according to an embodiment of the present invention.

The medication, which is now packaged into overpack packaging suitable for automated handling, may be loaded into an apparatus which may be compatible with further automated handling and transporting of the medications. FIG. 54 illustrates an example embodiment of a clip 840 including a clip body 842 and a hook 844. The clip 840 may be configured to securely hold an overpack 846, such as the bag overpack described above and illustrated in FIG. 4. The overpack 846 may contain a unit dose medication 848, or alternatively, a plurality of unit dose medications each anticipated to be needed by a single patient. In such an embodiment, the overpack is patient-specific rather than medication-specific. The clips of example embodiment may be configured to be manually loaded by, for example a pharmacy technician, or alternatively, the clips may be automatically loaded by a device configured to insert the overpacks 846 into the clips 840.

Figure 55:
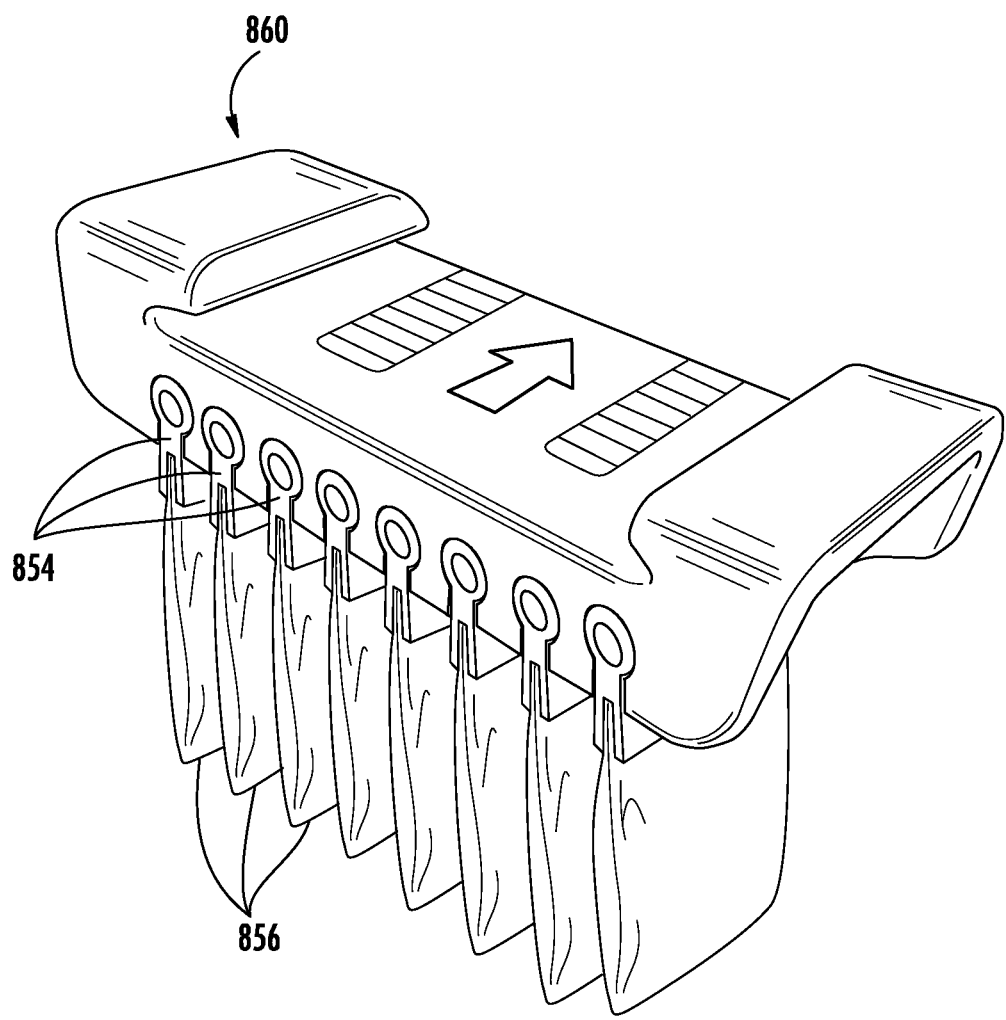
FIG. 55 illustrates a carrier configured to carry a plurality of clips with overpacks according to an example embodiment of the present invention.

The clip 840 of the illustrated embodiment may include identifying indicia 850 disposed on an area of the clip which will remain visible during transport such that the identifying indicia can be scanned. Optionally, the identifying indicia may be stored in an RFID tag which may be readable without being visible. The clip 840 of FIG. 54 further includes a release recess 852 as will be described further below. FIG. 55 illustrates an example embodiment of a carrier 860 configured to carry a plurality of clips 854 with overpacks 856. The clips may be received into recesses of the carrier which securely hold the clips 854 in place during transport of the carrier. The clips may be manually or automatically loaded into the carrier.

Each carrier may be designated as bound for a specific location within a healthcare facility. For example, a carrier may be routed to the intensive care unit. Carriers may be configured to hold medications for a plurality of patients proximate their destination, or alternatively, particularly when a patient has a large number of medications, a carrier may be configured to hold only medications for a single patient. The carriers may be loaded onto a transport cart, as illustrated in FIG. 19 for transport to a unit of the healthcare facility. As illustrated in FIG. 19, upon arrival at the appropriate unit, the carriers for that unit may be unloaded from the transport cart and loaded into a unit storage device. The unit storage device may be any of the unit storage devices outlined above that are compatible with carriers as described herein. For example, carriers may be loaded into a unit storage device as illustrated in FIG. 25.

As described above with respect to FIG. 28, the carriers may be configured to be loaded onto a shuttle for transport to a location proximate a patient. The carriers may be temporarily stored at the unit storage device. A carrier may be stored until such time as a request is received for a medication unit dose contained in an overpack attached to the carrier. Optionally, the logistics software may anticipate the time that a medication is needed at a location proximate the patient and advance the carrier toward a transport device for transport to the location proximate the patient in advance of the anticipated need.

According to some embodiments, the unit storage device may only be configured to load the carriers onto a transport device, and not provide staging at the unit storage device. In such an embodiment, carriers may be moved to a location proximate the patient when a transport device is available rather than awaiting a request for a medication or a prediction of a need for the medication. Once the carrier is loaded onto a transport device, for example, as shown in FIG. 28, the transport device may advance the carrier to a location proximate the patient or patients for whom the medication of the overpacks of the carrier are for. The carrier may be staged at the location proximate the patient, which may be in proximate storage, at a nurse server, or at a patient server.

Figure 56:
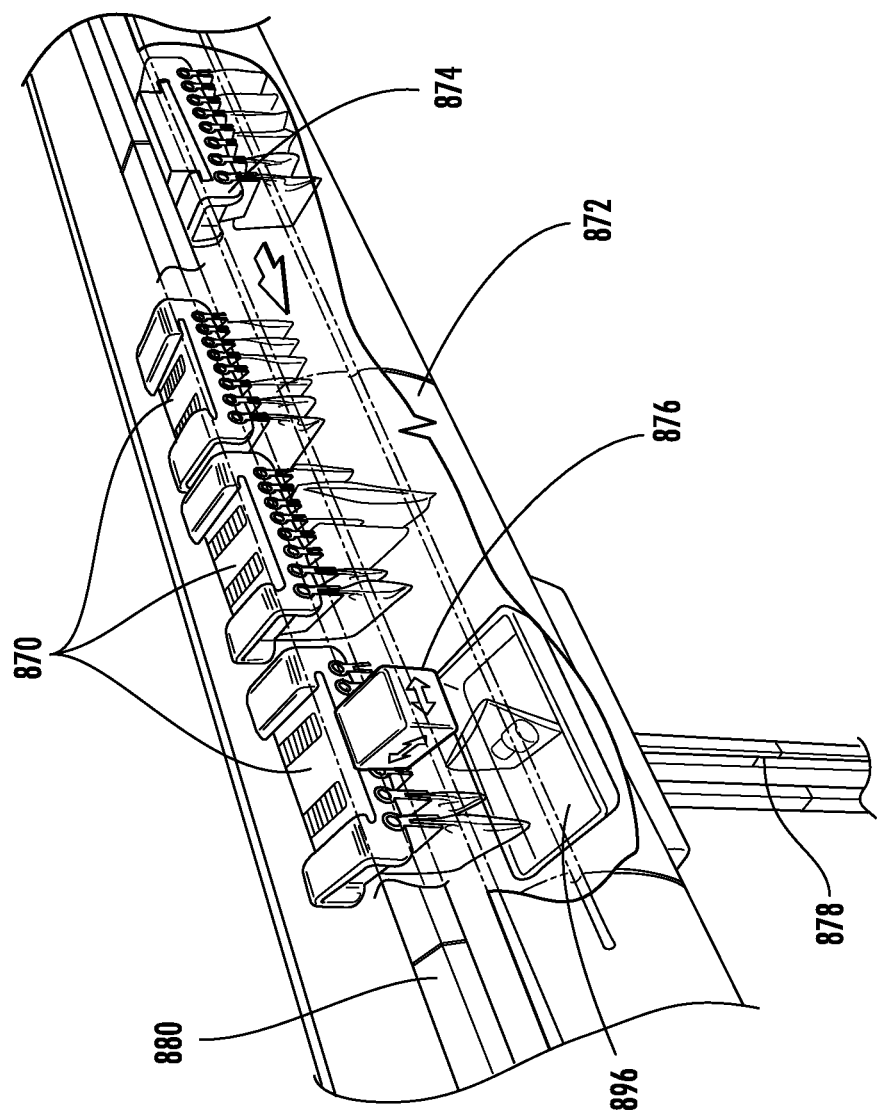
FIG. 56 illustrates a track-based transport system for carriers of overpacks on clips according to an example embodiment of the present invention.

FIG. 56 illustrates an example embodiment of several carriers 870 staged in proximate storage near a nurse server which receives medications along track 878. The proximate storage may be a location track side away from track 880 to allow other carriers 874 to move along the track 880. The track-side storage may be on a track spur or track loop as outlined above, or the carriers may be moved off of shuttles into a storage or holding area by a loading/unloading device at the proximate storage location. The track 880 and the proximate storage location for the carriers 870 may be enclosed in an overhead location, such as by enclosure 872 to keep the medications secure, to keep noise to a minimum, and to avoid potential interference with the carriers and shuttles.

Authorized medical personnel may be alerted that medication is staged at the proximate storage and ready for dispensing. The alert may be in the form of a light at the proximate storage or nurse station indicating that staged medication is present and ready to be dispensed. Optionally, an alert may be sent via wireless network to a portable device, such as to a pager, a nurse cart, a tablet computer, handheld computer, etc. The authorized medical person responsible for administering the medication to the patient may respond to the alert in due course.

Upon arrival at the nurse server or patient server, the authorized medical person may identify themselves to confirm to the patient server or nurse server that they are, indeed authorized. The identification may be performed as outlined above with regard to the various embodiments of a nurse station. In response to confirming the identity of the authorized medical person, the nurse server or patient server may provide an indication of the medications available for dispensing, or an indication of the patients for whom medications are available for. The authorized medical person may select the medications and/or patients to initiate the dispensing of the medications.

Figure 57:
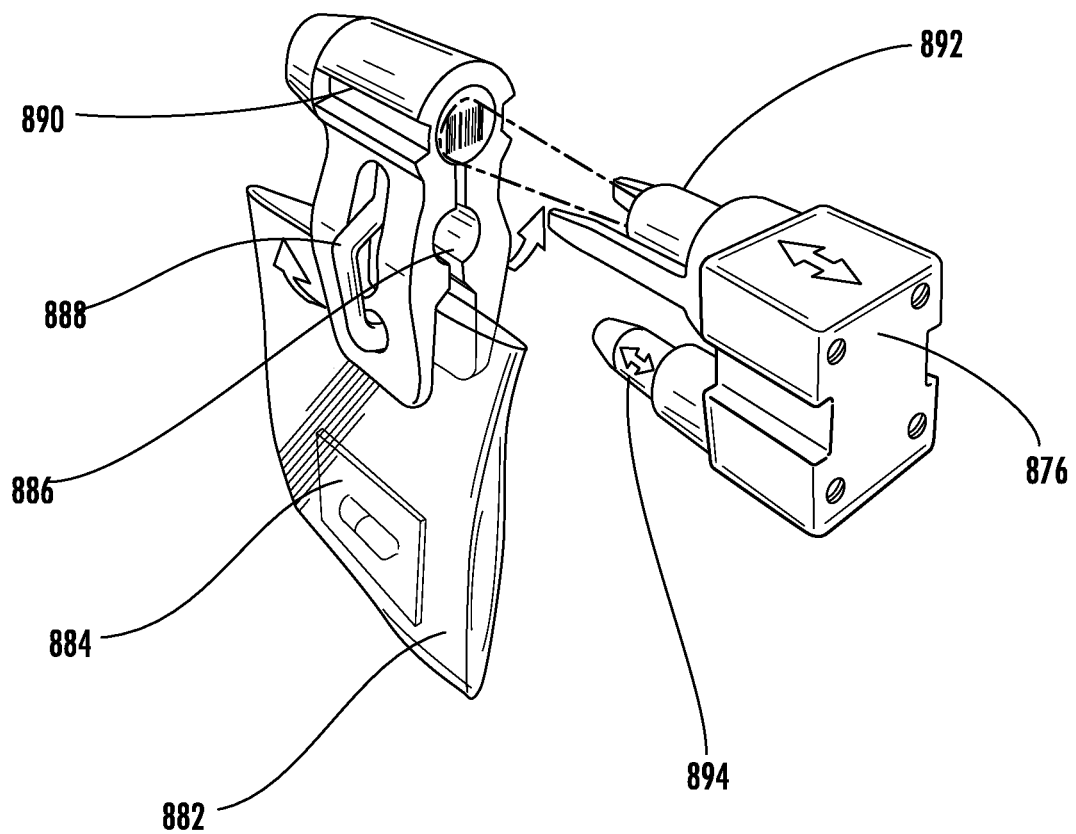
FIG. 57 illustrates an example embodiment of a reader and release mechanism for use with the clips of the example embodiment of FIG. 54.

FIG. 56 illustrates a scanner 876 located near the proximate storage, and FIG. 57 illustrates a detail view of the scanner 876. The scanner 876 may include a reader 892 which is configured to read the identifying indicia of the clip 890. The identifying indicia may be a barcode, text, image, or RFID tag such that the reader 892 may include a barcode scanner, image capture device, or RFID reader. The identifying indicia may either specify the medication 884 in the overpack 882, or alternatively, the identifying indicia may reference a database where the identification of the clip 890 is correlated to a medication attached thereto, where the database is populated when the medication is loaded onto the clip 890. The clip 890 may be scanned upon arrival at the proximate storage, or just before dispensing the medication in response to an authorized request for the medication. The reader 892 may confirm the identity of the clip and medication thereon to confirm that the requested medication matches the medication 884 of the overpack 882 attached to the clip 890. Provided the medication is the anticipated medication, a release mechanism 894 may extend into release recess 886. In response to the release mechanism 894 extending into the release recess 886, the overpack 882 may be released from the clip 890 and hook 888, allowing the overpack and medication contained therein to fall from the clip. The medication may be configured to fall into a tray 896 as illustrated in FIG. 56, and the tray may be configured to move down track 878 for presentation of the medications to the authorized medical person. After a carrier is emptied of medication, or if the medication on the carrier is no longer needed (e.g., when a patient is discharged), the carrier may be advanced by a shuttle back to the unit storage device for retrieval and return to the central pharmacy.

A Third Example Embodiment of a System

As described above, various components may be implemented together to create a system which automates, or enables at least partial automation of the dispensing of medications and supplies to a patient. Another example embodiment of such a system is described herein.

Embodiments described herein may provide for unit-dose overpacks to be prepared for distribution to patients. Such overpacks have also been described to be configured to receive supplies which may accompany certain medications, such as a syringe to accompany a medication vial in a single overpack. While overpacks may be unit-dose specific and/or unit-dose and supply specific, overpacks may also be patient-specific. For example, a single overpack may include unit dose medications for a particular patient for a particular period of time (e.g., for a nurse shift, or for a 24-hour period, etc.). Such an overpack may be a bin which is configured to hold multiple unit-dose medications and may also be configured to hold supplies to accompany the unit-dose medications. The bin may be selected based upon the number and size of medications and/or supplies that it is to be filled with for the particular patient. In some embodiments, the unit-dose medications and/or supplies may be in individual unit-dose overpacks that are loaded into a patient-specific overpack. For example, a unit-dose overpack may include a bag as illustrated in FIG. 4 and a plurality of unit-dose overpacks may be received in a bin, as illustrated at FIG. 1.

Unit-dose medications and supplies may be loaded to a patient-specific overpack by a variety of means including manually, automatically, or a combination of manual and automatic loading. For example, a robot, as shown in FIG. 6, may be configured to load unit-dose medications to a patient-specific overpack. In another example embodiment, as shown in FIG. 14, a user may retrieve the unit-dose medications for a patient, they may scan the unit doses with reader 32, and may load the unit-dose medications in a patient specific bin, such as bin 36. In still another embodiment, a patient-specific overpack may be filled by unit-doses from magazines as illustrated in FIG. 15. In some example embodiments, a patient-specific overpack, such as a bin or an envelope, may be filled by an automated dispensing system such as the Robot-Rx™. The patient-specific overpacks may be configured with security mechanisms, such as the latch 128 of the overpack of FIG. 2. Lockable overpacks may be useful in environments in which control over the overpacks may not be maintained between a central pharmacy (or remote central pharmacy) and the patient. In such an environment, a mechanism to preclude access to patient-specific overpack contents may be desirable.

Upon filling a patient-specific overpack, the overpack may be transported to a unit storage device, or a staging location closer to the patient for whom the medications are intended. Transport to the unit storage device may be performed by a track-based transport system, pneumatic tube system, or other such automated system. In other embodiments, the patient-specific overpacks may be loaded onto a cart. A cart, such as the cart 202 of FIG. 18, may be configured to receive patient-specific overpacks either individually, or on trays, such as tray 200. While the overpack may include a mechanism to preclude access to the contents as described above, the cart or other transport mechanism used to transport the patient-specific overpacks to the unit storage device may include a mechanism for precluding access to the contents of the overpacks. For example, the transport cart may include doors or latches to prevent removal of overpacks from the cart. Access may be granted to authorized medical personnel upon authentication of their identities, such as through biometric identification.

Once the patient-specific overpacks have been transported to a unit storage device, the overpacks may be unloaded. The unloading may include an automated removal of overpacks from a cart, or a manual removal. In an example embodiment in which a track-based transport system or pneumatic tube system is used to transport the patient-specific overpacks, a loading device may be configured to unload the overpacks from the transport device and load the overpacks to a staging area, which may be a unit storage device. The unit storage device of example embodiments may include any of those illustrated in FIGS. 20-25. Optionally, staging may occur in an overhead storage location along a transport route along which the patient specific overpacks are transported to a patient-server or nurse-server for dispensing.

The patient-specific overpacks described above may be filled in response to a medication order received at a central pharmacy, or in response to a system configured to predict the medications anticipated to be needed by a patient over a particular period of time. The overpacks may also be filled by a combination of a medication order and predicted medications, where the medication order includes medications known to be needed by the patient and the predicted medication is medication that the system anticipates may be needed by the patient. The request that a patient-specific overpack be filled may be automated to be generated once or more each day, or the request may come from an authorized medical person. For example, a nurse may request a patient-specific overpack for a patient under their care. Orders generated by a nurse may be sent from a mobile communications device (e.g., a tablet computer, a hand-held computing device, etc.), from a nurse cart (e.g., a computer-on-wheels (COW) or workstation-on-wheels (WOW)), or from a nurse-server, patient-server, or other device in communication with a healthcare facility network.

Once the patient-specific overpacks are received at a proximate storage location or staging area, such as a unit storage device or overhead storage location, for example, the patient-specific overpacks may be ready for transport to an appropriate patient or nurse server. Authorized medical personnel may be alerted to the arrival of a patient-specific overpack at the unit storage device or staging area by an alert sent to a mobile device, a nurse cart, a nurse server, a patient server, etc. Such an alert may advise the authorized medical person that the patient-specific overpack is ready for transport to a location for retrieval by the authorized medical person.

When medications and/or supplies are needed for a patient, the patient-specific overpack may be requested by an authorized medical person. The request may be generated by the authorized medical person using a mobile communications device, a nurse cart, a patient server, a nurse server, or a workstation, for example. The request may be patient-specific, such that an authorized medical person may request the medications for a specific patient. Optionally, a request may include a request for patient-specific overpacks for a plurality of patients, such as all of the patients under a particular authorized medical person's care, or all of the patients in a particular location within the healthcare facility. The request may also specify the desired destination for the patient-specific overpacks. For example, a nurse may request the medications for two patients located in different rooms. The request may indicate that the patient-specific overpacks for both patients should be sent to a location closest to where the nurse is, or is planning to be. Once the request is sent for the patient-specific bin or bins, an estimated time-of-arrival (ETA) of the patient-specific overpacks at the specified location may be generated. The ETA may be provided to the requesting authorized medical person on a mobile device, on their nurse cart, on a patient server or nurse server, or otherwise communicated to the authorized medical person.

The patient-specific overpack(s) may then be transported from the unit storage device or staging area by any one of number of transport devices. For example, a patient-specific overpack may be retrieved by a retrieval device of an X-Y robot, as illustrated in FIG. 23, and loaded, by a loading device, onto a transport device. The transport device may include a car, such as car 320, for transport along the track to the location specified by the authorized medical person. While a track-based transport device is described, other transport devices, such as pneumatic tubes, conveyors, or the like may be used to advance the patient-specific overpacks from the unit storage device or staging area.

Upon arrival of the patient-specific overpacks at the location specified by the requesting authorized medical person, an alert may be generated. The alert may be sent to a mobile device, nurse cart, patient or nurse server, etc. The alert may be an audible alert, a visible alert, or a combination thereof. For example, an audible alert may be provided via the mobile device, and a visible alert, such as a light, may be illuminated at the location where the patient-specific overpacks are to be retrieved. In order to access the patient-specific overpacks requested, the authorized medical person may be required to authenticate their identity at the location where the patient-specific overpacks are to be retrieved. For example, a nurse server including a user interface may allow an authorized medical person to identify themselves through a biometric scan, passcode entry, or key/identification card scan. Once the authorized medical person is identified and authenticated, the patient-specific overpacks may be presented to the authorized medical person.

A variety of mechanisms may be employed to present the patient-specific overpacks to the authorized medical person. For example, the patient-specific overpacks may be awaiting retrieval in an overhead location proximate a nurse server, as shown in FIG. 51. Upon authentication of the authorized medical person, the patient-specific overpacks 590 may be lowered to a retrieval position from which the authorized medical person may retrieve them. Other embodiments of mechanism for presenting the patient-specific overpacks may be used to ensure that the patient-specific overpacks and/or the contents therein, are inaccessible except to an authorized medical person after authentication. The patient-specific overpacks may be held in an inaccessible location or remain in a locked position until such time as the appropriate authorized medical person is authenticated and the patient-specific overpacks are released for retrieval.

An authorized medical person may retrieve one or more patient-specific overpacks in dependence upon the system employed. For example, a nurse may retrieve a plurality of overpacks for a plurality of patients, and load them into a nurse-cart. The nurse may then distribute medications from the patient-specific overpacks as each patient is visited and attended to. Optionally, the patient-specific overpack may be dispensed to an authorized medical person for immediate use, such as using a patient-server in or near a patient room. Upon dispensing of a patient-specific overpack at a patient server, the authorized medical person may administer the medication, and return the overpack.

In example embodiments in which an overpack is re-used and not disposed of, the overpack may be returned via a nurse-server or patient-server, and transported by transport device back to a unit storage device. Optionally, used overpacks may be returned directly to a unit storage device. The used overpacks may be retrieved from the unit storage device, for example, when new patient-specific overpacks are distributed to the unit storage device. Whether the new overpacks are transported by track-based transport, pneumatic tube systems, or transport carts, while the transport device is at the unit storage device, empty overpacks may be loaded to the transport device for return to the central pharmacy.

Figure 58:
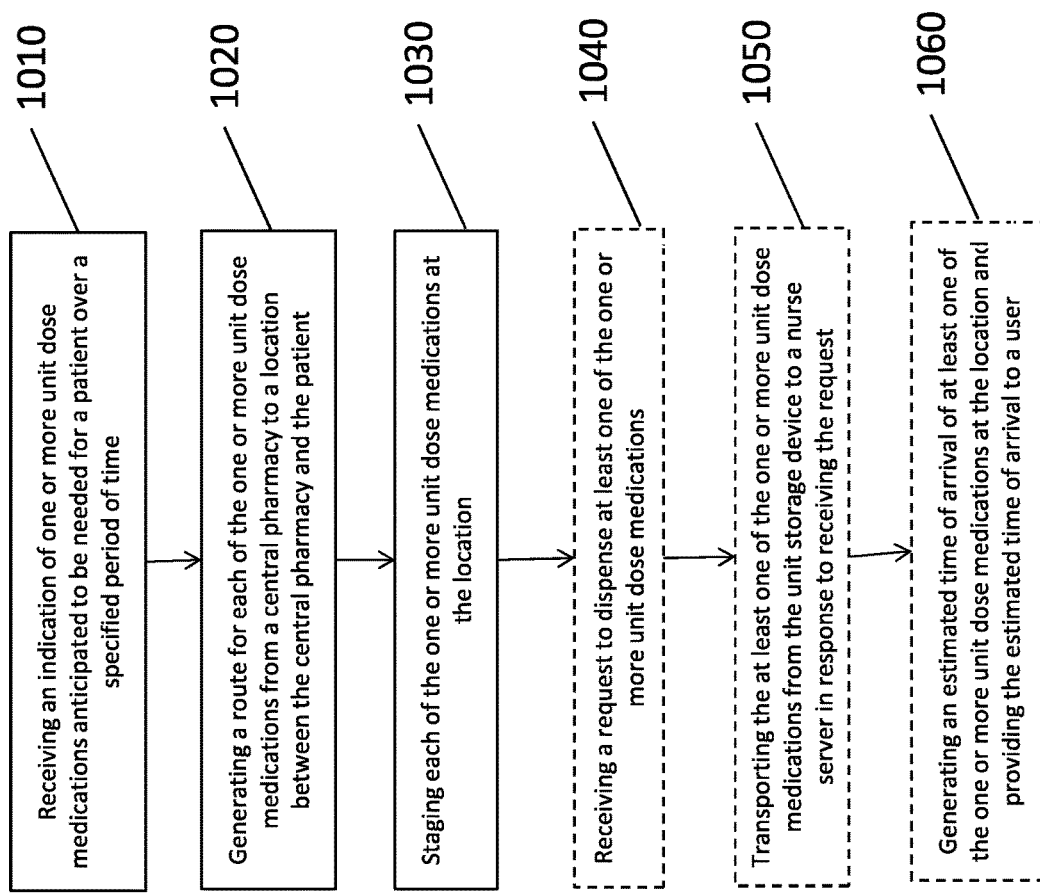
FIG. 58 is a flowchart of a method for transporting medications from a central pharmacy to a patient in a healthcare facility according to an example embodiment of the present invention.

FIG. 58 is a flowchart of a method and program product according to an example embodiment of the present invention. It will be understood that each block of the flowchart and combinations of blocks in the flowchart may be implemented by various means, such as hardware, firmware, processor, circuitry, and/or other devices associated with execution of software including one or more computer program instructions. These computer program instructions may also be stored in a non-transitory computer-readable memory that may direct a computer or other programmable apparatus to function in a particular manner, such that the instructions stored in the computer-readable memory produce an article of manufacture which implements the functions specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the invention, as shown in FIG. 58, may include receiving an indication of one or more unit dose medications anticipated to be needed by a patient at 1010. The method may also include retrieving the one or more unit dose medications from a unit storage device (shown at 1020) and loading the one or more unit dose medications onto a transport device (shown at 1030). The illustrated method further includes transporting the one or more unit dose medications from the unit storage device to a location proximate the patient at 1040 and transferring one or more of the unit dose medications from the transport device to a staging area at the location proximate the patient at 1050.

In some embodiments, certain ones of the operations may be modified or further amplified as described below. Moreover, in some embodiments additional operations may also be included. It should be appreciated that each of the modifications, optional additions, or amplifications below may be included with the operations above either alone or in combination with any others among the features described herein. With reference to the method of FIG. 58, in some example embodiments, the method may include dispensing the one or more unit dose medications from the staging area to authorized medical personnel in response to receiving a request from the authorized medical personnel as shown at 1060. The dispensing may be performed through a nurse server, patient server, or other means for presenting the one or more unit dose medications to the authorized medical person.

In an example embodiment, an apparatus for performing the method of FIG. 58 may include a processor configured to perform some or all of the operations (1010-1060) described above. The processor may, for example, be configured to perform the operations (1010-1060) by performing hardware implemented logical functions executing stored instructions, or executing algorithms for performing each of the operations. Alternatively, the apparatus may include means for performing each of the operations described above.

An example of an apparatus according to an example embodiment may include at least one processor and at least one memory including computer program code. The at least one memory and the computer program code may be configured to, with the at least one processor, cause the apparatus to perform the operations 1010-1060 (with or without the modifications and amplifications described above in any combination).

An example of a computer program product according to an example embodiment may include at least one computer-readable storage medium having computer-executable program code portions stored therein. The computer-executable program code portions may include program code instructions for performing operations 1010-1060 (with or without the modifications and amplifications described above in any combination).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for inventory management of a medication unit dose storage device, the method comprising:
   receiving, within the storage device, a plurality of unit dose medications of a plurality of medication types;
   identifying, for each of the plurality of unit dose medications, medication information associated with the respective unit dose medication;
   providing for storage of the plurality of unit dose medications, each unit dose medication stored in a uniquely identified storage location within the storage device;
   monitoring contents of the storage device;
   providing, via a communications interface, an indication of removal of one or more of the plurality of unit dose medications;
   determining demand for a first medication type;
   determining a future shortage of the first medication type in response to the determined demand; and
   generating a restock request for the first medication type.

2. The method of claim 1, wherein generating a restock request for the first medication type comprises:
   generating the restock request for the first medication type for a central pharmacy;
   receiving an indication that the central pharmacy does not have sufficient inventory to meet the demand; and
   generating an order for a distribution center in response to the central pharmacy not having sufficient inventory to meet the demand.

3. The method of claim 1, wherein the medication information comprises one or more of: lot number, manufacture date, expiration date, medication type, or medication dose.

4. The method of claim 1, further comprising:
   tracking inventory of medication unit doses at one or more other medication unit storage devices.

5. The method of claim 4, wherein the medication information comprises an expiration date for each respective unit dose medication, and wherein the method further comprises:
   identifying one or more unit dose medications having an expiration date approaching;
   identifying at least one other medication unit dose storage device having a relatively higher demand for the identified one or more unit dose medications; and
   directing transfer of the identified one or more unit dose medications between the medication unit dose storage device and the one or more other medication unit dose storage devices.

6. The method of claim 1, wherein identifying demand for a first medication type comprises:
   identifying an increase in one or more patient diagnoses; and
   determining an increase in demand for one or more medication types related to the one or more patient diagnoses in response to the increase in the one or more patient diagnoses.

7. The inventory control system of claim 1, wherein the medication unit dose storage device comprises a mobile storage device, and wherein the processing circuitry is further configured to:
monitor a location of the mobile storage device within a healthcare facility.

8. The method of claim 1, wherein the medication unit dose storage device comprises a mobile storage device, and wherein the method further comprises:
monitoring a location of the mobile storage device within a healthcare facility.

9. The method of claim 8, further comprising:
identifying a restock condition for the medication unit storage device; and
providing an instruction for movement of the medication unit storage device to a central pharmacy for replenishment.

10. An apparatus comprising processing circuitry and at least one memory including computer program code, the at least one memory and computer program code configured to, with the processing circuitry, cause the apparatus to at least:
receive, within a storage device, a plurality of unit dose medications of a plurality of medication types;
identify, for each of the plurality of unit dose medications, medication information associated with the respective unit dose medication;
provide for storage of the plurality of unit dose medications, each unit dose medication stored in a uniquely identified storage location within the storage device;
monitor contents of the storage device;
provide an indication of removal of one or more of the plurality of unit dose medications;
determine demand for a first medication type;
determine a future shortage of the first medication type in response to the determined demand; and
generate a restock request for the first medication type.

11. The apparatus of claim 10, wherein causing the apparatus to generate a restock request for the first medication type comprises causing the apparatus to:
generate the restock request for the first medication type for a central pharmacy;
receive an indication that the central pharmacy does not have sufficient inventory to meet the demand; and
generate an order for a distribution center in response to the central pharmacy not having sufficient inventory to meet the demand.

12. The apparatus of claim 10, wherein the medication information comprises one or more of: lot number, manufacture date, expiration date, medication type, or medication dose.

13. The apparatus of claim 10, wherein the apparatus is further caused to:
track inventory of medication unit doses at one or more other medication unit storage devices.

14. The apparatus of claim 13, wherein the medication information comprises an expiration date for each respective unit dose medication, and wherein the apparatus is further caused to:
identify one or more unit dose medications having an expiration date approaching;
identify at least one other medication unit dose storage device having a relatively higher demand for the identified one or more unit dose medications; and
direct transfer of the identified one or more unit dose medications between the medication unit dose storage device and the one or more other medication unit dose storage devices.

15. The apparatus of claim 10, wherein the medication unit dose storage device comprises a mobile storage device, and wherein the apparatus is further caused to:
monitor a location of the mobile storage device within a healthcare facility.

16. The apparatus of claim 15, wherein the apparatus is further caused to:
identify a restock condition for the medication unit storage device; and
provide an instruction for movement of the medication unit storage device to a central pharmacy for replenishment.

17. The apparatus of claim 10, wherein causing the apparatus to identify demand for a first medication type comprises causing the apparatus to:
identify an increase in one or more patient diagnoses; and
determine an increase in demand for one or more medication types related to the one or more patient diagnoses in response to the increase in the one or more patient diagnoses.

18. An inventory control system comprising:
a memory comprising medication unit dose storage information; and
processing circuitry configured to:
receive, within a storage device, a plurality of unit dose medications of a plurality of medication types;
identify, for each of the plurality of unit dose medications, medication information associated with the respective unit dose medication;
provide for storage of the plurality of unit dose medications, each unit dose medication stored in a uniquely identified storage location within the storage device;
monitor contents of the storage device;
provide an indication of removal of one or more of the plurality of unit dose medications;
determine demand for a first medication type;
determine a future shortage of the first medication type in response to the determined demand; and
generate a restock request for the first medication type.

19. The inventory control system of claim 18, wherein the processing circuitry configured to generate a restock request for the first medication type comprises the processing circuitry being configured to:
generate the restock request for the first medication type for a central pharmacy;
receive an indication that the central pharmacy does not have sufficient inventory to meet the demand; and
generate an order for a distribution center in response to the central pharmacy not having sufficient inventory to meet the demand.

20. The inventory control system of claim 18, wherein the medication information comprises an expiration date for each respective unit dose medication, and wherein the processing circuitry is further configured to:
identify one or more unit dose medications having an expiration date approaching;
identify at least one other medication unit dose storage device having a relatively higher demand for the identified one or more unit dose medications; and direct transfer of the identified one or more unit dose medications between the medication unit dose storage device and the one or more other medication unit dose storage devices.

* * * * *